(12) United States Patent
Greenlee et al.

(10) Patent No.: US 12,209,092 B2
(45) Date of Patent: Jan. 28, 2025

(54) INHIBITORS OF GLI1 AS THERAPEUTIC AGENTS

(71) Applicant: NEW YORK UNIVERSITY, New York, NY (US)

(72) Inventors: William J. Greenlee, Teaneck, NJ (US); John Van Drie, North Andover, MA (US); Xinyan Huang, Paramus, NJ (US); James Salzer, New York, NY (US); Nadim Shohdy, Garden City, NY (US)

(73) Assignee: New York University, New York, NY (US)

( * ) Notice: Subject to any disclaimer, the term of this patent is extended or adjusted under 35 U.S.C. 154(b) by 894 days.

(21) Appl. No.: 17/295,351

(22) PCT Filed: Nov. 19, 2019

(86) PCT No.: PCT/US2019/062263
§ 371 (c)(1),
(2) Date: May 19, 2021

(87) PCT Pub. No.: WO2020/106751
PCT Pub. Date: May 28, 2020

(65) Prior Publication Data
US 2022/0009935 A1  Jan. 13, 2022

Related U.S. Application Data

(60) Provisional application No. 62/769,510, filed on Nov. 19, 2018.

(51) Int. Cl.
| | | |
|---|---|---|
| C07D 487/04 | (2006.01) |
| C07D 401/04 | (2006.01) |
| C07D 471/04 | (2006.01) |
| C07D 471/18 | (2006.01) |
| C07D 519/00 | (2006.01) |

(52) U.S. Cl.
CPC ......... *C07D 487/04* (2013.01); *C07D 401/04* (2013.01); *C07D 471/04* (2013.01); *C07D 471/18* (2013.01); *C07D 519/00* (2013.01)

(58) Field of Classification Search
CPC .................................................. C07D 487/04
See application file for complete search history.

(56) References Cited

U.S. PATENT DOCUMENTS

| | | |
|---|---|---|
| 6,683,192 B2 | 1/2004 | Baxter et al. |
| 6,767,888 B1 | 7/2004 | Mahanthappa |
| 9,611,276 B2 | 4/2017 | Chen et al. |

FOREIGN PATENT DOCUMENTS

| | | |
|---|---|---|
| EP | 2635578 B1 | 9/2013 |
| JP | 2018-531982 A | 11/2018 |
| SU | 1069387 A1 | 11/1985 |
| WO | 2003027234 A3 | 12/2003 |
| WO | 2013013190 A1 | 1/2013 |
| WO | 2013112859 A1 | 8/2013 |
| WO | 2017103670 A1 | 6/2017 |

OTHER PUBLICATIONS

Moshai et al. "Targeting the hedgehog-glioma-associated oncogene homolog pathway inhibits bleomycin-induced lung fibrosis in mice." Am J Respir Cell Mol Biol. Jul. 2014;51(1):11-25. doi: 10.1165/rcmb.2013-0154OC. PMID: 24450438.
Lauth et al, "Inhibition of GLI-mediated transcription and tumor cell growth by small-molecule antagonists", Proceedings of the National Academy of Sciences, vol. 104, No. 20, May 15, 2007 (May 15, 2007), p. 8455-8460, DOI: 10.1073/pnas.0609699104.
Hyman et al, "Small-molecule inhibitors reveal multiple strategies for Hedgehog pathway blockade", Proceedings of the National Academy of Sciences, vol. 106, No. 33, Aug. 18, 2009 (Aug. 18, 2009), p. 14132-14137, doi: 10.1073/pnas.0907134106. Epub Aug. 5, 2009. PMID: 19666565; PMCID: PMC2721821.
Yutilov et al., "Synthesis and biological activity of N(5)-β-oxyethylspinaceamines", Pharmaceutical Chemistry Journal, vol. 23, No. 2, Feb. 1, 1989 (Feb. 1, 1989), p. 119-122, https://doi.org/10.1007/BF00764457.
Whitaker et al., Urinary myelin basic protein-like material as a correlate of the progression of multiple sclerosis. Ann Neurol. Oct. 1995; 38(4):625-32. doi: 10.1002/ana.410380411. PMID: 7574459.
Mastrangelo et al, Role and inhibition of GLI1 protein in cancer. Lung Cancer (Auckl). 2018;9:35-43. http://dx.doi.org/10.2147/LCTT.S124483.
Chen et al, Beachy PA. Small molecule modulation of Smoothened activity. Proc Natl Acad Sci U S A. Oct. 29, 2002;99 (22):14071-6. doi: 10.1073/pnas. 182542899. Epub Oct. 21, 2002. PMID: 12391318; PMCID: PMC137838.
Frank-Kamenetsky et al. Small-molecule modulators of Hedgehog signaling: identification and characterization of Smoothened agonists and antagonists. J Biol 1, 10 (2002). https://doi.org/10.1186/1475-4924-1-10.
Espinosa-Bustos et al, State of the art of Smo antagonists for cancer therapy: advances in the target receptor and new ligand structures. Future Med Chem. Mar. 2019;11(6):617-638. doi: 10.4155/fmc-2018-0497. Epub Mar. 26, 2019. PMID: 30912670.
Ohashi et al "Synthesis and evaluation of hedgehog signaling inhibitor with novel core system." Bioorganic & Medicinal Chemistry 23 (2015) 4777-4791, http://dx.doi.org/10.1016/j.bmc.2015.05.036.
American Chemical Society Registry(STN),Jan. 30, 2017,CAS2061675-32-7.
American Chemical Society Registry(STN),Jun. 18, 2015,CAS1783269-48-6.
American Chemical Society Registry(STN),Jun. 18, 2015,CAS1783051-04-6.

(Continued)

Primary Examiner — Yong S. Chong
(74) Attorney, Agent, or Firm — Hodgson Russ LLP

(57) ABSTRACT

This disclosure relates to compounds, pharmaceutical compositions comprising them, and methods of using the compounds and compositions for treating diseases related to glioma-associated oncogene (Gli) expression. More particularly, this disclosure relates to bicyclic compounds and pharmaceutical compositions thereof, methods of inhibiting Gli expression with these compounds, and methods of treating diseases related to Gli expression.

6 Claims, No Drawings

Specification includes a Sequence Listing.

(56) References Cited

OTHER PUBLICATIONS

American Chemical Society Registry(STN),Jun. 6, 2014,CAS1609747-11-6.
American Chemical Society REGISTRY(STN),Dec. 18, 2013,CAS1497613-40-7.
PCT International Search Report for International Application No. PCT/US2019/062263, mailed Feb. 4, 2020, 4pp.
PCT Written Opinion for International Application No. PCT/US2019/062263, mailed Feb. 4, 2020, 5pp.
PCT International Preliminary Report on Patentability for International Application No. PCT/US2019/062263, issued May 25, 2021, 6pp.

```
                         SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Gli 1 inhibitor siRNA

<400> SEQUENCE: 1
gucauuauca aauuucucct t                                                    21

<210> SEQ ID NO 2
<211> LENGTH: 21
<212> TYPE: DNA
<213> ORGANISM: Artificial Sequence
<220> FEATURE:
<223> OTHER INFORMATION: Gli 1 inhibitor siRNA

<400> SEQUENCE: 2
agaagaaaag agugggccct t                                                    21

<210> SEQ ID NO 3
<211> LENGTH: 21
<212> TYPE: DNA
<213> ORGANISM: Artificial Sequence
<220> FEATURE:
<223> OTHER INFORMATION: Gli 1 inhibitor siRNA

<400> SEQUENCE: 3
uccgguguuu ucuucaucct t                                                    21

<210> SEQ ID NO 4
<211> LENGTH: 21
<212> TYPE: DNA
<213> ORGANISM: Artificial Sequence
<220> FEATURE:
<223> OTHER INFORMATION: Gli1 inhibitor siRNA

<400> SEQUENCE: 4
gagaucuucc cuucauacct t                                                    21

<210> SEQ ID NO 5
<211> LENGTH: 21
```

```
<212> TYPE: DNA
<213> ORGANISM: Artificial Sequence
<220> FEATURE:
<223> OTHER INFORMATION: Gli 1 inhibitor siRNA

<400> SEQUENCE: 5
aacuccacag gcauacagga u                                              21
```

INHIBITORS OF GLI1 AS THERAPEUTIC AGENTS

CROSS-REFERENCE TO RELATED APPLICATIONS

This application is a National Phase of PCT Patent Application No. PCT/US2019/062263 having International filing date of Nov. 19, 2019, which claims the benefit of priority under 35 U.S.C. § 119 (e) of U.S. Provisional Patent Application No. 62/769,510, filed on Nov. 19, 2018, entitled "INHIBITORS OF GLI1 AS THERAPEUTIC AGENTS." The contents of the above applications are all incorporated by reference as if fully set forth herein in their entirety.

BACKGROUND OF DISCLOSURE

Field of Disclosure

This disclosure relates to compounds, pharmaceutical compositions comprising them, and methods of using the compounds and compositions for treating diseases related to glioma-associated oncogene (Gli) expression. More particularly, this disclosure relates to bicyclic compounds and pharmaceutical compositions thereof, methods of inhibiting Gli expression with these compounds, and methods of treating diseases related to Gli expression.

Technical Background

Hedgehog (Hh) signaling pathway plays a critical role in the initiation, proliferation, invasion, and metastasis of a wide variety of cancers. The Hh pathway is also implicated in the regulation and maintenance of cancer stem cells (CSCs), providing a link between the Hh signaling in the regulation of normal stem cells and its role in CSCs maintenance.

More recently, the involvement of Smo and Gli was also addressed in the context of myelin regeneration. Disorders of myelination can produce significant impairment in sensory, motor and other types of functioning when nerve signals reach their targets slowly, asynchronously, intermittently, or not at all. Disorders of myelination are also associated with progressive loss of the axons which further contributes to neurological impairment. Disorders of myelination can be demyelinating, as a result of removal or degradation of myelin already formed; or dysmyelinating, as a result of deficient or defective myelin development or maintenance. Many disorders affect both central nervous system (CNS) and peripheral nervous system (PNS) myelin. Included among the more common disorders of CNS myelination are multiple sclerosis (MS) and the leukodystrophies, and among disorders of PNS myelination are the Guillain Barre Syndrome, and the Charcot Marie Tooth inherited peripheral neuropathies.

Hh signaling is initiated by the binding of ligand namely Sonic Hedgehog (Shh), Indian Hedgehog (Ihh) or Desert Hedgehog (Dhh) to its receptor, Patched (Ptch). Canonical Shh signaling is mediated by interactions of the Ptch with the G-protein coupled transmembrane co-receptor smoothened (Smo). Binding of Shh to Ptch relieves its inhibition of Smo and thereby activates the Gli family of proteins (also known as zinc finger transcription factors).

Vertebrates have at least three distinct Gli proteins, Gli1, Gli2, and Gli3 (glioma-associated oncogene 1, 2, and 3). Gli proteins participate in the final step of the Hh/Gli signaling pathway, and they regulate several genes, including those that are related to cell cycle control and Hh/Gli signaling. Gli1 acts as a transcriptional activator, whereas Gli2 and Gli3 act as both activators and repressors. The proteins in Gli family share a highly conserved $C_2$—$H_2$ zinc finger domain (having five zinc finger DNA-binding motifs) and recognize consensus Gli-selective sequences that regulate transcription. Of the three Gli proteins, Gli1 expression is considered a sensitive readout for, and an indicator of the highest levels of Shh signaling.

SUMMARY OF THE DISCLOSURE

The disclosure provides novel Gli inhibitors useful for treating diseases related to Gli expression. Thus, one aspect of the disclosure provides a compound of formula (I):

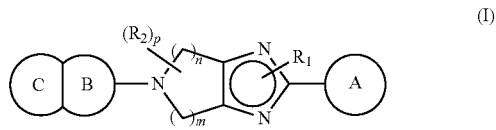

or a pharmaceutically acceptable salt thereof, wherein
m is an integer 1 or 2;
n is an integer 1 or 2;
p is an integer 0, 1, or 2;
$R_1$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), alkoxy($C_1$-$C_6$ alkyl), —OH, and oxetanyl;
$R_2$ is $C_1$-$C_6$ alkyl;
ring A represents an aryl optionally substituted with one or more $R_3$, heteroaryl optionally substituted with one or more $R_3$, or $C_4$-$C_8$ cycloalkyl optionally substituted with one or more $R_3$; and
ring B and ring C form a bicyclic heteroaryl, bicyclic heterocyclyl, or bicyclic cycloalkyl moiety, each optionally substituted with one or more $R_4$;
wherein
each $R_3$ is independently selected from halogen, —$NO_2$, —CN, $C_1$-$C_6$ alkyl optionally substituted with one or more $R_5$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy ($C_1$-$C_6$ alkoxy), amino($C_1$-$C_6$ alkyl), —$CONH_2$, —CONH($C_1$-$C_6$ alkyl), —CON($C_1$-$C_6$ alkyl)$_2$, —CONH—OH, —$CO_2$H, —$CO_2$($C_1$-$C_6$ alkyl), —$SO_2R_7$, —$SO_2OR_7$, —$SO_2N(R_7)_2$, cyclopropylethynyl, aryl optionally substituted with one or more $R_6$, heteroaryl optionally substituted with one or more $R_6$, heterocyclyl optionally substituted with one or more $R_6$, and $C_3$-$C_8$ cycloalkyl optionally substituted with one or more $R_6$;
each $R_4$ is independently selected from halogen, —$NO_2$, —CN, $C_1$-$C_6$ alkyl optionally substituted with one or more $R_5$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy ($C_1$-$C_6$ alkoxy), amino($C_1$-$C_6$ alkyl), —$CONH_2$, —CONH($C_1$-$C_6$ alkyl), —CON($C_1$-$C_6$ alkyl)$_2$, —CONH—OH, —$CO_2$H, —$CO_2$($C_1$-$C_6$ alkyl), —$SO_2R_7$, —$SO_2OR_7$, —$SO_2N(R_7)_2$, cyclopropylethynyl, aryl optionally substituted with one or more $R_6$, heteroaryl optionally substituted with one or more $R_6$, heterocyclyl optionally substituted with one or more $R_6$, $C_3$-$C_8$ cycloalkyl optionally substituted with one or more $R_6$, aryloxy optionally substituted with one or more $R_6$, heteroaryloxy optionally substituted with one or more $R_6$, heterocyclyloxy optionally substituted with one or more $R_6$, cycloalkyloxy optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O;

each $R_5$ is independently selected from the group consisting of halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkoxy), alkoxy($C_1$-$C_6$ alkoxy), —$SO_2R_7$, —$SO_2OR_7$, and —$SO_2N(R_7)_2$;

each $R_6$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy; and each $R_7$ is independently selected from the group consisting of hydrogen, $C_1$-$C_6$ alkyl, phenyl, or tolyl.

Another aspect of the disclosure provides a compound of formula (II):

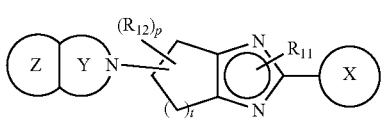

(II)

or a pharmaceutically acceptable salt thereof, wherein t is an integer 1 or 2;

q is an integer 0, 1, or 2;

$R_{11}$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), alkoxy($C_1$-$C_6$ alkyl), —OH, and oxetanyl;

$R_{12}$ is $C_1$-$C_6$ alkyl;

ring X represents an aryl optionally substituted with one or more $R_{13}$, heteroaryl optionally substituted with one or more $R_{13}$, or $C_4$-$C_8$ cycloalkyl optionally substituted with one or more $R_{13}$; and ring Y and ring Z form a bicyclic heteroaryl or bicyclic heterocyclyl moiety, each optionally substituted with one or more $R_{14}$;

wherein each $R_{13}$ is independently selected from halogen, —$NO_2$, —CN, $C_1$-$C_6$ alkyl optionally substituted with one or more $R_{15}$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$CONH_2$, —CONH($C_1$-$C_6$ alkyl), —CON($C_1$-$C_6$ alkyl)$_2$, —CONH—OH, —$CO_2H$, —$CO_2(C_1$-$C_6$ alkyl), —$SO_2R_{17}$, —$SO_2OR_{17}$, —$SO_2N(R_{17})_2$, cyclopropylethynyl, aryl optionally substituted with one or more $R_{16}$, heteroaryl optionally substituted with one or more $R_{16}$, heterocyclyl optionally substituted with one or more $R_{16}$, and $C_3$-$C_8$ cycloalkyl optionally substituted with one or more $R_{16}$;

each $R_{14}$ is independently selected from halogen, —$NO_2$, —CN, $C_1$-$C_6$ alkyl optionally substituted with one or more $R_{15}$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$CONH_2$, —CONH($C_1$-$C_6$ alkyl), —CON($C_1$-$C_6$ alkyl)$_2$, —CONH—OH, —$CO_2H$, —$CO_2(C_1$-$C_6$ alkyl), —$SO_2R_{17}$, —$SO_2OR_{17}$, —$SO_2N(R_{17})_2$, cyclopropylethynyl, aryl optionally substituted with one or more $R_{16}$, heteroaryl optionally substituted with one or more $R_{16}$, heterocyclyl optionally substituted with one or more $R_{16}$, $C_3$-$C_8$ cycloalkyl optionally substituted with one or more $R_{16}$, aryloxy optionally substituted with one or more $R_{16}$, heteroaryloxy optionally substituted with one or more $R_{16}$, heterocyclyloxy optionally substituted with one or more $R_{16}$, cycloalkyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O;

each $R_{15}$ is independently selected from the group consisting of halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkoxy), alkoxy($C_1$-$C_6$ alkoxy), —$SO_2R_{17}$, —$SO_2OR_{17}$, and —$SO_2N(R_{17})_2$;

each $R_{16}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy; and each $R_{17}$ is independently selected from the group consisting of hydrogen, $C_1$-$C_6$ alkyl, phenyl, or tolyl.

Another aspect of the disclosure provides a pharmaceutical composition including one or more compounds of the disclosure as described herein (e.g., compounds of formula (I) and/or (II)) and a pharmaceutically acceptable carrier, solvent, adjuvant or diluent.

Another aspect of the disclosure provides a method of treating a neurological disorder, the method including administering to a subject in need of such treatment one or more compounds of the disclosure as described herein or a pharmaceutical composition of the disclosure as described herein.

In certain embodiments of this aspect, the neurological disorder is selected from multiple sclerosis, central pontine myelinolysis, acute disseminated encephalomyelitis, progressive multifocal leukoencephalopathy, subacute sclerosing panencephalitis, post-infectious encephalomyelitis, chronic inflammatory demyelinating polyneuropathy, Devic's disease, Balo's concentric sclerosis, the leukodystrophies, optic neuritis, transverse myelitis, cerebral palsy, spinal cord injury, age-associated myelin deficiency, Alzheimer's Disease, and acquired and inherited neuropathies in the peripheral nervous system. In certain embodiments of this aspect, the neurological disorder is multiple sclerosis. In certain embodiments of this aspect, the neurological disorder is Alzheimer's Disease.

Another aspect of the disclosure provides a method of treating a non-CNS disease, the method including administering to a subject in need of such treatment one or more compounds of the disclosure as described herein or a pharmaceutical composition of the disclosure as described herein.

In certain embodiments of this aspect, the non-CNS disease is cancer. In certain embodiments, the cancer is characterized by elevated Gli1. In certain embodiments, the cancer is breast cancer, pancreatic cancer, colon cancer, lung cancer, rhabdomyosarcoma, basal-cell carcinoma, glioblastoma, medulloblastoma, leukemia, prostate cancer, skin cancer, lymphoma, esophageal cancer, ovarian cancer, thyroid cancer, osteosarcoma, liver cancer, multiple endocrine neoplasia, gastrointestinal cancer, or mesothelioma.

In certain embodiments of this aspect, the non-CNS disease is cystic kidney disease, chronic liver disease, Hepatitis, C, obstructive pulmonary disease, organ fibrosis (including, e.g., kidney fibrosis, cardiac fibrosis, and pulmonary fibrosis), or rheumatoid arthritis.

Another aspect of the disclosure provides a method of inhibiting Gli1, the method including administering one or more compounds of the disclosure as described herein or a pharmaceutical composition of the disclosure as described herein.

Another aspect of the disclosure provides a method of enhancing remeyelination, the method including administering one or more compounds of the disclosure as described herein or a pharmaceutical composition of the disclosure as described herein.

DETAILED DESCRIPTION

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials and methods provide improvements in treatment of diseases or disorders associated with Gli1 and/or Gli2 expression. Specifically, the inventors found that the compounds of the disclosure inhibit Gli1 and/or Gli2 with low-µM and sub-µM $IC_{50}$. For example, in certain embodiments, the compounds of the disclosure inhibit Gli1 and/or Gli2 at $IC_{50}$ of no more than 10 µM, or no more than 1 µM, or no more than 100 nM, or even no more than 10 nM.

Accordingly, one aspect of the disclosure provides compounds of formula (I) as provided above.

One of skill in the art recognizes that the compounds of formula (I) exist in the isomer form (I-1) and (I-2):

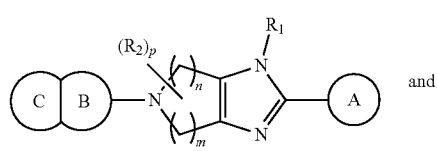

(I-1)

and

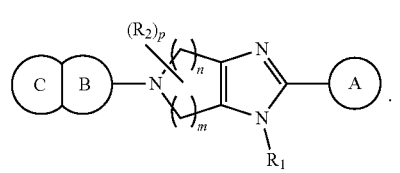

(I-2)

In some embodiments, the compounds of formula (I) as otherwise described herein are those of isomer form (I-1).

In some embodiments, the compounds of formula (I) as otherwise described herein are those of isomer form (I-2).

In some embodiments, the compounds of formula (I) as otherwise described herein are those wherein m is 2. In one embodiment, the disclosure provides compounds of formula (I) as otherwise described herein where m is 2, and n is 1, e.g., the compounds of formula (I-3):

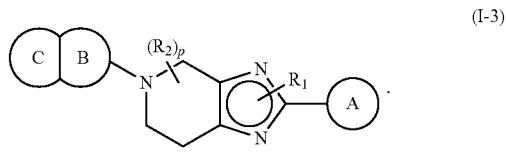

(I-3)

In some embodiments, the compounds of formula (I-3) as otherwise described herein are those of isomer form (I-4).

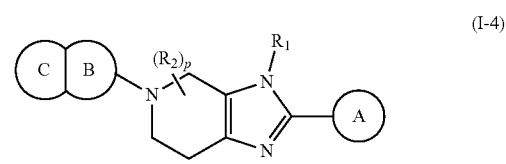

(I-4)

In some embodiments, the compounds of formula (I-3) as otherwise described herein are those of isomer form (I-5).

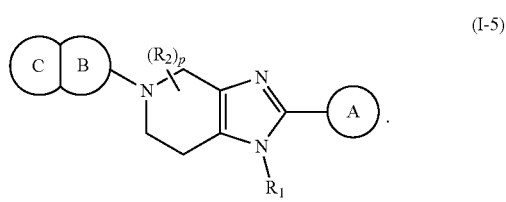

(I-5)

In one embodiment, the disclosure provides compounds of formula (I) as otherwise described herein where both m and n are 2, e.g., the compounds of formula (I-6):

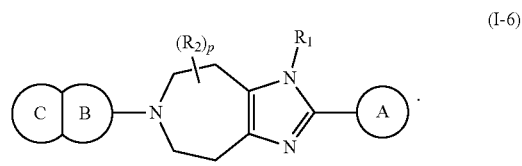

(I-6)

In some embodiments, the compounds of formula (I) as otherwise described herein are those wherein m is 1. In one embodiment, the disclosure provides compounds of formula (I) as otherwise described herein where both m and n are 1. Such compounds are of formula (I-7):

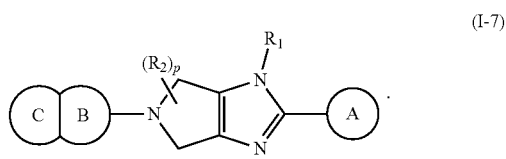

(I-7)

Another embodiment of the disclosure provides compounds of formula (I)-(I-7) as otherwise described herein where p is 0.

In certain embodiments of the disclosure, the compounds of formula (I)-(I-7) as otherwise described herein are those wherein p is 1 or 2. In one embodiment, p is 1. In another embodiment p is 2. In one embodiment, the disclosure provides compounds as otherwise described herein where $R_2$ is $C_1$-$C_3$ alkyl. In another embodiment, $R_2$ is ethyl or methyl. In another embodiment, $R_2$ is methyl.

Another embodiment of the disclosure provides compounds of formula (I)-(I-7) as otherwise described herein where $R_1$ is selected from hydrogen, $C_1$-$C_3$ alkyl, $C_1$-$C_3$ haloalkyl, $C_3$-$C_6$ cycloalkyl, heterocyclyl, hydroxy($C_1$-$C_3$ alkyl), alkoxy($C_1$-$C_3$ alkyl), —OH, and oxetanyl. Yet another embodiment of the disclosure provides compounds of formula (I)-(I-7) as otherwise described herein where $R_1$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), —OH, and oxetanyl. In certain embodiments of the disclosure, $R_1$ is hydrogen or $C_1$-$C_6$ alkyl. In certain embodiments of the disclosure, $R_1$ is hydrogen or $C_1$-$C_4$ alkyl. In certain embodiments of the disclosure, $R_1$ is hydrogen or $C_1$-$C_3$ alkyl. In certain embodiments of the disclosure, $R_1$ is hydrogen, methyl, or ethyl. In certain embodiments of the disclosure, $R_1$ is hydrogen or methyl. In certain embodiments of the disclosure, $R_1$ is hydrogen. In certain embodiments of the disclosure, $R_1$ is methyl. In certain embodiments of the disclosure, $R_1$ is hydrogen, methyl, trifluoroethyl, hydroxyethyl, —OH, and oxetanyl. In certain embodiments of the disclosure, $R_1$ is hydrogen, $C_1$-$C_3$ alkyl, $C_1$-$C_3$ haloalkyl, hydroxy($C_1$-$C_3$ alkyl), —OH, and oxetanyl.

One embodiment of the disclosure provides compounds of formula (I)-(I-7) as otherwise described herein where ring A represents an aryl optionally substituted with one or more $R_3$ or heteroaryl optionally substituted with one or more $R_3$.

In certain embodiments of the disclosure, the compounds of formula (I)-(I-7) as otherwise described herein are those where ring A represents phenyl optionally substituted with one or more $R_3$ or 6-membered heteroaryl optionally substituted with one or more $R_3$.

One embodiment of the disclosure provides compounds of formula (I)-(I-7) as otherwise described herein where ring A represents phenyl optionally substituted with one or more $R_3$ or pyridinyl optionally substituted with one or more $R_3$.

In certain embodiments of the disclosure, the compounds of formula (I)-(I-7) as otherwise described herein are those where ring A represents phenyl optionally substituted with one or more $R_3$. In certain embodiments of the disclosure, ring A represents phenyl substituted with one or more $R_3$. In certain embodiments of the disclosure, ring A represents phenyl optionally substituted with one $R_3$.

One embodiment of the disclosure provides compounds of formula (I)-(I-7) as otherwise described herein where ring A represents phenyl substituted with one $R_3$.

One embodiment of the disclosure provides compounds of formula (I)-(I-7) as otherwise described herein where ring A represents phenyl substituted with halogen (e.g., chloro or fluoro).

One embodiment of the disclosure provides compounds of formula (I)-(I-7) as otherwise described herein where ring A represents 2-chlorophenyl.

Another embodiment of the disclosure provides compounds of formula (I)-(I-7) as otherwise described herein where ring A represents phenyl (i.e., unsubstituted phenyl).

In certain embodiments of the disclosure, the compounds as otherwise described herein are those wherein each $R_3$ is independently selected from halogen, $C_1$-$C_6$ alkyl optionally substituted with one or more $R_5$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_7$, cyclopropylethynyl, aryl optionally substituted with one or more $R_6$, heteroaryl optionally substituted with one or more $R_6$, heterocyclyl optionally substituted with one or more $R_6$, and $C_3$-$C_8$ cycloalkyl optionally substituted with one or more $R_6$. In certain embodiments of the disclosure, each $R_3$ is independently selected from halogen, $C_1$-$C_6$ alkyl optionally substituted with one or more $R_5$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_7$, cyclopropylethynyl, aryl, heteroaryl, heterocyclyl, and $C_3$-$C_8$ cycloalkyl. In certain embodiments of the disclosure, each $R_3$ is independently selected from halogen, $C_1$-$C_6$ alkyl optionally substituted with one or more $R_5$, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_7$, cyclopropylethynyl, aryl, heteroaryl, heterocyclyl, and $C_3$-$C_8$ cycloalkyl. In certain embodiments of the disclosure, each $R_3$ is independently selected from halogen, $C_1$-$C_6$ alkyl optionally substituted with one or more $R_5$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SO$_2$R$_7$, cyclopropylethynyl, aryl, heteroaryl, heterocyclyl, and $C_3$-$C_8$ cycloalkyl. In certain embodiments of the disclosure, each $R_3$ is independently selected from halogen, $C_1$-$C_6$ alkyl optionally substituted with one or more $R_5$, $C_1$-$C_6$ haloalkyl, —OH, $C_1$-$C_6$ alkoxy, $C_1$-$C_6$ haloalkoxy, —SO$_2$R$_7$, cyclopropylethynyl, and heteroaryl. In certain embodiments of the disclosure, each $R_3$ is independently selected from halogen, $C_1$-$C_6$ alkoxy, —SO$_2$R$_7$, cyclopropylethynyl, and heteroaryl. In certain embodiments of the disclosure, each $R_3$ is independently selected from halogen, $C_1$-$C_6$ alkoxy, cyclopropylethynyl, and heteroaryl. In certain embodiments of the disclosure, each $R_3$ is independently selected from halogen, $C_1$-$C_6$ alkoxy, and cyclopropylethynyl. In certain embodiments of the disclosure, the compounds as otherwise described herein are those wherein each $R_3$ is independently halogen.

In some embodiments, the compounds of formula (I) as otherwise described herein are those wherein m is 2, n is 1, p is 0, and ring A represents 2-chlorophenyl. Such compounds are of formula (I-8), (I-9), or (I-10):

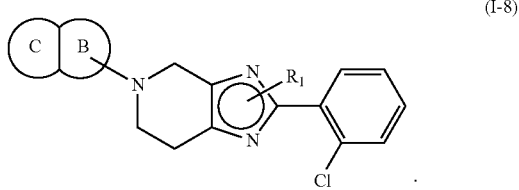

(I-8)

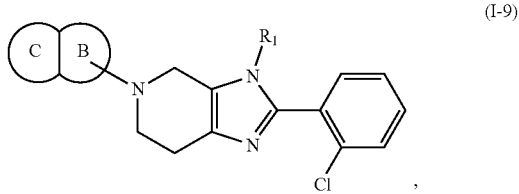

(I-9)

(I-10)

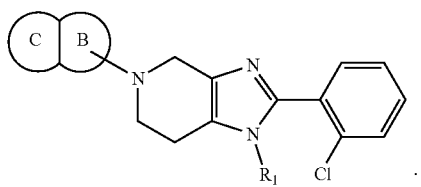

Another embodiment of the disclosure provides compounds of formula (I)-(I-10) as otherwise described herein where ring B and ring C form 1,2,3,4-tetrahydronaphthalenyl, chromanyl, 1,2,3,4-tetrahydroquinolinyl, 1,2,3,4-tetrahydroisoquinolinyl, 2,3-dihydro-1H-indenyl, 2,3-dihydrobenzofuranyl, indolinyl, 1,2,3,4-tetrahydroquinolinyl, or 1,2,3,4-tetrahydroisoquinolinyl, each optionally substituted with one or more $R_4$. In some embodiments of the disclosure, ring B and ring C form 1,2,3,4-tetrahydronaphthalenyl, chromanyl, 1,2,3,4-tetrahydroquinolinyl, or 1,2,3,4-tetrahydroisoquinolinyl, each optionally substituted with one or more $R_4$. In some other embodiments of the disclosure, ring B and ring C form 1,2,3,4-tetrahydronaphthalenyl, 1,2,3,4-tetrahydroquinolinyl, or 1,2,3,4-tetrahydroisoquinolinyl, each optionally substituted with one or more $R_4$. In some embodiments of the disclosure, ring B and ring C form 1,2,3,4-tetrahydronaphthalenyl optionally substituted with one or more $R_4$.

In certain embodiments of the disclosure, the compounds as otherwise described herein are those wherein each $R_4$ is independently selected from halogen, —CN, $C_1$-$C_6$ alkyl optionally substituted with one or more $R_5$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_7$, —$SO_2OR_7$, cyclopropylethynyl, aryl optionally substituted with one or more $R_6$, heteroaryl optionally substituted with one or more $R_6$, heterocyclyl optionally substituted with one or more $R_6$, $C_3$-$C_8$ cycloalkyl optionally substituted with one or more $R_6$, aryloxy optionally substituted with one or more $R_6$, heteroaryloxy optionally substituted with one or more $R_6$, heterocyclyloxy optionally substituted with one or more $R_6$, cycloalkyloxy optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O. In certain embodiments of the disclosure, each $R_4$ is independently selected from halogen, —CN, $C_1$-$C_6$ alkyl optionally substituted with one or more $R_5$, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy ($C_1$-$C_6$ alkoxy), alkoxy($C_1$-$C_6$ alkyl), alkoxy($C_1$-$C_6$ alkoxy), —$SO_2R_7$, cyclopropylethynyl, heteroaryl optionally substituted with one or more $R_6$, heterocyclyl optionally substituted with one or more $R_6$, $C_3$-$C_8$ cycloalkyl optionally substituted with one or more $R_6$, heteroaryloxy optionally substituted with one or more $R_6$, heterocyclyloxy optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O. In certain embodiments of the disclosure, each $R_4$ is independently selected from halogen, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy ($C_1$-$C_6$ alkoxy), —$SO_2R_7$, cyclopropylethynyl, heteroaryl optionally substituted with one or more $R_6$, heterocyclyl optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O. In certain embodiments of the disclosure, each $R_4$ is independently selected from halogen, $C_1$-$C_6$ alkyl, $C_1$-$C_6$ haloalkyl, —OH, $C_1$-$C_6$ alkoxy, $C_1$-$C_6$ haloalkoxy, —$SO_2R_7$, cyclopropylethynyl, oxetanyl, imidazolyl optionally substituted with $R_6$, and cyclopropyl. In certain embodiments of the disclosure, each $R_4$ is independently selected from halogen, $C_1$-$C_6$ alkyl, —OH, $C_1$-$C_6$ alkoxy, —$SO_2R_7$, cyclopropylethynyl, oxetanyl, imidazolyl optionally substituted with $R_6$, and cyclopropyl. In some embodiments of the disclosure, each $R_4$ is independently selected from halogen, $C_1$-$C_6$ alkyl, —OH, $C_1$-$C_6$ alkoxy, cyclopropylethynyl, oxetanyl, imidazolyl optionally substituted with methyl, and cyclopropyl. In certain embodiments of the disclosure, each $R_4$ is independently selected from halogen, —OH, and $C_1$-$C_6$ alkoxy. In some embodiments of the disclosure, each $R_4$ is independently selected from halogen, methyl, —OH, methoxy, cyclopropylethynyl, oxetanyl, imidazolyl optionally substituted with methyl, and cyclopropyl. In certain embodiments of the disclosure, each $R_4$ is independently selected from halogen, methyl, —OH, and methoxy. In certain embodiments of the disclosure, the compounds as otherwise described herein are those wherein each $R_4$ is independently halogen. In certain embodiments of the disclosure, the compounds as otherwise described herein are those wherein each $R_4$ is independently chloro or fluoro. In certain embodiments of the disclosure, the compounds as otherwise described herein are those wherein each $R_4$ is independently chloro.

Another aspect of the disclosure provides compounds of formula (II) as provided above.

In some embodiments, the compounds of formula (II) as otherwise described herein are those wherein t is 1, e.g., the compounds of formula (II-1):

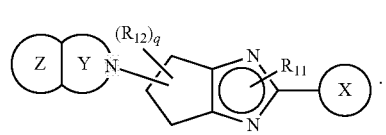

(II-1)

In some embodiments, the compounds of formula (II) as otherwise described herein are those wherein t is 2. Such compounds are of formula (II-2):

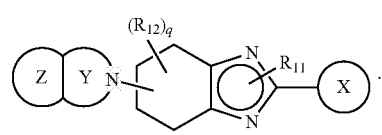

(II-2)

In one embodiment, the disclosure provides compounds of formula (II-2) as otherwise described herein that are of formula (II-3):

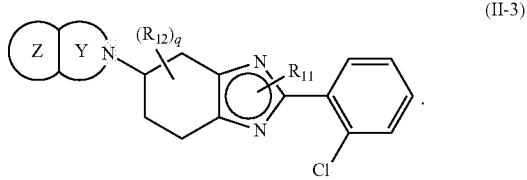

(II-3)

One of skill in the art recognizes that the compounds of formula (II-3) exist in different tautomeric forms, e.g., isomer form (II-4) and (II-5) shown below. Thus, in some embodiments, the compounds of formula (II) as otherwise described herein are of isomer form (II-4):

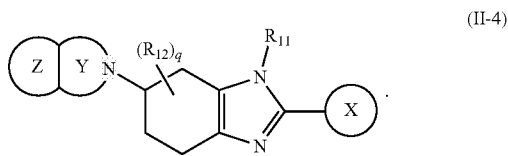

(II-4)

In some embodiments, the compounds of formula (II) as otherwise described herein are those of isomer form (II-5).

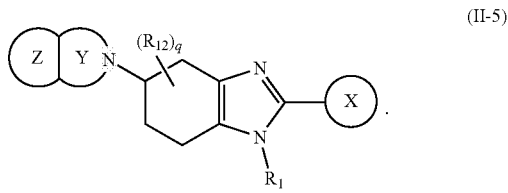

(II-5)

Another embodiment of the disclosure provides compounds of formula (II)-(II-5) as otherwise described herein where q is 0.

In certain embodiments of the disclosure, the compounds of formula (II)-(II-5) as otherwise described herein are those wherein q is 1 or 2. In one embodiment, q is 1. In another embodiment q is 2. In one embodiment, the disclosure provides compounds as otherwise described herein where $R_{12}$ is $C_1$-$C_3$ alkyl. In another embodiment, $R_{12}$ is ethyl or methyl. In another embodiment, $R_{12}$ is methyl.

Another embodiment of the disclosure provides compounds of formula (II)-(II-5) as otherwise described herein where $R_{11}$ is selected from hydrogen, $C_1$-$C_3$ alkyl, $C_1$-$C_3$ haloalkyl, $C_3$-$C_6$ cycloalkyl, heterocyclyl, hydroxy($C_1$-$C_3$ alkyl), alkoxy($C_1$-$C_3$ alkyl), —OH, and oxetanyl. Yet another embodiment of the disclosure provides compounds of formula (II)-(II-5) as otherwise described herein where $R_{11}$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), —OH, and oxetanyl. In certain embodiments of the disclosure, $R_{11}$ is hydrogen or $C_1$-$C_6$ alkyl. In certain embodiments of the disclosure, $R_{11}$ is hydrogen or $C_1$-$C_4$ alkyl. In certain embodiments of the disclosure, $R_{11}$ is hydrogen or $C_1$-$C_3$ alkyl. In certain embodiments of the disclosure, $R_{11}$ is hydrogen, methyl, or ethyl. In certain embodiments of the disclosure, $R_{11}$ is hydrogen or methyl. In certain embodiments of the disclosure, $R_{11}$ is hydrogen. In certain embodiments of the disclosure, $R_{11}$ is methyl. In certain embodiments of the disclosure, $R_{11}$ is hydrogen, methyl, trifluoroethyl, hydroxyethyl, —OH, and oxetanyl. In certain embodiments of the disclosure, $R_{11}$ is hydrogen, $C_1$-$C_3$ alkyl, $C_1$-$C_3$ haloalkyl, hydroxy($C_1$-$C_3$ alkyl), —OH, and oxetanyl.

One embodiment of the disclosure provides compounds of formula (II)-(II-5) as otherwise described herein where ring X represents an aryl optionally substituted with one or more $R_{13}$ or heteroaryl optionally substituted with one or more $R_{13}$.

In certain embodiments of the disclosure, the compounds of formula (II)-(II-5) as otherwise described herein are those where ring X represents phenyl optionally substituted with one or more $R_{13}$ or 6-membered heteroaryl optionally substituted with one or more $R_{13}$.

One embodiment of the disclosure provides compounds of formula (II)-(II-5) as otherwise described herein where ring X represents phenyl optionally substituted with one or more $R_{13}$ or pyridinyl optionally substituted with one or more $R_{13}$.

In certain embodiments of the disclosure, the compounds of formula (II)-(II-5) as otherwise described herein are those where ring X represents phenyl optionally substituted with one or more $R_{13}$. In certain embodiments of the disclosure, ring X represents phenyl substituted with one or more $R_{13}$. In certain embodiments of the disclosure, ring X represents phenyl optionally substituted with one $R_{13}$.

One embodiment of the disclosure provides compounds of formula (II)-(II-5) as otherwise described herein where ring X represents phenyl substituted with one $R_{13}$.

One embodiment of the disclosure provides compounds of formula (II)-(II-5) as otherwise described herein where ring X represents phenyl substituted with halogen (e.g., chloro or fluoro).

One embodiment of the disclosure provides compounds of formula (II)-(II-5) as otherwise described herein where ring X represents 2-chlorophenyl.

Another embodiment of the disclosure provides compounds of formula (II)-(II-5) as otherwise described herein where ring X represents phenyl (i.e., unsubstituted phenyl).

In certain embodiments of the disclosure, the compounds as otherwise described herein are those wherein each $R_{13}$ is independently selected from halogen, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy ($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, cyclopropylethynyl, aryl optionally substituted with one or more $R_{16}$, heteroaryl optionally substituted with one or more $R_{16}$, heterocyclyl optionally substituted with one or more $R_{16}$, and $C_3$-$C_8$ cycloalkyl optionally substituted with one or more $R_{16}$. In certain embodiments of the disclosure, each $R_{13}$ is independently selected from halogen, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy ($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, cyclopropylethynyl, aryl, heteroaryl, heterocyclyl, and $C_3$-$C_8$ cycloalkyl. In certain embodiments of the disclosure, each $R_{13}$ is independently selected from halogen, $C_1$-$C_6$ alkyl optionally substituted with one or more $R_{15}$, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino ($C_1$-$C_6$ alkyl), —SO$_2$R$_{17}$, cyclopropylethynyl, aryl, heteroaryl, heterocyclyl, and $C_3$-$C_8$ cycloalkyl. In certain embodiments of the disclosure, each $R_{13}$ is independently selected from halogen, $C_1$-$C_6$ alkyl optionally substituted with one or more $R_{15}$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$SO_2R_{17}$, cyclopropylethynyl, aryl, heteroaryl, heterocyclyl, and $C_3$-$C_8$ cycloalkyl. In certain embodiments of the disclosure, each $R_{13}$ is independently selected from halogen, $C_1$-$C_6$ alkyl optionally substituted with one or more $R_{15}$, $C_1$-$C_6$ haloalkyl, —OH, $C_1$-$C_6$ alkoxy, $C_1$-$C_6$ haloalkoxy, —$SO_2R_{17}$, cyclopropylethynyl, and heteroaryl. In certain embodiments of the disclosure, each $R_{13}$ is independently selected from halogen, $C_1$-$C_6$ alkoxy, —$SO_2R_{17}$, cyclopropylethynyl, and heteroaryl. In certain embodiments of the disclosure, each $R_{13}$ is independently selected from halogen, $C_1$-$C_6$ alkoxy, cyclopropylethynyl, and heteroaryl. In certain embodiments of the disclosure, each $R_{13}$ is independently selected from halogen, $C_1$-$C_6$ alkoxy, and cyclopropylethynyl. In certain embodiments of the disclosure, the compounds as otherwise described herein are those wherein each $R_{13}$ is independently halogen.

In some embodiments, the compounds of formula (II) as otherwise described herein are those wherein t is 2, q is 0, and ring X represents 2-chlorophenyl. In certain embodiments, such compounds are of formula (II-5), (II-6), or (II-7):

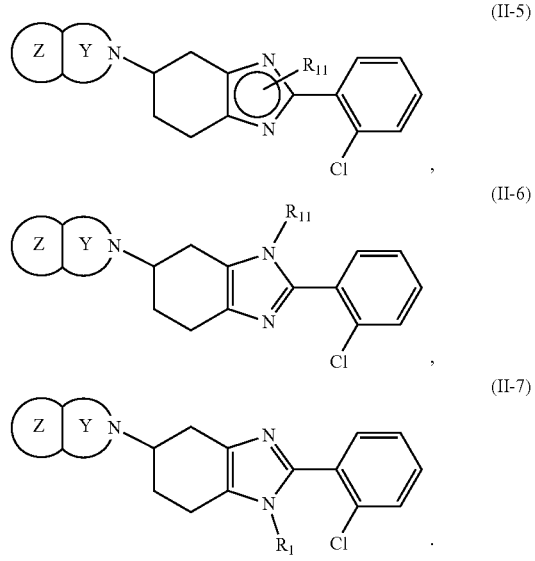

Another embodiment of the disclosure provides compounds of formula (II)-(II-7) as otherwise described herein where ring Y and ring Z form isoindolin-2-yl, 3,4-dihydroisoquinolin-2(1H)-yl, 3,4-dihydroquinolin-1(2H)-yl, benzo[2,3]morpholin-4-yl, 5,7-dihydro-6H-pyrrolo[3,4-b]pyridine-6-yl, 1,3-dihydro-2H-pyrrolo[3,4-c]pyridin-2-yl, 5,7-dihydro-6H-pyrrolo[3,4-b]pyrazine-6-yl, 5,7-dihydro-6H-pyrrolo[3,4-d]pyrimidin-6-yl, 5,6,7,8-tetrahydro-1,7-naphthyridin-7-yl, 5,6,7,8-tetrahydropyrido[3,4-b]pyrazine-6-yl, 5,6,7,8-tetrahydroimidazo[1,2-a]pyrazin-7-yl, or 3,4,6,7-tetrahydro-5H-imidazo[4,5-c]pyridin-5-yl, each optionally substituted with one or more $R_{14}$. In certain embodiments of the disclosure, the compounds as otherwise described herein are those wherein ring Y and ring Z form isoindolin-2-yl, 3,4-dihydroisoquinolin-2(1H)-yl, 3,4-dihydroquinolin-1(2H)-yl, 5,6,7,8-tetrahydro-1,7-naphthyridin-7-yl, 5,6,7,8-tetrahydropyrido[3,4-b]pyrazine-6-yl, 5,6,7,8-tetrahydroimidazo[1,2-a]pyrazin-7-yl, or 3,4,6,7-tetrahydro-5H-imidazo[4,5-c]pyridin-5-yl, each optionally substituted with one or more $R_{14}$. In certain embodiments of the disclosure, the compounds as otherwise described herein are those wherein ring Y and ring Z form isoindolin-2-yl, 3,4-dihydroisoquinolin-2(1H)-yl, or 3,4-dihydroquinolin-1(2H)-yl, each optionally substituted with one or more $R_{14}$. In certain embodiments of the disclosure, ring Y and ring Z form isoindolin-2-yl optionally substituted with one or more $R_{14}$. In certain embodiments of the disclosure, ring Y and ring Z are unsubstituted.

In certain embodiments of the disclosure, the compounds as otherwise described herein are those wherein each $R_{14}$ is independently selected from halogen, —CN, $C_1$-$C_6$ alkyl optionally substituted with one or more $R_{15}$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_{17}$, —$SO_2OR_{17}$, cyclopropylethynyl, aryl optionally substituted with one or more $R_{16}$, heteroaryl optionally substituted with one or more $R_{16}$, heterocyclyl optionally substituted with one or more $R_{16}$, $C_3$-$C_8$ cycloalkyl optionally substituted with one or more $R_{16}$, aryloxy optionally substituted with one or more $R_{16}$, heteroaryloxy optionally substituted with one or more $R_{16}$, heterocyclyloxy optionally substituted with one or more $R_{16}$, cycloalkyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O. In certain embodiments of the disclosure, each $R_{14}$ is independently selected from halogen, —CN, $C_1$-$C_6$ alkyl optionally substituted with one or more $R_{15}$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —$SO_2R_{17}$, cyclopropylethynyl, heteroaryl optionally substituted with one or more $R_{16}$, heterocyclyl optionally substituted with one or more $R_{16}$, $C_3$-$C_8$ cycloalkyl optionally substituted with one or more $R_{16}$, heteroaryloxy optionally substituted with one or more $R_{16}$, heterocyclyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O. In certain embodiments of the disclosure, each $R_{14}$ is independently selected from halogen, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —$SO_2R_{17}$, cyclopropylethynyl, heteroaryl optionally substituted with one or more $R_{16}$, heterocyclyl optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O. In certain embodiments of the disclosure, each $R_{14}$ is independently selected from halogen, $C_1$-$C_6$ alkyl, $C_1$-$C_6$ haloalkyl, —OH, $C_1$-$C_6$ alkoxy, $C_1$-$C_6$ haloalkoxy, —$SO_2R_{17}$, cyclopropylethynyl, oxetanyl, imidazolyl optionally substituted with $R_{16}$, and cyclopropyl. In certain embodiments of the disclosure, each $R_{14}$ is independently selected from halogen, $C_1$-$C_6$ alkyl, —OH, $C_1$-$C_6$ alkoxy, —$SO_2R_{17}$, cyclopropylethynyl, oxetanyl, imidazolyl optionally substituted with $R_{16}$, and cyclopropyl. In some embodiments of the disclosure, each $R_{14}$ is independently selected from halogen, $C_1$-$C_6$ alkyl, —OH, $C_1$-$C_6$ alkoxy, cyclopropylethynyl, oxetanyl, imidazolyl optionally substituted with methyl, and cyclopropyl. In certain embodiments of the disclosure, each $R_{14}$ is independently selected from halogen, —OH, and $C_1$-$C_6$ alkoxy. In certain embodiments of the disclosure, each $R_{14}$ is independently selected from halogen, methyl, —OH, methoxy, cyclopropylethynyl, oxetanyl, imidazolyl optionally substituted with methyl, and cyclopropyl. In certain embodiments of the disclosure, each $R_{14}$ is independently selected from halogen, methyl, —OH, and methoxy. In certain embodiments of the disclosure, the compounds as otherwise described herein are those wherein each $R_{14}$ is independently halogen. In certain embodiments of the disclosure, the compounds as otherwise described herein are those wherein each $R_{14}$ is independently chloro or fluoro. In certain embodiments of the disclosure, the compounds as otherwise described herein are those wherein each $R_{14}$ is independently chloro.

Therapeutics Applications

There is a great need in the art to develop novel therapeutics for the treatment of neurological disorders characterized by myelin loss or myelin deficiency. The present disclosure satisfies this and other needs by providing a novel method for enhancing remyelination and neuroprotection.

Thus, in one aspect, the disclosure provides a method of inhibiting Gli1. Another aspect of the disclosure provides a method for enhancing remyelination in a subject. In a related aspect, the disclosure provides a method for enhancing neuroprotection of a central nervous system (CNS) or peripheral nervous system (PNS) neuron in a subject. Such methods include administering to a subject in need of such treatment an effective amount of one or more compounds of the disclosure as described herein (i.e., compounds of formula (I) or (II)) or a pharmaceutical composition of the disclosure as described herein. In one embodiment, the subject has a neurological disorder characterized by myelin loss or myelin deficiency.

As used herein, the term "remyelination" refers to the generation of new myelin sheaths. Remyelination can be monitored by methods which include direct determination of the state of myelin in the subject, e.g., one can measure white matter mass using magnetic resonance imaging (MRI), measure the thickness of myelin fibers using a magnetic resonance spectroscopy (MRS) brain scan, or any other direct measures known in the art (e.g., Positron-Emission Tomography (PET), Diffusion-Weighted Imaging (DW-1, or DW-MRI), Diffusion Tensor Imaging, Magnetization Transfer, etc.). Treatment effectiveness can be also monitored by improvements in physiological parameters (such as visual evoked response (VER), brainstem auditory evoked response (BAER), and somatosensory evoked potential (SSEP)) and a positive change in neuropsychology (e.g., the status of various abilities such as memory, arithmetic, attention, judgment and reasoning). Certain tests for color blindness can also be helpful in tracking the treatment of demyelinating disorders on the eyes. Whitaker et al. (1995) *Ann. Neurol.* 38(4):635-632.

The disclosure also provides methods of treating a neurological disorder. Such method includes administering to a subject in need of such treatment an effective amount of one or more compounds of the disclosure as described herein (i.e., compounds of formula (I) or (II)) or a pharmaceutical composition of the disclosure as described herein. In one embodiment, the neurological disorder is characterized by myelin loss or myelin deficiency.

As used herein, the term "neurological disorder characterized by myelin loss or myelin deficiency" encompasses any disease associated with the destruction or removal of myelin, the fatty sheath surrounding and insulating nerve fibers, from nerves. Non-limiting examples of such disorders include, but are not limited to, multiple sclerosis (MS) (e.g., relapsing/remitting multiple sclerosis, secondary progressive multiple sclerosis, progressive relapsing multiple sclerosis, primary progressive multiple sclerosis, and acute fulminant multiple sclerosis), central pontine myelinolysis, acute disseminated encephalomyelitis, progressive multifocal leukoencephalopathy, subacute sclerosing panencephalitis, post-infectious encephalomyelitis, chronic inflammatory demyelinating polyneuropathy, Devic's disease, Balo's concentric sclerosis, the leukodystrophies (e.g., metachromatic leukodystrophy, Krabbe disease, adrenoleukodystrophy, Pelizaeus-Merzbacher disease, Canavan disease, childhood ataxia with central hypomyelination, Alexander disease, or refsum disease), optic neuritis, transverse myelitis, cerebral palsy, spinal cord injury, age-associated myelin deficiency, Alzheimer's Disease, as well as acquired and inherited neuropathies in the peripheral nervous system (e.g., Guillain-Barre syndrome and Charcot Marie Tooth disease).

In certain embodiments of this aspect, the neurological disorder is selected from multiple sclerosis, central pontine myelinolysis, acute disseminated encephalomyelitis, progressive multifocal leukoencephalopathy, subacute sclerosing panencephalitis, post-infectious encephalomyelitis, chronic inflammatory demyelinating polyneuropathy, Devic's disease, Balo's concentric sclerosis, the leukodystrophies, optic neuritis, transverse myelitis, cerebral palsy, spinal cord injury, age-associated myelin deficiency, Alzheimer's Disease, and acquired and inherited neuropathies in the peripheral nervous system. In certain embodiments of this aspect, the neurological disorder is multiple sclerosis. In certain embodiments of this aspect, the neurological disorder is Alzheimer's Disease.

The disclosure also provides methods of treating a non-CNS disease. Such method includes administering to a subject in need of such treatment an effective amount of one or more compounds of the disclosure as described herein (i.e., compounds of formula (I) or (II)) or a pharmaceutical composition of the disclosure as described herein.

In certain embodiments, the non-CNS disease is cancer. Many different cancers can be treated with compounds and compositions of the disclosure. In certain embodiments, the cancer is breast cancer, pancreatic cancer, colon cancer, lung cancer, rhabdomyosarcoma, basal-cell carcinoma, glioblastoma, medulloblastoma, leukemia, prostate cancer, skin cancer, lymphoma, esophageal cancer, ovarian cancer, thyroid cancer, osteosarcoma, liver cancer, multiple endocrine neoplasia, gastrointestinal cancer, or mesothelioma.

In some embodiments, a particularly suitable cancer is a solid tumor. Examples of solid tumors include, but are not limited to, carcinomas, sarcomas, and astrocytomas. In certain embodiments, the cancer is breast cancer, prostate cancer, lung cancer (e.g., small-cell lung carcinoma (SCLC) and non-small-cell lung carcinoma (NSCLC)), gastric cancer, colorectal cancer, cervical cancer, endometrial cancer, ovarian cancer, skin cancer (e.g., basal-cell skin cancer (BCC), squamous-cell skin cancer (SCC), and melanoma), pancreatic cancer, kidney cancer, adrenal gland cancer, sarcoma, thyroid cancer, cholangiocarcinoma, glioblastoma, astrocytoma, oligodendroglioma, high-grade glioma, malignant glioma, glioma, neuroblastoma, medulloblastoma, leukemia or lymphoma. Suitable cancers also include a hematological malignancy, such as leukemia or lymphoma. In certain embodiments, the cancer is acute myeloid leukemia (AML), chronic myeloid leukemia (CML), acute lymphoblastic leukemia (ALL), chronic lymphocytic leukemia (CLL), or lymphoma.

In certain embodiments, the cancer is characterized by elevated Gli1. In certain embodiments, compounds and compositions of the invention are used to treat a cancer that is characterized by elevated Gli1. In certain embodiments, the cancer with elevated Gli1 is breast cancer, pancreatic cancer, colon cancer, lung cancer, rhabdomyosarcoma, leukemia, basal-cell carcinoma, glioblastoma, medulloblastoma, prostate cancer, skin cancer, lymphoma, esophageal cancer, ovarian cancer, thyroid cancer, osteosarcoma, liver cancer, multiple endocrine neoplasia, gastrointestinal cancer, or mesothelioma.

In certain embodiments, the non-CNS disease is cystic kidney disease, chronic liver disease, Hepatitis, C, obstructive pulmonary disease, organ fibrosis (including, e.g., kidney fibrosis, cardiac fibrosis, and pulmonary fibrosis), or rheumatoid arthritis.

In some embodiments of the methods of the disclosure, at least a 5% (e.g., at least 10%, at least 15%, at least 20%, at least 25%, at least 30%, at least 35%, at least 40%, at least 50%, at least 60%, at least 70%) improvement in one or more symptoms of the disease or disorder of the disclosure as described herein is sufficient to classify the subject as responding to the method of treatment.

The compounds and compositions of the disclosure as described herein may also be administered in combination with one or more secondary therapeutic agents. Thus, in certain embodiment, the method also includes administering to a subject in need of such treatment an effective amount of one or more compounds of the disclosure as described herein (i.e., compounds of formula (I) or (II)) or a pharmaceutical composition of the disclosure as described herein and one or more secondary therapeutic agents.

In certain embodiments, the secondary therapeutic agent is a Gli 1 inhibitor. Examples of the Gli1 inhibitors suitable for use as secondary agents include, but are not limited to, GANT61, GANT58, genistein, epigallocatechin gallate (EGCG), zerumbone, zerumbone epoxide, staurosporinone, 6-hydroxystaurosporinone, arcyriaflavin C, 5,6-dihydroxyarcyriaflavin A, physalin F, physalin B, NMDA298-1, JK184, HPI-1, HPI-4, HPI-3, HPI-4, arsenic trioxide, polyunsaturated fatty acid (such as arachidonic acid), or a siRNA (e.g., siRNA having the sequence selected from the group consisting of GUCAUUAUCAAAUUUCUCCTT (SEQ ID NO: 1); AGAAGAAAAGAGUGGGCCCTT (SEQ ID NO: 2); UCCGGUGUUUUCUUCAUCCTT (SEQ ID NO: 3); GAGAU CUUCC CUUCA UACCTT (SEQ ID NO: 4), and AACUCCACAGGCAUACAGGAU (SEQ ID NO: 5)). In certain embodiments, the secondary therapeutic agent may be a Gli1-binding protein such as kinesin-like protein KIF7, together with serine/threonine-protein kinase (STK3649) or ZIC1. In certain embodiments, the secondary therapeutic agent may be an inhibitor for a different pathway or molecular target, such as BEZ235 (PI3K/mTOR dual inhibitor), LY294002 (PI3K inhibitor) or U0126 (MEK1/2 inhibitor). In certain embodiments, the secondary therapeutic agent may be any one of those described in *Lung Cancer: Targets and Therapy* (2018) 9: 35-43 (incorporated by reference herein).

In certain embodiments, the secondary therapeutic agent is an agent that facilitates brain delivery. Non-limiting examples of such agents include, e.g., an implantable reservoir (Omaya reservoir), functionalized nanocarriers (e.g., nanoparticles coated with transferrin or transferrin receptor [TR] antibodies) and liposomes (e.g., liposomes coated with targeting molecules such as antibodies, Trojan Horses Liposomes [TELL]), antibodies (e.g., antibodies against transferrin receptor [TR] and insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, etc.

In certain embodiments, the secondary therapeutic agent is an agent that limits demyelination or enhances remyelination. Some examples include, but are not limited to, Interferon Beta I a (Avonex), Interferon Beta Ib (Rebif), glatiramer acetate (Copaxone), mitoxantrone (Novantrone), azathiprine (Imuran), cyclophosphamide (Cytoxan or Neosar), cyclosporine (Sandimmune), ampyra, dimethyl fumarate (BG12), fmgolimod, methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), Corticotropin (Acthar), anti-integrin specific antibodies, Cytoxan, naltrexone, and the like. Other examples include anti-muscarinic agents, anti-LINGO therapies, axin/Wnt pathway inhibitors, and agonists for RXR transcription factors (such as 9-cis-retinoic acid).

In certain embodiments, the secondary therapeutic agent is an agent that causes upregulation and/or increases activity of Gli2 and/or Gli3. Some examples include, but are not limited to, Shh agonists and Protein Kinase A inhibitors (PKA inhibitors). Specific examples of useful Shh agonists and PKA inhibitors are provided, for example, in U.S. Pat. Nos. 6,767,888 and 6,683,192, incorporated by reference herein. PKA inhibitors may be purchased from commercial sources, such as Enzo Life Sciences (Farmingdale).

In certain embodiments, the secondary therapeutic agent is an agonist of Smo Examples of useful Smo agonists include, for example, N-methyl-N'-(3-pyridinylbenzyl)-N'-(3-chlorobenzo[b]thiophene-2-carbonyl)-1,4-diaminocyclohexane (SAG), and those disclosed in International Patent Publication WO 2003/027234, PNAS (2002) 99(22):14071-14076, and/or *Journal of Biology* (2002) 1:10 (all incorporated by reference herein). In some embodiments, agonists of Smo cause upregulation and/or activity of Gli2 and/or Gli3. In some embodiments, agonists of Smo limit demyelination or enhance remyelination.

In certain embodiments, the secondary therapeutic agent is an antagonist of Smo. Non-limiting examples of Smo antagonists include, for example, cyclopamine, derivatives of cyclopamine, sonidegib, derivatives of sonidegib, vismodegib, and derivatives of vismodegib, and those described in *Future Medicinal Chemistry* (2019)11(6): 489-638 (incorporated by reference herein). In some embodiments, antagonists of Smo can be used to treat cancer.

In certain embodiments, the secondary therapeutic agent maybe a gene editing agent. Suitable examples of gene editing agents include, but are not limited to, CRISPR (e.g., an RNA guide strand with an endonuclease that may be, but is not limited to a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, CasX or CasY), zinc finger nucleases (ZFNs), transcription activator-like effector nucleases (TALENs), a NgAgo-based system, and meganucleases.

In certain embodiments, the secondary therapeutic agent is an anti-proliferative agent. Examples of suitable secondary therapeutic agents include, but are not limited to, temozolomide, camptothecin, doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, chloroquine, hydroxychloroquine, autophagy inhibitors, and abt-737.

When administered as a combination, the compounds and compositions of the disclosure as described herein and the secondary therapeutic agents can be formulated as separate compositions that are given simultaneously or sequentially, or the therapeutic agents can be given as a single composition. In certain embodiments, the secondary therapeutic agent may be administered in an amount below its established half maximal inhibitory concentration ($IC_{50}$). For example, the secondary therapeutic agent may be administered in an amount less than 1% of, e.g., less than 10%, or less than 25%, or less than 50%, or less than 75%, or even less than 90% of the inhibitory concentration ($IC_{50}$).

Pharmaceutical Compositions

In another aspect, the present disclosure provides compositions comprising one or more of compounds as described above with respect to formula (I)-(II) and an appropriate carrier, solvent, adjuvant, or diluent. The exact nature of the carrier, solvent, adjuvant, or diluent will depend upon the desired use for the composition, and may range from being suitable or acceptable for veterinary uses to being suitable or acceptable for human use. The composition may optionally include one or more secondary therapeutic agents. In certain embodiments, the composition may include one or more secondary anticancer therapeutic agents.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Definitions

The following terms and expressions used herein have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, and —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thioxo.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thioxo. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thioxo.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thioxo. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, 2,3-dihydrothieno[3,4-b][1,4]dioxan-5-yl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thioxo.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two, or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thioxo. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thioxo.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thioxo" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, ameliorating, or slowing progression of one or more symptoms of the disease or disorder.

In certain embodiments, treating as used herein includes inhibiting a disease or disorder. In certain embodiments, treating as used herein includes inhibiting, relieving, ameliorating, or slowing progression of one or more symptoms of the disease or disorder.

"Subject" refers to a warm blooded animal such as a mammal, preferably a human, or a human child, which is afflicted with, or has the potential to be afflicted with one or more diseases and disorders described herein.

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Ed., Wiley-Interscience, 2001; or Vogel, A Textbook of Practical Organic Chemistry, Including Qualitative Organic Analysis, Fourth Ed., New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) or (II) can be prepared according to general procedures (below), and/or analogous synthetic procedures. One of skill in the art can adapt the reaction sequences of Examples 1-213 and general procedures to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

EXAMPLES

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Example 1: 5-(8-chloro-1,2,3,4-tetrahydronaphthalen-2-yl)-2-(2-chlorophenyl)-4,5,6,7-tetrahydro-3H-imidazo[4,5-c]pyridine

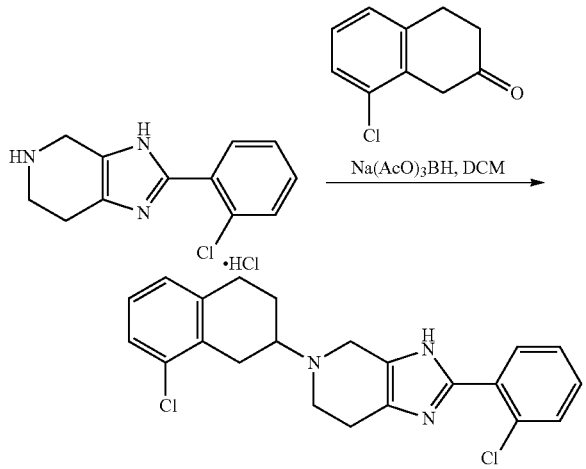

The mixture of 2-(2-chlorophenyl)-4,5,6,7-tetrahydro-3H-imidazo[4,5-c]pyridine hydrochloride (270 mg, 1 mmol), 8-chloro-3,4-dihydronaphthalen-2(1H)-one (271 mg, 1.5 mmol) and Na(AcO)$_3$BH (424 mg, 2 mmol) in dichloromethane (5 mL) was stirred at room temperature for 16 hrs. The resulting mixture was evaporated under vacuum and then purified by preparative HPLC (prep-HPLC) (15% to % to 35% acetonitrile in water (0.1% trifluoroacetic acid). This resulted in 5-(8-chloro-1,2,3,4-tetrahydronaphthalen-2-yl)-2-(2-chlorophenyl)-4,5,6,7-tetrahydro-3H-imidazo[4,5-c]pyridine, trifluoroacetic acid salt (46 mg, 9%) as a white solid. MS (ESI): mass calcd. for $C_{22}H_{21}Cl_2N_3$ 398.33, m/z found 397.8 [M+H]⁺. ¹H NMR (400 MHz, CD₃OD) δ ppm 7.76 (d, J=7.6 Hz, 1H), 7.67 (d, J=7.6 Hz, 1H), 7.62-7.52 (m, 2H), 7.32 (d, J=7.6 Hz, 1H), 7.24-7.16 (m, 2H), 4.73-4.60 (m, 2H), 3.99-3.96 (m, 2H), 3.85 (t, J=6.0 Hz, 1H), 3.55-3.50 (m, 1H), 3.26 (s, 2H), 3.09-3.02 (m, 3H), 2.50 (d, J=10.0 Hz, 1H), 2.10-2.00 (m, 1H).

The racemate was purified by Prep-Chiral-SFC (Column: Chiralpak-AD, Solvent: methanol (DEA), % Modifier: 30%) then purified by prep-HPLC each. This resulted Example 1-R: (R)-5-(8-chloro-1,2,3,4-tetrahydronaphthalen-2-yl)-2-(2-chlorophenyl)-4,5,6,7-tetrahydro-3H-imidazo[4,5-c] pyridine (assumed) (5 mg, 20%) as a white solid (MS (ESI): mass calcd. for C₂₀H₁₉Cl₂N₃O 388.29, m/z found 387.8 [M+H]⁺. Chiral HPLC (CS30-FR12.5.met, Rt=9.2 min). ¹H NMR (400 MHz, CD₃OD) δ ppm 7.76 (d, J=7.6 Hz, 1H), 7.67 (d, J=7.6 Hz, 1H), 7.62-7.52 (m, 2H), 7.32 (d, J=7.6 Hz, 1H), 7.24-7.16 (m, 2H), 4.73-4.60 (m, 2H), 3.99-3.96 (m, 2H), 3.85 (t, J=6.0 Hz, 1H), 3.55-3.50 (m, 1H), 3.26 (s, 2H), 3.09-3.02 (m, 3H), 2.50 (d, J=10.0 Hz, 1H), 2.10-2.00 (m, 1H)), and Example 1-S: (S)-5-(8-chloro-1,2,3,4-tetrahydronaphthalen-2-yl)-2-(2-chlorophenyl)-4,5,6,7-tetrahydro-3H-imidazo[4,5-c]pyridine (assumed) (5 mg, 20%) as a white solid (MS (ESI): mass calcd. for C₂₀H₁₉Cl₂N₃O 388.29, m/z found 387.8 [M+H]⁺. Chiral HPLC (CS30-FR12.5.met, Rt=13.7 min). ¹H NMR (400 MHz, CD₃OD) δ ppm 7.76 (d, J=7.6 Hz, 1H), 7.67 (d, J=7.6 Hz, 1H), 7.62-7.52 (m, 2H), 7.32 (d, J=7.6 Hz, 1H), 7.24-7.16 (m, 2H), 4.73-4.60 (m, 2H), 3.99-3.96 (m, 2H), 3.85 (t, J=6.0 Hz, 1H), 3.55-3.50 (m, 1H), 3.26 (s, 2H), 3.09-3.02 (m, 3H), 2.50 (d, J=10.0 Hz, 1H), 2.10-2.00 (m, 1H)).

Example 2: 2-(2-chlorophenyl)-5-(2,3-dihydro-1H-inden-2-yl)-4,5,6,7-tetrahydro-3H-imidazo[4,5-c]pyridine

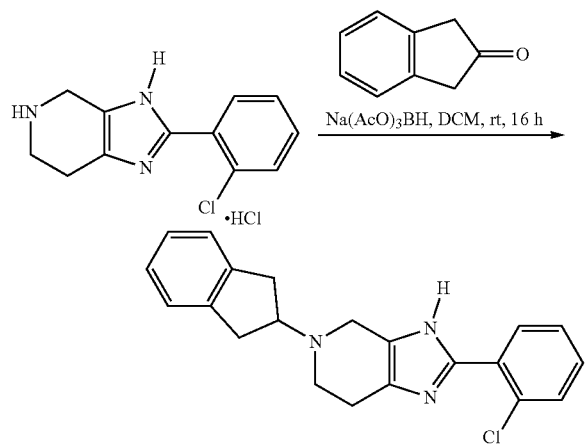

The mixture of 2-(2-chlorophenyl)-4,5,6,7-tetrahydro-3H-imidazo[4,5-c]pyridine hydrochloride (27 mg, 0.1 mmol), 1,3-dihydro-2H-inden-2-one (13 mg, 0.1 mmol) and Na(AcO)₃BH (42 mg, 0.2 mmol) in dichloromethane (0.5 mL) was stirred at room temperature for 16 hrs. The resulting mixture was evaporated under vacuum and then purified by preparative TLC (prep-TLC) (ethyl acetate). This resulted in 2-(2-chlorophenyl)-5-(2,3-dihydro-1H-inden-2-yl)-4,5,6,7-tetrahydro-3H-imidazo[4,5-c]pyridine (5 mg, 14%) as a white solid. MS (ESI): mass calcd. for C₂₁H₂₀ClN₃ 349.86, m/z found 349.8 [M+H]⁺. ¹H NMR (400 MHz, CD₃OD) δ ppm 7.74-7.71 (s, 1H), 7.55-7.53 (m, 1H), 7.43-7.40 (m, 2H), 7.25-7.23 (m, 2H), 7.17-7.15 (m, 2H), 3.80 (s, 2H), 3.63-3.57 (m, 1H), 3.33-3.27 (m, 2H), 3.10-3.02 (m, 4H), 2.89 (t, J=5.6 Hz, 2H).

Example 3: 5-(6-chlorochroman-3-yl)-2-(2-chlorophenyl)-4,5,6,7-tetrahydro-3H-imidazo[4,5-c]pyridine

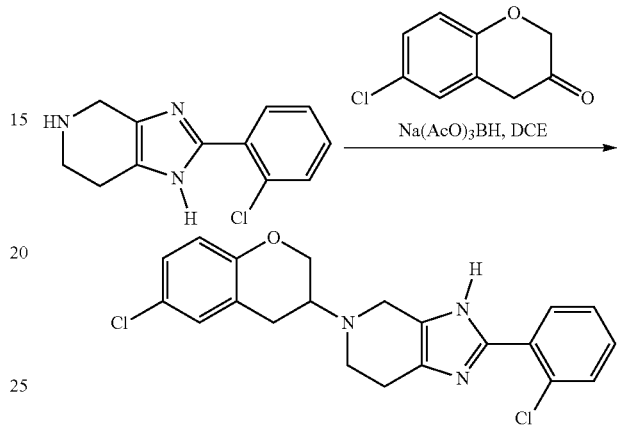

The mixture of 2-(3-chlorophenyl)-4,5,6,7-tetrahydro-3H-imidazo[4,5-c]pyridine (69.9 mg, 0.3 mmol), 7-chloro-3,4-dihydronaphthalen-2(1H)-one (36.4 mg, 0.2 mmol) and Na(AcO)₃BH (84.8 mg, 0.4 mmol) in dichloromethane (2 mL) was stirred at 80° C. for 16 hrs. The resulting mixture was evaporated under vacuum and then purified by Prep-HPLC: 30% to 50% acetonitrile in water (0.1% trifluoroacetic acid). This resulted in 5-(6-chlorochroman-3-yl)-2-(2-chlorophenyl)-4,5,6,7-tetrahydro-3H-imidazo[4,5-c] pyridine, trifluoroacetic acid salt (7 mg, 7%) as a white solid. MS (ESI): mass calcd. for C₂₁H₁₉C₁₂N₃O 400.30, m/z found 399.8 [M+H]⁺. ¹H NMR (400 MHz, CD₃OD) δ ppm 7.74-7.52 (m, 4H), 7.21 (s, 1H), 7.14 (d, J=8.8 Hz, 1H), 6.85 (d, J=8.4 Hz, 1H), 4.47-4.40 (m, 2H), 4.31 (s, 2H), 3.73 (s, 1H), 3.57 (s, 2H), 3.22-3.19 (m, 2H), 3.05 (s, 2H).

Example 4: 5-(7-methoxy-1,2,3,4-tetrahydronaphthalen-2-yl)-2-(3-methoxyphenyl)-4,5,6,7-tetrahydro-3H-imidazo [4,5-c]pyridine

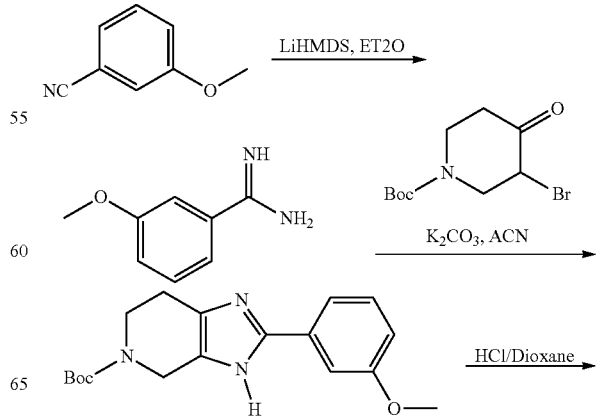

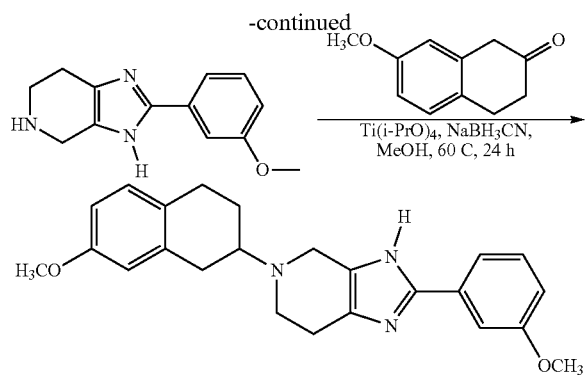

The solution of 3-methoxybenzimidamide (5 g, 38 mmol) in diethyl ether (100 mL) was dropwise added to LiHMDS (1 M in tetrahydrofuran, 76 mL) with stirring under nitrogen atmosphere at 0° C. The resulting solution was stirred at 0° C. to room temperature for 16 hrs. The resulting solution was quenched with 3N hydrochloric acid (100 mL) at 0° C. The water phase was collected, the pH of the water phase was adjusted to 14 with NaOH aqueous, and extracted with ethyl acetate (100 mL×3). The combined organic phases were washed with brine (100 mL), dried over anhydrous $Na_2SO_4$ and evaporated in vacuo. This resulted in 3-methoxybenzimidamide (4 g, 71% yield) as a brown solid. MS (ESI): mass calcd. for $C_8H_{10}N_2O$ 133.05, m/z found 133.8 $[M+H]^+$.

The mixture of 3-methoxybenzimidamide (1.50 g, 10 mmol), tert-butyl 3-bromo-4-oxopiperidine-1-carboxylate (2.78 g, 10 mmol) and potassium carbonate (1.38 g, 10 mmol) in acetonitrile (40 mL) was stirred at 80° C. for 16 hrs. The resulting mixture was evaporated under vacuum and purified by silica column (0 to 50% ethyl acetate in petroleum ether). This resulted in tert-butyl 2-(3-methoxyphenyl)-3,4,6,7-tetrahydro-5H-imidazo[4,5-c]pyridine-5-carboxylate (0.60 g, 18% yield). MS (ESI): mass calcd. for $C_{18}H_{23}N_3O_3$ 329.17, m/z found 329.9 $[M+H]^+$.

The mixture of tert-butyl 2-(3-methoxyphenyl)-3,4,6,7-tetrahydro-5H-imidazo[4,5-c]pyridine-5-carboxylate (600 mg, 1.8 mmol) in HCl (g) in dioxane (4N, 20 mL) was stirred at room temperature for 16 hrs. The resulting mixture was basified by ammonia to free the product, then concentrated to give crude product, which was purified by chromatography on silica gel, eluting (10:1 dichloromethane:methanol) to afford 2-(3-methoxyphenyl)-4,5,6,7-tetrahydro-3H-imidazo[4,5-c]pyridine (300 mg, 72% yield) as a yellow solid. MS (ESI): mass calcd. for $C_{13}H_{15}N_3O$ 229.12, m/z found 230.0 $[M+H]^+$.

To a solution of 2-(3-methoxyphenyl)-4,5,6,7-tetrahydro-3H-imidazo[4,5-c]pyridine (120 mg, 0.52 mmol) and 7-methoxy-3,4-dihydronaphthalen-2(1H)-one (92 mg, 0.52 mmol) in methanol (5 mL) was added Ti(i-PrO)$_4$ (296 mg, 1.04 mmol), the resulting mixture was stirred at room temperature under $N_2$ for 1 h, NaBH$_3$CN (164 mg, 2.60 mmol) was added to the reaction mixture and stirred at 60° C. for 16 hrs. After the reaction was finished, it was quenched with $H_2O$ and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C[18] 150×21.2 mm, 5 μm, mobile phase: acetonitrile-$H_2O$ (0.1% trifluoroacetic acid), gradient: 20-25) to afford 5-(7-methoxy-1,2,3,4-tetrahydronaphthalen-2-yl)-2-(3-methoxyphenyl)-4,5,6,7-tetrahydro-3H-imidazo[4,5-c]pyridine (8 mg, 4% yield) as white solid. MS (ESI): mass calcd. for $C_{24}H_{27}N_3O$ 389.21, m/z found 389.9 $[M+H]^+$, $^1H$ NMR (400 MHz, $CD_3OD$) δ ppm 7.48-7.56 (m, 3H), 7.08-7.20 (m, 2H), 6.78-6.80 (m, 2H), 4.62-4.71 (m, 2H), 3.78-3.96 (m, 6H), 3.79 (s, 3H), 3.21-3.28 (m, 4H), 2.95-3.06 (m, 2H), 2.47-2.49 (m, H), 2.03-2.08 (m, H).

Example 5: 5-(7-fluoro-1,2,3,4-tetrahydronaphthalen-2-yl)-2-(2-fluorophenyl)-4,5,6,7-tetrahydro-3H-imidazo[4,5-c]pyridine

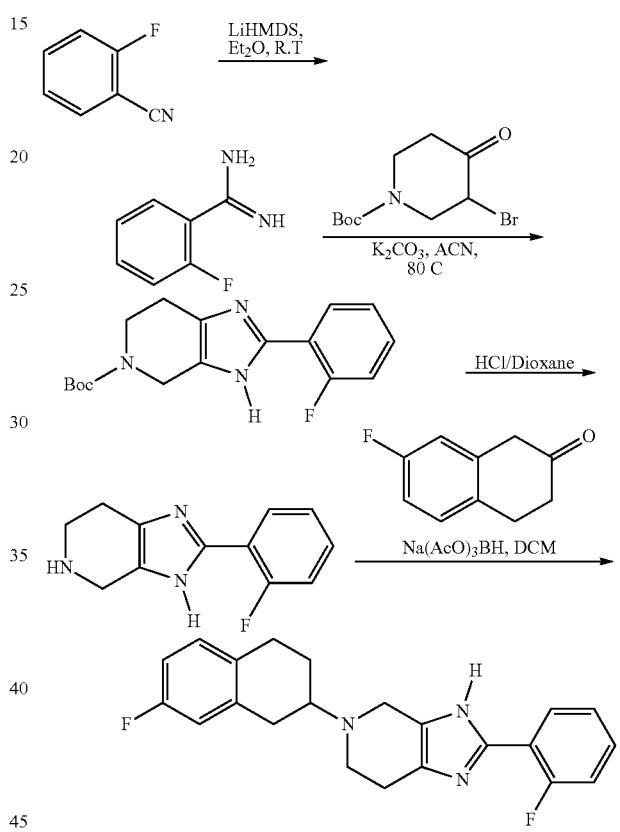

The solution of 2-fluorobenzonitrile (18 g, 148 mmol) in diethyl ether (100 mL) was dropwise added to LiHMDS (1 M in tetrahydrofuran, 300 mL) with stirring under nitrogen atmosphere at 0° C. The resulting solution was stirred at 0° C. to room temperature for 16 hrs. The resulting solution was quenched with 3N hydrochloric acid (300 mL) at 0° C. The water phase was collected, the pH of the water phase was adjusted to 14 with NaOH aqueous, and extracted with ethyl acetate (300 mL×2). The combined organic phases were washed with brine (100 mL), dried over anhydrous $Na_2SO_4$ and evaporated in vacuo. This resulted in 2-fluorobenzimidamide (18 g, 88%) as a brown solid. MS (ESI): mass calcd. for $C_7H_7FN_2$ 138.15, m/z found 138.9 $[M+H]^+$.

The mixture of 2-fluorobenzimidamide (5.5 g, 40 mmol), tert-butyl 3-bromo-4-oxopiperidine-1-carboxylate (11 g, 40 mmol) and potassium carbonate (5.5 g, 40 mmol) in acetonitrile (160 mL) was stirred at 80° C. for 16 hrs. The resulting mixture was evaporated under vacuum and purified by silica column (0 to 50% ethyl acetate in petroleum ether). This resulted in tert-butyl 2-(2-fluorophenyl)-3,4,6,7-tetrahydro- 5H-imidazo[4,5-c]pyridine-5-carboxylate (9 g, crude). MS (ESI): mass calcd. for $C_{17}H_{20}FN_3O_2$ 317.36, m/z found 317.9 [M+H]$^+$.

The mixture of tert-butyl 2-(2-fluorophenyl)-3,4,6,7-tetrahydro-5H-imidazo[4,5-c]pyridine-5-carboxylate (9 g, crude) in HCl (g) in dioxane (4N, 60 mL) was stirred at room temperature for 16 hrs. The solvent was evaporated under vacuum. The residue was dissolved in water (100 mL), washed with ethyl acetate (50 mL×2). The pH of water phase was adjusted to 10 with potassium carbonate, and extracted with ethyl acetate (100 mL×4). The combined organic phases were evaporated under vacuum. This resulted in 2-(2-fluorophenyl)-4,5,6,7-tetrahydro-3H-imidazo[4,5-c]pyridine (5 g, crude) as a yellow oil. When extracted with ethyl acetate again, much solid was generated from ethyl acetate and water. Filtered, the solid was collected. This resulted in 2-(2-fluorophenyl)-4,5,6,7-tetrahydro-3H-imidazo[4,5-c]pyridine as a white solid (2 g, 33%). MS (ESI): mass calcd. for $C_{12}H_{12}FN_3$ 217.25, m/z found 217.9 [M+H]$^+$.

The mixture of 2-(2-fluorophenyl)-4,5,6,7-tetrahydro-3H-imidazo[4,5-c]pyridine (77 mg, 0.35 mmol), 7-fluoro-3,4-dihydronaphthalen-2(1H)-one (56 mg, 0.35 mmol) and Na(AcO)$_3$BH (147 mg, 0.7 mmol) in dichloromethane was stirred at room temperature for 16 hrs. The resulting mixture was evaporated under vacuum and then purified by prep-HPLC: 30% to 70% acetonitrile in water (0.1% trifluoroacetic acid). This resulted in 5-(7-fluoro-1,2,3,4-tetrahydronaphthalen-2-yl)-2-(2-fluorophenyl)-4,5,6,7-tetrahydro-3H-imidazo[4,5-c]pyridine, trifluoroacetic acid salt (20 mg, 12%) as a white solid. MS (ESI): mass calcd. for $C_{22}H_{21}F_2N_3$ 365.43, m/z found 365.8 [M+H]$^+$. $^1$H NMR (400 MHz, CD$_3$OD) δ ppm 7.97 (t, J$_1$=J$_2$=8.0 Hz, 1H), 7.58 (s, 1H), 7.40-7.38 (m, 2H), 7.20 (t, J$_1$=J$_2$=6.0 Hz, 1H), 6.99-6.93 (m, 2H), 4.62-4.60 (m, 2H), 3.97-3.85 (m, 3H), 3.33-2.95 (m, 6H), 2.50-2.48 (m, 1H), 2.12-2.02 (m, 1H).

Example 6: 5-(7-chloro-1,2,3,4-tetrahydronaphthalen-2-yl)-2-(2-fluorophenyl)-4,5,6,7-tetrahydro-3H-imidazo[4,5-c]pyridine

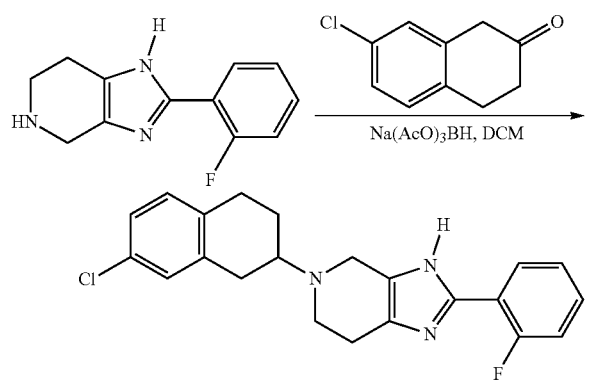

The mixture of 2-(2-fluorophenyl)-4,5,6,7-tetrahydro-3H-imidazo[4,5-c]pyridine (77 mg, 0.35 mmol), 7-chloro-3,4-dihydronaphthalen-2(1H)-one (63 mg, 0.35 mmol) and Na(AcO)$_3$BH (147 mg, 0.7 mmol) in dichloromethane (7 mL) was stirred at room temperature for 16 hrs. The resulting mixture was evaporated under vacuum and then purified by Prep-HPLC: 20% to 35% acetonitrile in water (0.1% trifluoroacetic acid). This resulted in 5-(7-chloro-1,2,3,4-tetrahydronaphthalen-2-yl)-2-(2-fluorophenyl)-4,5,6,7-tetrahydro-3H-imidazo[4,5-c]pyridine, trifluoroacetic acid salt (20 mg, 12%) as a white solid. MS (ESI): mass calcd. for $C_{22}H_{21}ClFN_3$ 381.88, m/z found 381.8 [M+H]$^+$. $^1$H NMR (400 MHz, CD$_3$OD) δ ppm 7.97 (t, J$_1$=J$_2$=8.0 Hz, 1H), 7.55 (s, 1H), 7.39-7.17 (m, 5H), 4.62-4.51 (m, 2H), 3.95-3.82 (m, 3H), 3.33-2.95 (m, 6H), 2.50-2.47 (m, 1H), 2.12-2.01 (m, 1H).

Example 7: 2-(2-fluorophenyl)-5-(6-methoxy-1,2,3,4-tetrahydronaphthalen-2-yl)-4,5,6,7-tetrahydro-3H-imidazo[4,5-c]pyridine

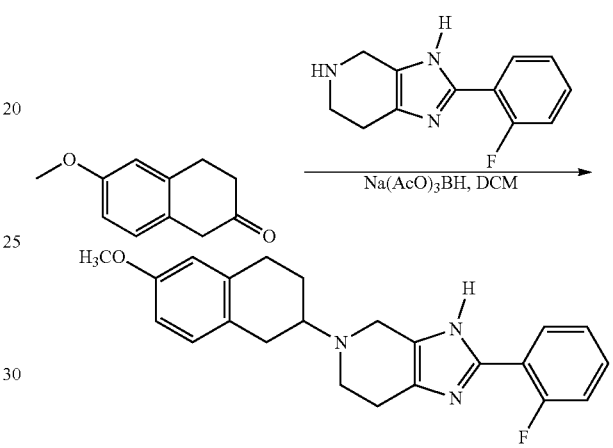

The mixture of 2-(2-fluorophenyl)-4,5,6,7-tetrahydro-3H-imidazo[4,5-c]pyridine (77 mg, 0.35 mmol), 6-methoxy-3,4-dihydronaphthalen-2(1H)-one (63 mg, 0.35 mmol) and Na(AcO)$_3$BH (147 mg, 0.7 mmol) in dichloromethane (7 mL) was stirred at room temperature for 16 hrs. The resulting mixture was evaporated under vacuum and then purified by Prep-HPLC: 20% to 35% acetonitrile in water (0.1% trifluoroacetic acid). This resulted in 2-(2-fluorophenyl)-5-(6-methoxy-1,2,3,4-tetrahydronaphthalen-2-yl)-4,5,6,7-tetrahydro-3H-imidazo[4,5-c]pyridine, trifluoroacetic acid salt (15 mg, 12%) as a white solid. MS (ESI): mass calcd. for $C_{23}H_{24}FN_3O$ 377.46, m/z found 377.9 [M+H]$^+$. $^1$H NMR (400 MHz, CD$_3$OD) δ ppm 7.97 (t, J$_1$=J$_2$=8.0 Hz, 1H), 7.58-7.56 (m, 1H), 7.41-7.34 (m, 2H), 7.12 (d, J=8.4 Hz, 1H), 6.80-6.75 (m, 2H), 4.64-4.55 (m, 2H), 3.96-3.79 (m, 6H), 3.30-3.01 (m, 6H), 2.48-2.46 (m, 1H), 2.11-2.00 (m, 1H).

Example 8: 2-(2-fluorophenyl)-5-(7-methoxy-1,2,3,4-tetrahydronaphthalen-2-yl)-4,5,6,7-tetrahydro-3H-imidazo[4,5-c]pyridine

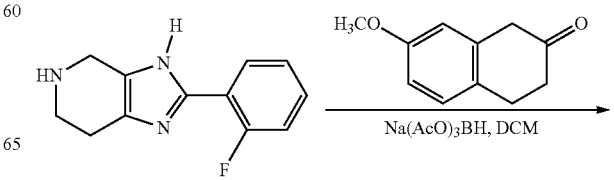

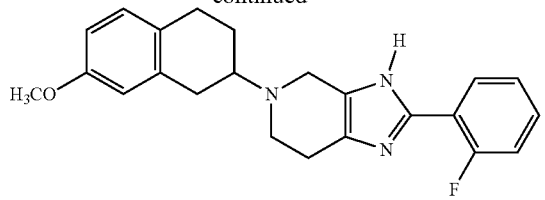

The mixture of 2-(2-fluorophenyl)-4,5,6,7-tetrahydro-3H-imidazo[4,5-c]pyridine (77 mg, 0.35 mmol), 7-methoxy-3,4-dihydronaphthalen-2(1H)-one (63 mg, 0.35 mmol) and Na(AcO)$_3$BH (147 mg, 0.7 mmol) in dichloromethane (7 mL) was stirred at room temperature for 16 hrs. The resulting mixture was evaporated under vacuum and then purified by Prep-HPLC: 20% to 35% acetonitrile in water (0.1% trifluoroacetic acid). This resulted in 2-(2-fluorophenyl)-5-(7-methoxy-1,2,3,4-tetrahydronaphthalen-2-yl)-4,5,6,7-tetrahydro-3H-imidazo[4,5-c]pyridine, trifluoroacetic acid salt (20 mg, 12%) as a white solid. MS (ESI): mass calcd. for C$_{23}$H$_{24}$FN$_3$O 377.46, m/z found 377.9 [M+H]$^+$. $^1$H NMR (400 MHz, CD$_3$OD) δ ppm 7.97 (t, J$_1$=J$_2$=8.0 Hz, 1H), 7.58 (m, 1H), 7.41-7.34 (m, 2H), 7.10 (d, J=8.4 Hz, 1H), 6.81-6.78 (m, 2H), 4.61-4.56 (m, 2H), 3.93-3.79 (m, 6H), 3.30-3.01 (m, 6H), 2.48-2.46 (m, 1H), 2.10-2.00 (m, 1H).

Example 9: 2-(2-fluorophenyl)-5-(8-methoxy-1,2,3,4-tetrahydronaphthalen-2-yl)-4,5,6,7-tetrahydro-3H-imidazo[4,5-c]pyridine

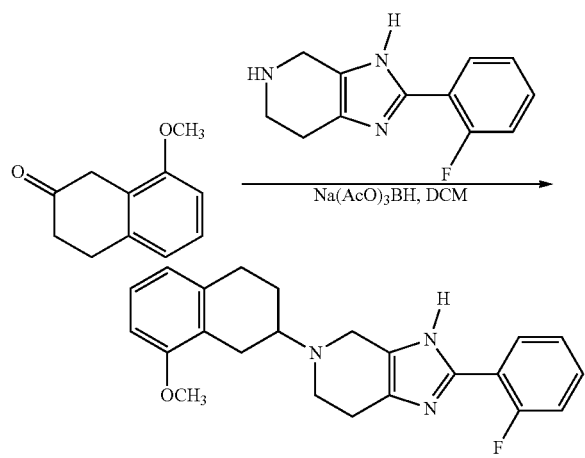

The mixture of 2-(2-fluorophenyl)-4,5,6,7-tetrahydro-3H-imidazo[4,5-c]pyridine (77 mg, 0.35 mmol), 8-methoxy-3,4-dihydronaphthalen-2(1H)-one (63 mg, 0.35 mmol) and Na(AcO)$_3$BH (147 mg, 0.7 mmol) in dichloromethane (7 mL) was stirred at room temperature for 16 hrs. The resulting mixture was evaporated under vacuum and then purified by Prep-HPLC: 20% to 35% acetonitrile in water (0.1% trifluoroacetic acid). This resulted in 2-(2-fluorophenyl)-5-(8-methoxy-1,2,3,4-tetrahydronaphthalen-2-yl)-4,5,6,7-tetrahydro-3H-imidazo[4,5-c]pyridine, trifluoroacetic acid salt (25 mg, 15%) as a white solid. MS (ESI): mass calcd. for C$_{23}$H$_{24}$FN$_3$O 377.46, m/z found 377.9 [M+H]$^+$. $^1$H NMR (400 MHz, CD$_3$OD) δ ppm 7.97 (t, J$_1$=J$_2$=8.0 Hz, 1H), 7.59 (s, 1H), 7.41-7.34 (m, 2H), 7.19 (t, J$_1$=J$_2$=8.0 Hz, 1H), 6.84-6.78 (m, 2H), 4.65-4.58 (m, 2H), 3.96-3.86 (m, 6H), 3.30-2.88 (m, 6H), 2.48-2.45 (m, 1H), 2.07-1.97 (m, 1H).

Example 10: 2-(2-chlorophenyl)-5-(5-methoxy-1,2,3,4-tetrahydronaphthalen-2-yl)-4,5,6,7-tetrahydro-3H-imidazo[4,5-c]pyridine

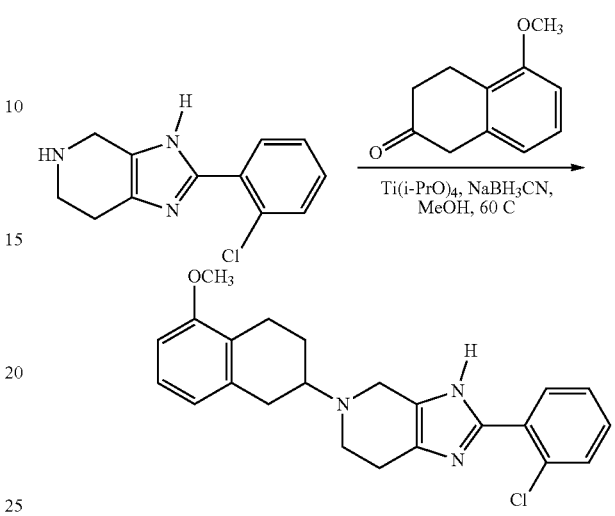

To a solution of 2-(2-chlorophenyl)-4,5,6,7-tetrahydro-3H-imidazo[4,5-c]pyridine (120 mg, 0.51 mmol) and 5-methoxy-3,4-dihydronaphthalen-2(1H)-one (90 mg, 0.51 mmol) in methanol (5 mL) was added Ti(i-PrO)$_4$ (290 mg, 1.02 mmol), the resulting mixture was stirred at room temperature under N$_2$ for 1 h, NaBH$_3$CN (160 mg, 2.55 mmol) was added to the reaction mixture and stirred at 60° C. for 16 hrs. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 10-50) to afford 2-(2-chlorophenyl)-5-(5-methoxy-1,2,3,4-tetrahydronaphthalen-2-yl)-4,5,6,7-tetrahydro-3H-imidazo[4,5-c]pyridine (18 mg, 9% yield) as white solid. MS (ESI): mass calcd. for C$_{23}$H$_{24}$ClN$_3$O 393.16, m/z found 393.8 [M+H]$^+$, $^1$H NMR (400 MHz, CD$_3$OD) δ ppm 8.45 (S, 1H), 7.72-7.74 (m, 1H), 7.54-7.57 (m, 1H), 7.43-7.45 (m, 2H), 7.13-7.17 (t, J=8.0 Hz, 1H), 6.77-6.79 (d, J=8.0 Hz, 2H), 4.24-4.32 (m, 2H), 3.83 (s, 3H), 3.47-3.65 (m, 3H), 3.06-3.24 (m, 5H), 2.62-2.70 (m, 1H), 2.41-2.44 (m, 1H), 1.83-1.94 (m, 1H).

Example 11: 5-(8-fluoro-1,2,3,4-tetrahydronaphthalen-2-yl)-2-(2-fluorophenyl)-4,5,6,7-tetrahydro-3H-imidazo[4,5-c]pyridine

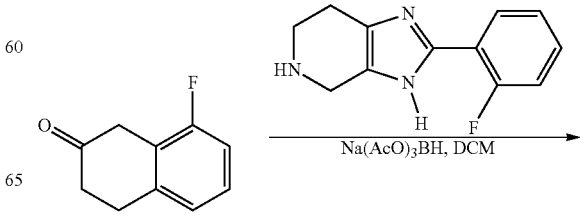

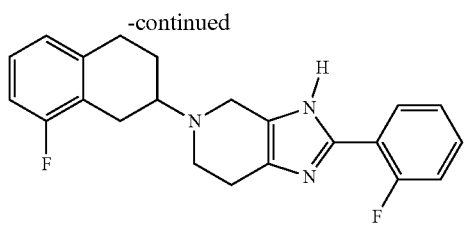

The mixture of 2-(2-fluorophenyl)-4,5,6,7-tetrahydro-3H-imidazo[4,5-c]pyridine (77 mg, 0.35 mmol), 8-fluoro-3,4-dihydronaphthalen-2(1H)-one (56 mg, 0.35 mmol) and Na(AcO)$_3$BH (147 mg, 0.7 mmol) in dichloromethane was stirred at room temperature for 16 hrs. The resulting mixture was evaporated under vacuum and then purified by prep-HPLC: 30% to 60% acetonitrile in water (0.1% trifluoroacetic acid). This resulted in 5-(8-fluoro-1,2,3,4-tetrahydronaphthalen-2-yl)-2-(2-fluorophenyl)-4,5,6,7-tetrahydro-3H-imidazo[4,5-c]pyridine, trifluoroacetic acid salt (18 mg, 11%) as a white solid. MS (ESI): mass calcd. for $C_{22}H_{21}F_2N_3$ 365.43, m/z found 365.8 [M+H]$^+$. $^1$H NMR (400 MHz, CD$_3$OD) δ ppm 7.97 (t, $J_1$=$J_2$=8.0 Hz, 1H), 7.57 (s, 1H), 7.40-7.38 (m, 2H), 7.20 (t, $J_1$=$J_2$=6.0 Hz, 1H), 7.04-6.95 (m, 2H), 4.64-4.57 (m, 2H), 3.97-3.85 (m, 3H), 3.33-2.95 (m, 6H), 2.50-2.48 (m, 1H), 2.12-2.02 (m, 1H).

Example 12: 5-(4-chloro-2,3-dihydro-1H-inden-2-yl)-2-(2-chlorophenyl)-4,5,6,7-tetrahydro-3H-imidazo[4,5-c]pyridine

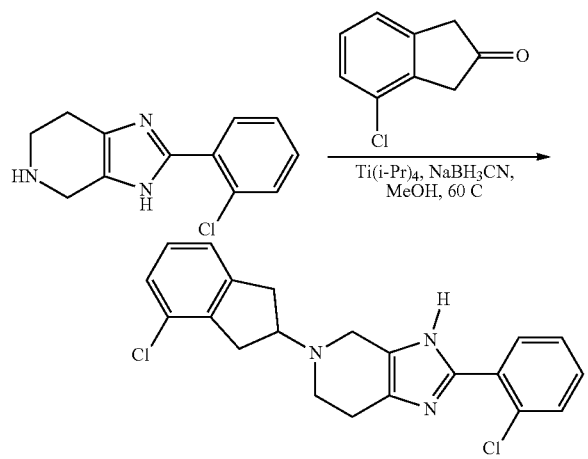

To a solution of 2-(2-chlorophenyl)-4,5,6,7-tetrahydro-3H-imidazo[4,5-c]pyridine (120 mg, 0.51 mmol) and 4-chloro-1,3-dihydro-2H-inden-2-one (85 mg, 0.51 mmol) in methanol (5 mL) was added Ti(i-PrO)$_4$ (290 mg, 1.02 mmol), the resulting mixture was stirred at room temperature under N$_2$ for 1 h, NaBH$_3$CN (160 mg, 2.55 mmol) was added to the reaction mixture and stirred at 60° C. for 16 hrs. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% trifluoroacetic acid), gradient: 10-60) to afford (RS) 5-(4-chloro-2,3-dihydro-1H-inden-2-yl)-2-(2-chlorophenyl)-4,5,6,7-tetrahydro-3H-imidazo[4,5-c]pyridine (30 mg, 15% yield) as white solid. MS (ESI): mass calcd. for $C_{21}H_{19}Cl_2N_3$ 383.10, m/z found 383.7 [M+H]$^+$, $^1$H NMR (400 MHz, CD$_3$OD) δ ppm 7.75-7.76 (m, 1H), 7.66-7.68 (m, 1H), 7.53-7.62 (m, 2H), 7.28-7.31 (m, 3H), 4.44-4.55 (m, 3H), 3.79-3.83 (m, 2H), 3.63-3.71 (m, 2H), 3.37-3.50 (m, 2H), 3.22-3.25 (m, 2H).

Example 13: 5-(7-chloro-1,2,3,4-tetrahydronaphthalen-2-yl)-2-(2-chlorophenyl)-4,5,6,7-tetrahydro-3H-imidazo[4,5-c]pyridine

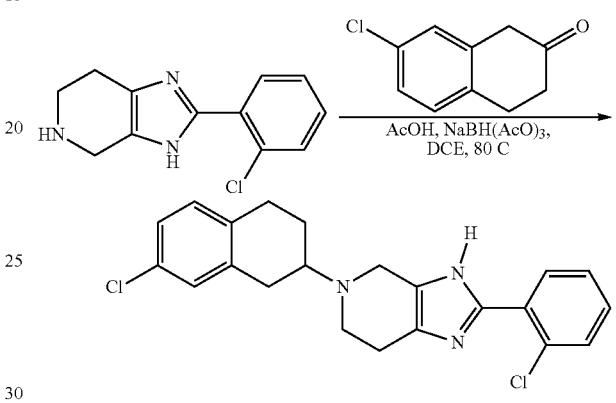

To a solution of 2-(2-chlorophenyl)-4,5,6,7-tetrahydro-3H-imidazo[4,5-c]pyridine (80 mg, 0.34 mmol) and 7-chloro-3,4-dihydronaphthalen-2(1H)-one (62 mg, 0.34 mmol) in 1,2-dichloroethane (5 mL) was added acetic acid (0.2 mL), the resulting mixture was stirred at room temperature under N$_2$ for 1 h, NaBH(AcO)$_3$ (136 mg, 0.68 mmol) was added to the reaction mixture and stirred at 80° C. for 16 hrs. After the reaction was finished, it was quenched with H$_2$O and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 10-40) to afford 5-(7-chloro-1,2,3,4-tetrahydronaphthalen-2-yl)-2-(2-chlorophenyl)-4,5,6,7-tetrahydro-3H-imidazo[4,5-c]pyridine (22 mg, 16% yield) as white solid. MS (ESI): mass calcd. for $C_{22}H_{21}Cl_2N_3$ 397.11, m/z found 397.8 [M+H]$^+$, $^1$H NMR (400 MHz, CD$_3$OD) δ ppm 8.40 (s, 1H), 7.72-7.74 (m, 1H), 7.54-7.57 (m, 1H), 7.43-7.45 (m, 2H), 7.11-7.20 (m, 3H), 4.18-4.27 (m, 2H), 3.44-3.54 (m, 3H), 3.20-3.24 (m, 1H), 2.92-3.41 (m, 5H), 2.37-2.40 (m, 1H), 1.91-1.95 (m, 1H).

Example 14: 8-chloro-2-(2-(2-chlorophenyl)-3,4,6,7-tetrahydro-5H-imidazo[4,5-c]pyridin-5-yl)-1,2,3,4-tetrahydronaphthalen-1-ol

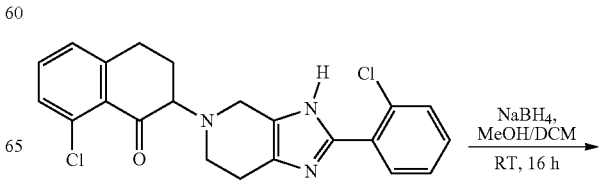

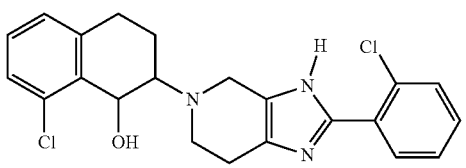

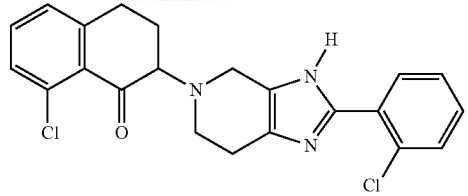

To a solution of 8-chloro-2-(2-(2-chlorophenyl)-3,4,6,7-tetrahydro-5H-imidazo[4,5-c]pyridin-5-yl)-3,4-dihydronaphthalen-1(2H)-one (180 mg, 0.43 mmol) in methanol (9 mL) and dichloromethane (9 mL) was added NaBH$_4$ (163 mg, 4.3 mmol) in portions. The resulting mixture was stirred at room temperature for 16 hours. The mixture was concentrated and purified by prep-HPLC to afford 8-chloro-2-(2-(2-chlorophenyl)-3,4,6,7-tetrahydro-5H-imidazo[4,5-c]pyridin-5-yl)-1,2,3,4-tetrahydronaphthalen-1-ol (12 mg, 31%) as white solid. MS (ESI): mass calcd. for C$_{22}$H$_{21}$Cl$_2$N$_3$O 413.11, m/z found 413.7 [M+H]$^+$. $^1$H NMR (400 MHz, CD$_3$OD) δ ppm 8.44 (s, 1H), 7.74 (m, 1H), 7.56 (m, 1H), 7.47-7.35 (m, 2H), 7.31 (d, J=8 Hz, 1H), 7.27 (t, J=8 Hz, 1H), 7.18 (d, J=8 Hz, 1H), 5.49 (s, 1H), 4.51 (q, J=14, 2H), 3.80 (m, 1H), 3.67 (m, 1H), 3.38 (m, 1H), 3.17-3.90 (m, 4H), 2.32 (m, 2H).

Example 14-1: 8-chloro-2-(2-(2-chlorophenyl)-3,4,6,7-tetrahydro-5H-imidazo[4,5-c]pyridin-5-yl)-3,4-dihydronaphthalen-1(2H)-one

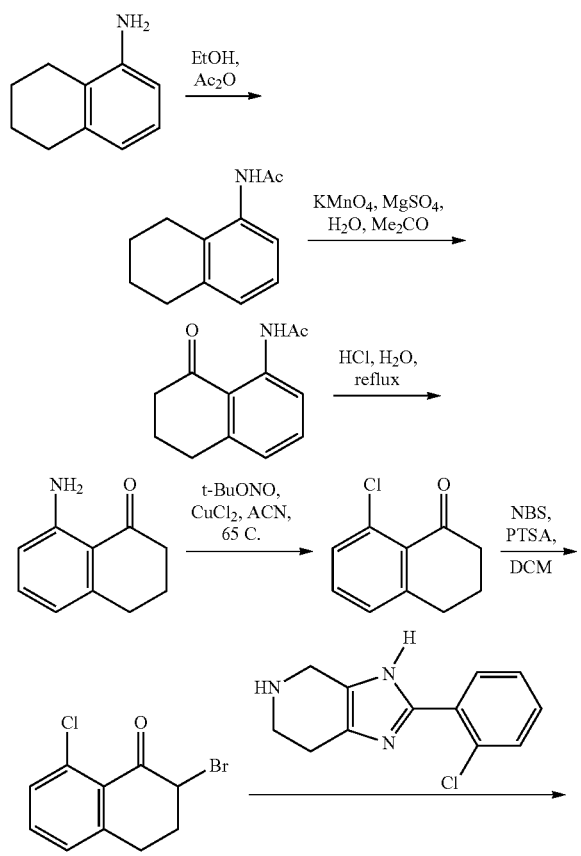

5,6,7,8-tetrahydronaphthalen-1-amine (7.4 g, 0.05 mol) was added dropwise to a solution of acetic anhydride (10.2 g, 0.1 mol) in ethanol (120 mL) at 0° C. The mixture was stirred at room temperature for 16 hours. The resulting mixture was concentrated and purified by silica column with 0-10% methanol in dichloromethane to afford N-(5,6,7,8-tetrahydronaphthalen-1-yl)acetamide (10 g, crude) as white solid. MS (ESI): mass calcd. for C$_{12}$H$_{15}$NO 189.12, m/z found 189.8 [M+H]$^+$.

To a mixture of N-(5,6,7,8-tetrahydronaphthalen-1-yl)acetamide (4.5 g, 24 mmol) and MgSO$_4$ in acetone (170 mL) and H$_2$O (20 mL) was added KMnO$_4$ (4 g, 34 mmol) at ice bath. The mixture was stirred at room temperature for 2 hours. Filtered through celite, the solid was washed with dichloromethane (100 mL) and water (60 mL). The organic layer was separated and washed with brine (60 mL), dried and purified by silica column with 0-20% ethyl acetate in petroleum ether to afford N-(8-oxo-5,6,7,8-tetrahydronaphthalen-1-yl)acetamide (4.5 g, 91% yield) as white solid. MS (ESI): mass calcd. for C$_{12}$H$_{13}$NO$_2$ 203.09, m/z found 203.8 [M+H]$^+$.

A mixture of N-(8-oxo-5,6,7,8-tetrahydronaphthalen-1-yl)acetamide (2.03 g, 10 mmol) in an aq. of 6N HCl solution (50 mL) was stirred at 90° C. for 3 hour. Ethyl acetate (100 mL) was added, and pH was adjusted to 8 with NaOH at ice bath. The organic phase was washed with brine (50 mL), dried, concentrated to afford 8-amino-3,4-dihydronaphthalen-1(2H)-one (2 g, crude) as brown solid. MS (ESI): mass calcd. for C$_{10}$H$_{11}$NO 161.08, m/z found 161.9 [M+H]$^+$.

To a mixture of 8-amino-3,4-dihydronaphthalen-1(2H)-one (1.9 g, 11.7 mmol) and CuCl$_2$ (2 g, 15.2 mmol) in acetonitrile (38 mL) was added t-BuONO (2.4 mL, 19.9 mmol). The mixture was stirred at room temperature for 2 hours. The reaction mixture was concentrated and purified by silica column with 0-3% ethyl acetate in petroleum ether to afford 8-chloro-3,4-dihydronaphthalen-1(2H)-one (1 g, 47%) as yellow oil. MS (ESI): mass calcd. for C$_{10}$H$_9$ClO 180.03, m/z found 180.7 [M+H]$^+$.

A mixture of 8-chloro-3,4-dihydronaphthalen-1(2H)-one (500 mg, 2.8 mmol) and N-bromosuccinimide (544 mg, 3 mmol) in DMSO (5 mL) was stirred at 45° C. for 48 hours. The mixture was quenched with an aq. NH$_4$Cl solution (5 mL), extracted with ethyl acetate (50 mL). The organic phase was washed with brine (30 mL), concentrated and purified by silica column with 0-20% dichloromethane in petroleum ether to afford 2-bromo-8-chloro-3,4-dihydronaphthalen-1(2H)-one (700 mg, 96% yield) as yellow solid. MS (ESI): mass calcd. for C$_{10}$H$_8$BrClO 257.94, m/z found 258.6, 260.8[M+H]$^+$.

The mixture of 2-bromo-8-chloro-3,4-dihydronaphthalen-1(2H)-one (222 mg, 0.85 mmol), 2-(2-chlorophenyl)-4,5,6,7-tetrahydro-3H-imidazo[4,5-c]pyridine (200 mg, 0.85 mmol) and K$_2$CO$_3$ (235 mg, 1.7 mmol) in acetonitrile was stirred at 35° C. for 40 hrs. The mixture was quenched with water (2 mL), extracted with ethyl acetate (20 mL). The organic phase was concentrated, purified by silica column with 0-3% methanol in dichloromethane to afford 8-chloro- 2-(2-(2-chlorophenyl)-3,4,6,7-tetrahydro-5H-imidazo[4,5-c]pyridin-5-yl)-3,4-dihydronaphthalen-1(2H)-one (200 mg, 56% yield). MS (ESI): mass calcd. for C$_{22}$H$_{19}$Cl$_2$N$_3$O 411.09, m/z found 411.7 [M+H]$^+$. $^1$H NMR (400 MHz, DMSO-d$_6$) δ ppm 11.93 (s, 1H), 7.71 (s, 1H), 7.50-7.26 (m, 6H), 3.66-3.45 (m, 3H), 3.15-2.58 (m, 7H), 2.21 (s, 1H).

Example 15: 2-(2-chlorophenyl)-5-(7-methoxy-1,2,3,4-tetrahydronaphthalen-2-yl)-4,5,6,7-tetrahydro-3H-imidazo[4,5-c]pyridine

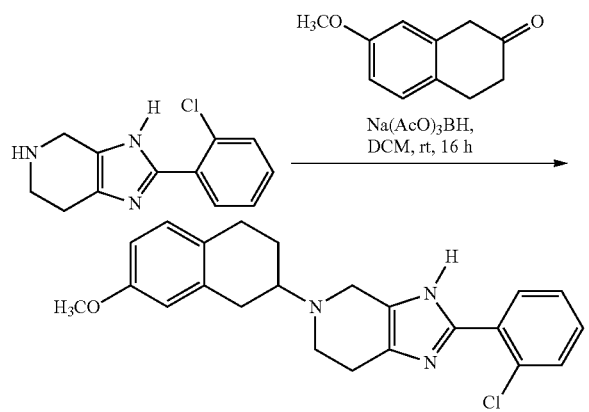

A mixture of 7-methoxy-3,4-dihydronaphthalen-2(1H)-one (150 mg, 0.85 mmol), 2-(2-chloro-phenyl)-4,5,6,7-tetrahydro-3H-imidazo[4,5-c]pyridine (200 mg, 0.85 mmol) and NaBH(OAc)$_3$ (1.7 mmol) in dichloromethane (10 mL) was stirred at room temperature for 16 hours. The solvent was evaporated and purified by prep-HPLC to afford 2-(2-chlorophenyl)-5-(7-methoxy-1,2,3,4-tetrahydronaphthalen-2-yl)-4,5,6,7-tetrahydro-3H-imidazo[4,5-c]pyridine (50 mg, 13% yield) as white solid. MS (ESI): mass calcd. for C$_{23}$H$_{24}$ClN$_3$O 393.92, m/z found 393.8 [M+H]$^+$. $^1$H NMR (400 MHz, CD$_3$OD) δ ppm 11.97 (bs, 1H), 8.17 (s, 1H), 7.76 (d, J=8 Hz, 1H), 7.51 (d, J=8 Hz, 1H), 7.34 (m, 2H), 6.98 (d, J=8 Hz, 1H), 6.69 (m, 2H), 3.70 (s, 3H), 3.67 (s, 2H), 2.93-2.74 (m, 9H), 2.04 (m, 1H), 1.69 (m, 1H).

Example 16: 2-(2-chlorophenyl)-5-(8-methoxy-1,2,3,4-tetrahydronaphthalen-2-yl)-4,5,6,7-tetrahydro-3H-imidazo[4,5-c]pyridine

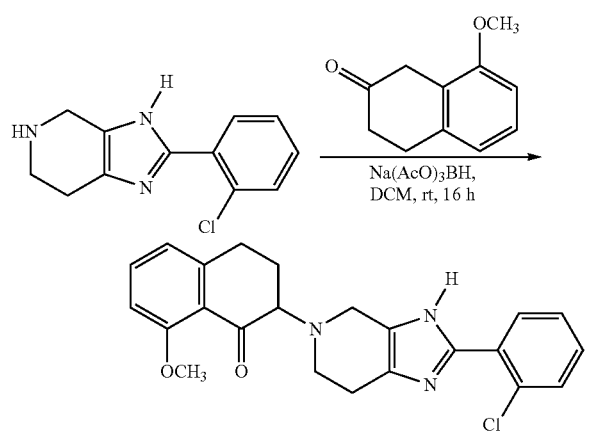

A mixture of 8-methoxy-3,4-dihydronaphthalen-2(1H)-one (150 mg, 0.85 mmol), 2-(2-chloro-phenyl)-4,5,6,7-tetrahydro-3H-imidazo[4,5-c]pyridine (200 mg, 0.85 mmol) and NaBH(OAc)$_3$ (360 mg, 1.7 mmol) in dichloromethane (10 mL) was stirred at room temperature for 16 hours. The solvent was evaporated and purified by prep-HPLC to afford 2-(2-chlorophenyl)-5-(8-methoxy-1,2,3,4-tetrahydronaphthalen-2-yl)-4,5,6,7-tetrahydro-3H-imidazo[4,5-c]pyridine (55 mg, 14% yield) as white solid. MS (ESI): mass calcd. for C$_{23}$H$_{24}$ClN$_3$O 393.16, m/z found 393.8 [M+H]$^+$. $^1$H NMR (400 MHz, DMSO-d$_6$) δ ppm 12.01 (brs, 1H), 8.16 (brs, 1H), 7.77 (d, J=8 Hz, 1H), 7.67 (d, J=8 Hz, 1H), 7.34 (m, 2H), 7.05 (t, J=8 Hz, 1H), 6.76 (d, J=8 Hz, 1H), 6.70 (d, J=8 Hz, 1H), 3.77 (s, 3H), 3.67 (s, 2H), 2.89-2.65 (m, 9H), 2.04 (m, 1H), 1.66 (m, 1H).

Example 17: 5-(8-chloro-1,2,3,4-tetrahydronaphthalen-2-yl)-2-(3-chloropyridin-4-yl)-4,5,6,7-tetrahydro-3H-imidazo[4,5-c]pyridine

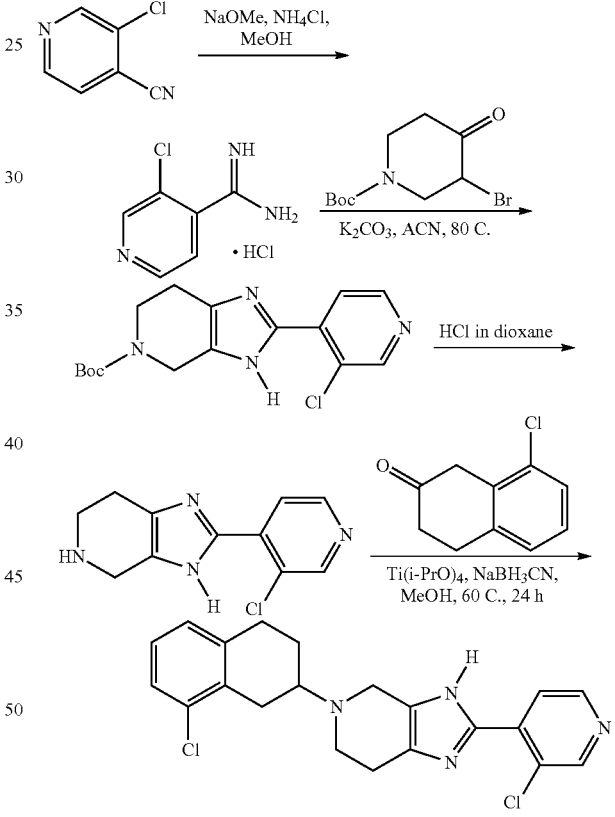

The solution of 3-chloroisonicotinonitrile (2 g, 14.4 mmol) and NaOMe (0.16 g, 2.88 mmol) in methanol (20 mL) was added NH$_4$Cl (0.85 g, 15.8 mmol) after stirred 2 hours at room temperature under nitrogen atmosphere, the resulting solution was stirred for 24 hours. The reaction mixture was filtered, and the mother liquor was evaporated to dryness on a rotary evaporator. The filter cake was combined with the residue from the mother liquor and washing with ether, and then evaporated in vacuo to afford 3-chloroisonicotinimidamide hydrochloride (1.9 g, 69% yield) as a white solid. MS (ESI): mass calcd. for C$_6$H$_7$Cl$_2$N$_3$ 155.03, m/z found 155.7 [M+H]$^+$.

The mixture of 3-chloroisonicotinimidamide hydrochloride (1.8 g, 9.4 mmol), tert-butyl 3-bromo-4-oxopiperidine-1-carboxylate (2.6 g, 9.4 mmol) and potassium carbonate (1.3 g, 9.4 mmol) in acetonitrile (20 mL) was stirred at 80° C. for 16 hrs. The resulting mixture was evaporated under vacuum and purified by silica column (0 to 50% ethyl acetate in petroleum ether). This resulted in tert-butyl 2-(3-chloropyridin-4-yl)-3,4,6,7-tetrahydro-5H-imidazo[4,5-c]pyridine-5-carboxylate (0.85 g, 27% yield). MS (ESI): mass calcd. $C_{16}H_{19}ClN_4O_2$ 334.12, m/z found 334.8 [M+H]$^+$.

The mixture of tert-butyl 2-(3-chloropyridin-4-yl)-3,4,6,7-tetrahydro-5H-imidazo[4,5-c]pyridine-5-carboxylate (850 mg, 2.54 mmol) in HCl (g) in dioxane (4 N, 20 mL) was stirred at room temperature for 16 hrs. The resulting mixture was basified by ammonia to free the product, then concentrated to give crude product, which was purified by chromatography on silica gel, eluting (10:1 dichloromethane:methanol) to afford 2-(3-chloropyridin-4-yl)-4,5,6,7-tetrahydro-3H-imidazo[4,5-c]pyridine (520 mg, 87% yield) as a yellow solid. MS (ESI): mass calcd. for $C_{11}H_{11}ClN_4$ 234.07, m/z found 234.7 [M+H]$^+$.

To a solution of 2-(3-chloropyridin-4-yl)-4,5,6,7-tetrahydro-3H-imidazo[4,5-c]pyridine (100 mg, 0.43 mmol) and 8-chloro-3,4-dihydronaphthalen-2(1H)-one (77 mg, 0.43 mmol) in methanol (5 mL) was added Ti(i-PrO)$_4$ (245 mg, 0.86 mmol), the resulting mixture was stirred at room temperature under N$_2$ for 1 h, NaBH$_3$CN (136 mg, 2.12 mmol) was added to the reaction mixture and stirred at 60° C. for 16 hrs. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: ACN-H$_2$O (0.1% formic acid), gradient: 30-70) to afford 5-(8-chloro-1,2,3,4-tetrahydronaphthalen-2-yl)-2-(3-chloropyridin-4-yl)-4,5,6,7-tetrahydro-3H-imidazo[4,5-c]pyridine (26 mg, 21% yield) as white solid. MS (ESI): mass calcd. for $C_{21}H_{20}Cl_2N_4$ 398.11, m/z found 398.8 [M+H]$^+$, $^1$H NMR (400 MHz, CD$_3$OD) δ ppm 8.69 (s, 1H), 8.55 (s, 1H), 8.37 (s, 1H), 7.87 (s, 1H), 7.11-7.20 (m, 3H), 4.22 (s, 2H), 3.45-3.61 (m, 3H), 2.88-3.23 (m, 6H), 2.36-2.40 (m, 1H), 1.92-1.97 (m, 1H).

Example 18: 5-(8-chloro-1,2,3,4-tetrahydronaphthalen-2-yl)-2-(2-chlorophenyl)-3-methyl-4,5,6,7-tetrahydro-3H-imidazo[4,5-c]pyridine

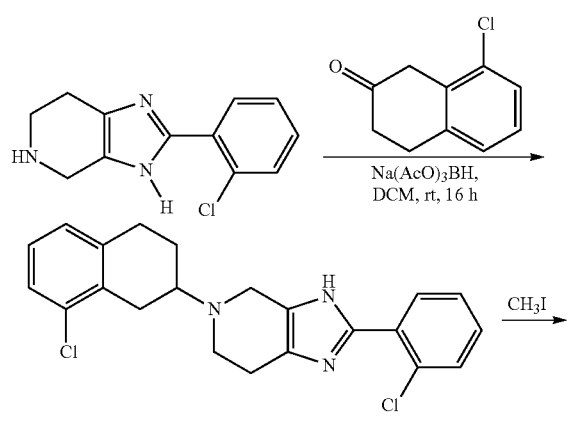

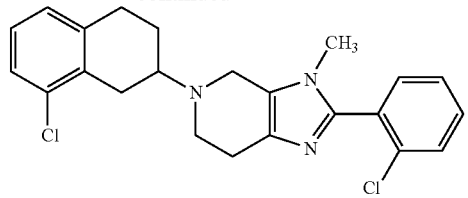

A mixture of 8-chloro-3,4-dihydronaphthalen-2(1H)-one (154 mg, 0.85 mmol), 2-(2-chlorophenyl)-4,5,6,7-tetrahydro-3H-imidazo[4,5-c]pyridine (200 mg, 0.85 mmol) and NaBH(OAc)$_3$ (360 mg, 1.7 mmol) in dichloromethane (10 mL) was stirred at room temperature for 16 hours. The solvent was evaporated and purified by silica column with 0-5% methanol in dichloromethane to afford 5-(8-chloro-1,2,3,4-tetrahydronaphthalen-2-yl)-2-(2-chlorophenyl)-4,5,6,7-tetrahydro-3H-imidazo[4,5-c]pyridine (150 mg, 44% yield) as yellow solid. MS (ESI): mass calcd. for $C_{22}H_{21}C_{12}N_3$ 397.11, m/z found 397.9, 399.8 [M+H]$^+$.

To a mixture of 5-(8-chloro-1,2,3,4-tetrahydronaphthalen-2-yl)-2-(2-chlorophenyl)-4,5,6,7-tetrahydro-3H-imidazo[4,5-c]pyridine (130 mg, 0.33 mmol) and TBAI (9 mg, 0.02 mmol) in an aqueous of 50% NaOH (1.3 mL) and toluene (1.3 mL) was added CH$_3$I (51 mg, 0.36 mmol). The reaction mixture was stirred at room temperature for 2 hours. The mixture was quenched with water (5 mL), extracted with ethyl acetate (30 mL). The organic phase was concentrated and purified by silica column with 1-5% methanol in dichloromethane to give the crude product, which was purified by prep-HPLC to afford 5-(8-chloro-1,2,3,4-tetrahydronaphthalen-2-yl)-2-(2-chlorophenyl)-3-methyl-4,5,6,7-tetrahydro-3H-imidazo[4,5-c]pyridine (11 mg, 7% yield) as white solid. MS (ESI): mass calcd. for $C_{23}H_{23}C_{12}N_3$ 411.13, m/z found 411.7 [M+H]$^+$. $^1$H NMR (400 MHz, CD$_3$OD) δ ppm 7.59 (m, 1H), 7.54-7.49 (m, 1H), 7.45 (m, 2H), 7.22 (m, 1H), 7.14-7.08 (m, 2H), 3.86 (m, 2H), 3.44 (s, 3H), 3.20-3.12 (m, 2H), 3.06-3.00 (m, 2H), 2.94-2.84 (m, 2H), 2.77 (m, 3H), 2.29 (m, 1H), 1.78 (m, 1H).

5-(8-chloro-1,2,3,4-tetrahydronaphthalen-2-yl)-2-(2-chlorophenyl)-3-methyl-4,5,6,7-tetrahydro-3H-imidazo[4,5-c]pyridine (200 mg, 0.49 mmol) was separated by chiral prep-HPLC to afford Example 18-R: 5-((R)-8-chloro-1,2,3,4-tetrahydronaphthalen-2-yl)-2-(2-chlorophenyl)-3-methyl-2,3,4,5,6,7-hexahydro-1H-imidazo[4,5-c]pyridine (30 mg, 15% yield) as white solid and Example 18-S: 5-((S)-8-chloro-1,2,3,4-tetrahydronaphthalen-2-yl)-2-(2-chlorophenyl)-3-methyl-2,3,4,5,6,7-hexahydro-1H-imidazo[4,5-c]pyridine (40 mg, 20% yield) as white solid. Example 18-R: MS (ESI): mass calcd. for $C_{23}H_{23}C_{12}N_3$ 411.13, m/z found 411.8 [M+H]$^+$. Chiral HPLC (CS30_FR12.5.met) Rt=8.66 min. $^1$H NMR (400 MHz, CD$_3$OD) δ ppm 7.58-7.44 (m, 4H), 7.23 (m, 1H), 7.14-7.08 (m, 2H), 3.90 (m, 2H), 3.42 (s, 3H), 3.14-2.78 (m, 9H), 2.29 (m, 1H), 1.79 (m, 1H). Example 18-S: MS (ESI): mass calcd. for $C_{23}H_{23}C_{12}N_3$ 411.13, m/z found 411.8 [M+H]$^+$. Chiral HPLC (CS30_FR12.5.met) Rt=12.51 min. $^1$H NMR (400 MHz, CD$_3$OD) δ ppm 7.58-7.44 (m, 4H), 7.23 (m, 1H), 7.14-7.08 (m, 2H), 3.90 (m, 2H), 3.42 (s, 3H), 3.14-2.78 (m, 9H), 2.29 (m, 1H), 1.79 (m, 1H).

In an alternative procedure, Example 18 can be prepared as follows:

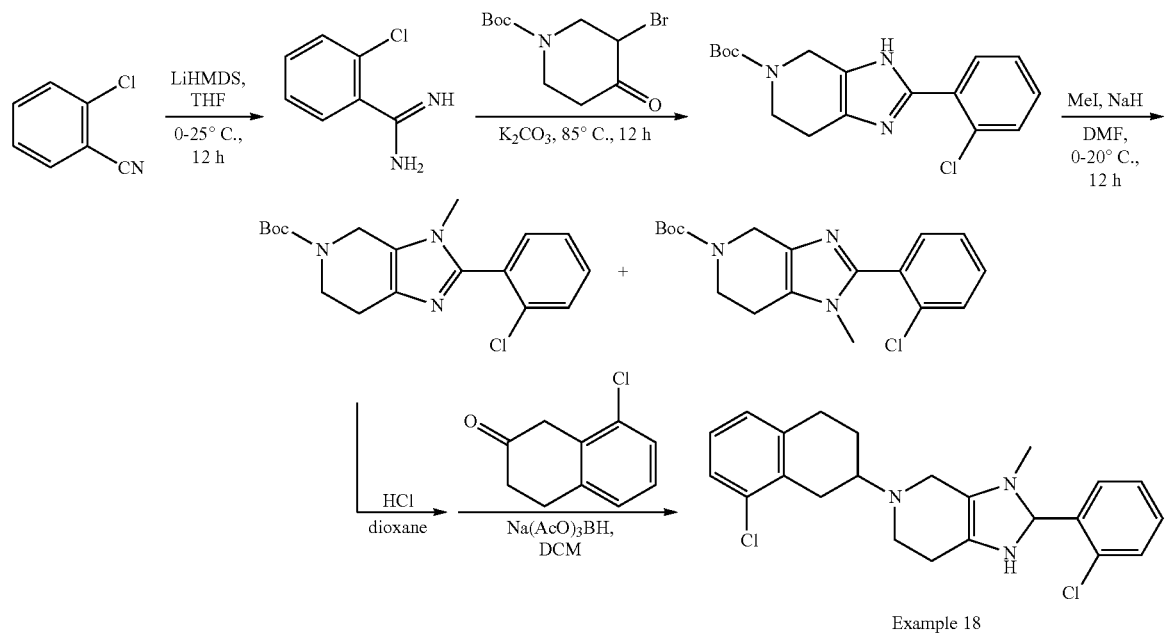

Example 18

To a solution of LiHMDS (1 M, 1.45 L) in tetrahydrofuran (500 mL) was added 2-chlorobenzonitrile (100 g, 726.92 mmol) at 0° C. The resulting mixture was stirred at 25° C. for 12 hr, quenched by addition 3N HCl (2 L) at 0° C., and then diluted with H₂O (500 mL) and extracted with EtOAc (1 L×2). The organic layers were washed with 3N HCl (2 L), and the combined aqueous layers were basified with solid NaOH to pH 14 and extracted with ethyl acetate (500 mL×2). The combined organic layers were then washed with brine (1 L), dried over Na₂SO₄, filtered and concentrated under reduced pressure to give 2-chlorobenzamidine (100 g, crude) as a yellow solid.

To a mixture of 2-chlorobenzamidine (25 g, 161.71 mmol) and tert-butyl 3-bromo-4-oxo-piperidine-1-carboxylate (44.98 g, 161.71 mmol) in acetonitrile (250 mL) was added K₂CO₃ (33.53 g, 242.57 mmol) at 25° C. under N₂. The mixture was heated to 85° C. and stirred for 12 hours, filtered, and the filtrate was concentrated under reduced pressure to give a residue. The residue was purified by column chromatography (SiO₂, 1:0-0:1 petroleum ether: ethyl acetate). Tert-butyl 2-(2-chlorophenyl)-3,4,6,7-tetrahydroimidazo[4,5-c]pyridine-5-carboxy late (20 g, crude) was obtained as a yellow solid.

To a solution of tert-butyl 2-(2-chlorophenyl)-3,4,6,7-tetrahydroimidazo[4,5-c]pyridine-5-carboxylate (12 g, 26.80 mmol, trifluoroacetic acid) in dimethylformamide (80 mL) was added NaH (2.14 g, 53.59 mmol) at 25° C. After addition, the mixture was stirred for 30 min, and then CH₃I (5.71 g, 40.19 mmol) was added drop wise and stirred at 25° C. for 11.5 hr. The reaction mixture was quenched by addition aq. NH₄Cl (500 mL), diluted with H₂O (100 mL), and extracted with ethyl acetate (300 mL×4). The combined organic layers were concentrated under reduced pressure to give a residue, which was purified by column chromatography (SiO₂, 1:0-0:1 petroleum ether:ethyl acetate). Tert-butyl 2-(2-chlorophenyl)-3-methyl-6,7-dihydro-4H-imidazo[4,5-c]pyridine-5-carboxylate ($^1$H NMR (400 MHz, CD₃OD) δ 7.74-7.26 (m, 4H), 4.45 (br, 2H), 3.68 (br, 2H), 3.32 (s, 3H), 2.68 (s, 2H), 1.51-1.34 (m, 9H); a yellow oil) and tert-butyl 2-(2-chlorophenyl)-1-methyl-1,4,6,7-tetrahydro-5H-imidazo[4,5-c]pyridine-5-carboxylate were obtained.

Tert-butyl 2-(2-chlorophenyl)-3-methyl-6,7-dihydro-4H-imidazo[4,5-c]pyridine-5-carboxylate was treated with HCl in dioxane to obtain 2-(2-chlorophenyl)-3-methyl-4,5,6,7-tetrahydro-3H-imidazo[4,5-c]pyridine, which was then coupled with 8-chloro-3,4-dihydronaphthalen-2(1H)-one as provided above to provide Example 18.

Example 18-A: 5-(8-chloro-1,2,3,4-tetrahydronaphthalen-2-yl)-2-(2-chlorophenyl)-1-methyl-4,5,6,7-tetrahydro-1H-imidazo[4,5-c]pyridine

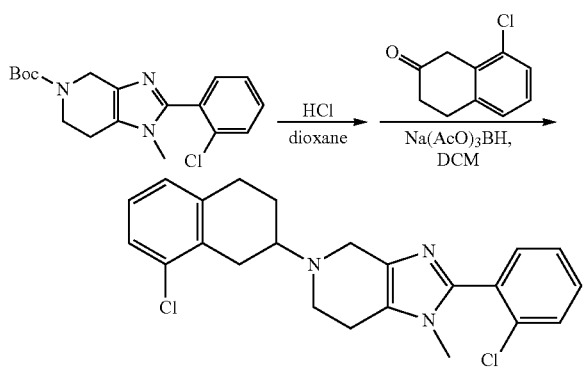

Tert-butyl 2-(2-chlorophenyl)-1-methyl-1,4,6,7-tetrahydro-5H-imidazo[4,5-c]pyridine-5-carboxylate was treated with HCl in dioxane to obtain 2-(2-chlorophenyl)-1-methyl-4,5,6,7-tetrahydro-1H-imidazo[4,5-c]pyridine, which was then coupled with 8-chloro-3,4-dihydronaphthalen-2(1H)-one as provided above in Example 18 to give Example 18-A (5-(8-chloro-1,2,3,4-tetrahydronaphthalen-2-yl)-2-(2-chlorophenyl)-1-methyl-4,5,6,7-tetrahydro-1H-imidazo[4,5-c]pyridine).

Example 19: 5-(5-chloro-2,3-dihydro-1H-inden-2-yl)-2-(2-chlorophenyl)-4,5,6,7-tetrahydro-3H-imidazo[4,5-c]pyridine

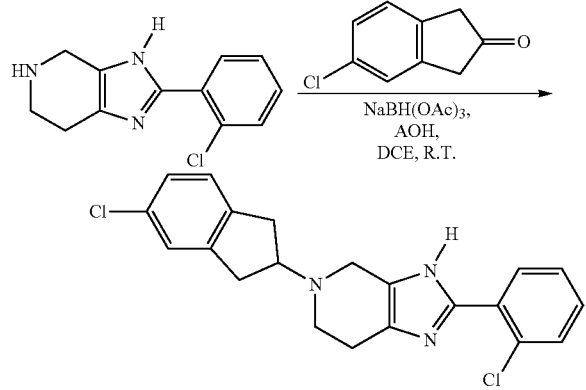

To a solution of 2-(2-chlorophenyl)-4,5,6,7-tetrahydro-3H-imidazo[4,5-c]pyridine (94 mg, 0.4 mmol) and 5-chloro-1,3-dihydro-2H-inden-2-one (67 mg, 0.4 mmol) in 1,2-dichloroethane (10 mL) was added acetic acid (1 drop). The solution was stirred at room temperature for 2 hours under nitrogen atmosphere. NaBH(OAc)$_3$ was added. The mixture was stirred at room temperature for 12 hours. The reaction mixture was diluted with dichloromethane (60 mL), washed with sat. NaHCO$_3$ solution (30 mL), water (30 mL), brine (30 mL), dried, concentrated, and purified on prep-HPLC to afford 5-(5-chloro-2,3-dihydro-1H-inden-2-yl)-2-(2-chlorophenyl)-4,5,6,7-tetrahydro-3H-imidazo[4,5-c]pyridine (10 mg, 6% yield) as white solid. MS (ESI): mass calcd. for C$_{21}$H$_{19}$Cl$_2$N$_3$ 383.10, m/z found 383.8 [M+H]$^+$. $^1$H NMR (400 MHz, CD$_3$OD) δ 8.30 (s, 1H), 7.77-7.68 (m, 1H), 7.59-7.51 (m, 1H), 7.48-7.39 (m, 2H), 7.29 (s, 1H), 7.22 (dt, J=8.0, 4.9 Hz, 2H), 3.98 (s, 2H), 3.87 (d, J=5.8 Hz, 1H), 3.44-3.34 (m, 2H), 3.31-3.22 (m, 2H), 3.13 (dt, J=23.1, 11.1 Hz, 2H), 2.99-2.93 (s, 2H).

Example 20: (2R,3R)-3-(2-(2-chlorophenyl)-3,4,6,7-tetrahydro-5H-imidazo[4,5-c]pyridin-5-yl)-1,2,3,4-tetrahydronaphthalen-2-ol

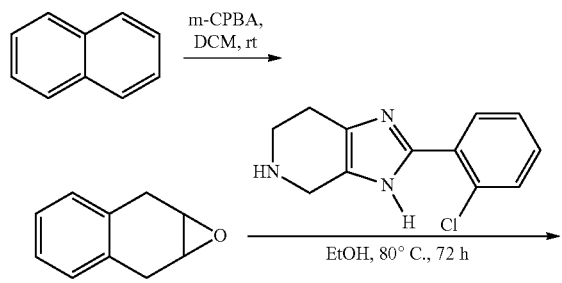

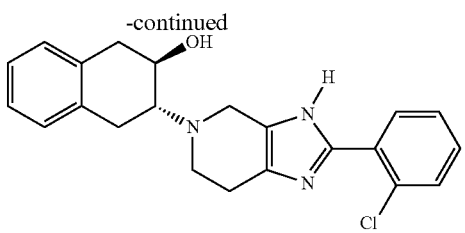

To a solution of 1,4-dihydronaphthalene (1 g, 7.7 mmol) in dichloromethane (10 mL) was added m-CPBA (1.5 g, 8.5 mmol). The mixture was stirred at room temperature for 24 hours. The reaction mixture was filtered and the solid was washed with dichloromethane (30 mL). The filtrate was washed sat. NaHCO$_3$ (20 mL), dried, concentrated and purified by silica column with 0-10% ethyl acetate in petroleum ether to afford 1a,2,7,7a-tetrahydronaphtho[2,3-b]oxirene (0.7 g, 62 yield) as white solid. MS (ESI): mass calcd. for C$_{10}$H$_{10}$O 146.07, m/z found 146.8 [M+H]$^+$.

A solution of 1a,2,7,7a-tetrahydronaphtho[2,3-b]oxirene (147 mg, 1 mmol) and 2-(2-chlorophenyl)-4,5,6,7-tetrahydro-3H-imidazo[4,5-c]pyridine (234 mg, 1 mmol) in ethanol (3 ml) was stirred at 80° C. for 12 hours. The reaction solution was concentrated and purified by prep-HPLC to afford (2R,3R)-3-(2-(2-chlorophenyl)-3,4,6,7-tetrahydro-5H-imidazo[4,5-c]pyridin-5-yl)-1,2,3,4-tetrahydronaphthalen-2-ol (120 mg, 28% yield) as white solid. MS (ESI): mass calcd. for C$_{22}$H$_{22}$ClN$_3$O 379.15, m/z found 379.8 [M+H]$^+$. $^1$H NMR (400 MHz, CD$_3$OD) δ ppm 8.41 (s, 1H), 7.72 (m, 1H), 7.56 (m, 1H), 7.41 (m, 2H), 7.21 (m, 4H), 4.33 (m, 2H), 4.26 (m, 1H), 3.59 (m, 3H), 3.25-2.93 (m, 6H).

Example 21: 5-(7-chloro-1,2,3,4-tetrahydronaphthalen-2-yl)-2-(2,3-dichlorophenyl)-4,5,6,7-tetrahydro-3H-imidazo[4,5-c]pyridine

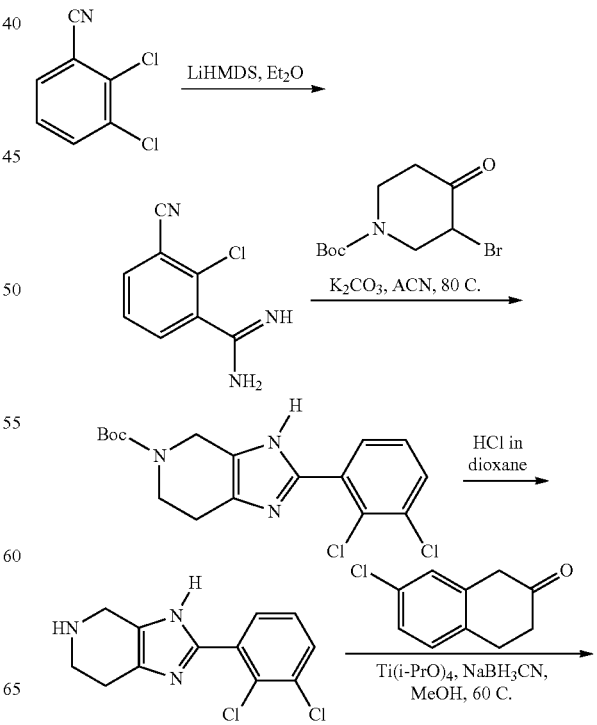

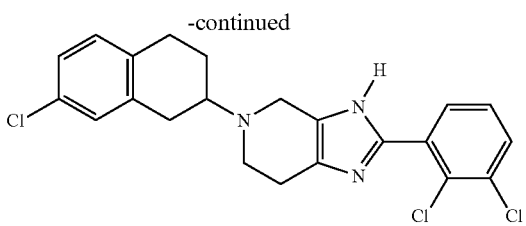

The solution of 2,3-dichlorobenzonitrile (5 g, 29 mmol) in diethyl ether (100 mL) was dropwise added to LiHMDS (1 M in tetrahydrofuran, 60 mL) with stirring under nitrogen atmosphere at 0° C. The resulting solution was stirred at 0° C. to room temperature for 16 hrs. The resulting solution was quenched with 3N hydrochloric acid (100 mL) at 0° C. The water phase was collected, the pH of the water phase was adjusted to 14 with NaOH aqueous, and extracted with ethyl acetate (100 mL×3). The combined organic phases were washed with brine (100 mL), dried over anhydrous $Na_2SO_4$ and evaporated in vacuo. This resulted in 2,3-dichlorobenzimidamide (4.7 g, 87% yield) as a brown solid. MS (ESI): mass calcd. for $C_7H_6Cl_2N_2$ 187.99, m/z found 188.8 $[M+H]^+$.

The mixture of 2,3-dichlorobenzimidamide (2 g, 10.6 mmol), tert-butyl 3-bromo-4-oxopiperidine-1-carboxylate (2.95 g, 10.6 mmol) and potassium carbonate (1.46 g, 10.6 mmol) in acetonitrile (40 mL) was stirred at 80° C. for 16 hrs. The resulting mixture was evaporated under vacuum and purified by silica column (0~50% ethyl acetate in petroleum ether). This resulted in tert-butyl 2-(2,3-dichlorophenyl)-3,4,6,7-tetrahydro-5H-imidazo[4,5-c]pyridine-5-carboxylate (0.78 g, 20% yield). MS (ESI): mass calcd. for $C_{17}H_{19}Cl_2N_3O_2$ 367.09, m/z found 367.9 $[M+H]^+$.

The mixture of tert-butyl 2-(2,3-dichlorophenyl)-3,4,6,7-tetrahydro-5H-imidazo[4,5-c]pyridine-5-carboxylate (780 mg, 2.1 mmol) in HCl (g) in dioxane (4N, 20 mL) was stirred at room temperature for 16 hrs. The resulting mixture was basified by ammonia to free the product, then concentrated to give crude product, which was purified by chromatography on silica gel, eluting (10:1 dichloromethane:methanol) to afford 2-(2,3-dichlorophenyl)-4,5,6,7-tetrahydro-3H-imidazo[4,5-c]pyridine (560 mg, 98% yield) as a yellow solid. MS (ESI): mass calcd. for $C_{12}H_{11}Cl_2N_3$ 267.03, m/z found 267.8 $[M+H]^+$.

To a solution of 2-(2,3-dichlorophenyl)-4,5,6,7-tetrahydro-3H-imidazo[4,5-c]pyridine (134 mg, 0.5 mmol) and 7-chloro-3,4-dihydronaphthalen-2(1H)-one (90 mg, 0.5 mmol) in methanol (5 mL) was added Ti(i-PrO)$_4$ (284 mg, 1.0 mmol), the resulting mixture was stirred at room temperature under $N_2$ for 1 h, NaBH$_3$CN (157, 2.5 mmol) was added to the reaction mixture and stirred at 60° C. for 16 hrs. After the reaction was finished, it was quenched with $H_2O$ and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 20-70) to afford 5-(7-chloro-1,2,3,4-tetrahydronaphthalen-2-yl)-2-(2,3-dichlorophenyl)-4,5,6,7-tetrahydro-3H-imidazo[4,5-c]pyridine (33 mg, 15% yield) as white solid. MS (ESI): mass calcd. for $C_{22}H_{20}Cl_3N_3$ 431.07, m/z found 431.7 $[M+H]^+$, $^1H$ NMR (400 MHz, CD$_3$OD) δ ppm 8.37 (s, 1H), 7.64-7.66 (m, 2H), 7.40-7.44 (t, J=8.0, 1H), 7.20 (s, 1H), 7.11-7.16 (m, 2H), 4.13-4.22 (m, 2H), 3.39-3.52 (m, 3H), 2.91-3.23 (m, 6H), 2.35-2.39 (m, 1H), 1.87-1.97 (m, 1H).

Example 22: 5-(7-chloro-1,2,3,4-tetrahydronaphthalen-2-yl)-2-(2-chloro-4-fluorophenyl)-4,5,6,7-tetrahydro-3H-imidazo[4,5-c]pyridine

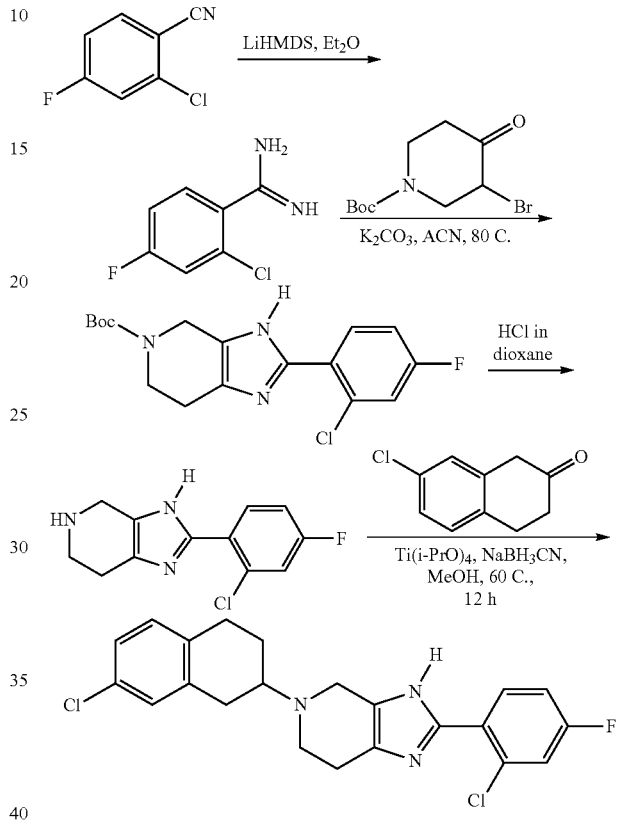

The solution of 2-chloro-4-fluorobenzonitrile (5 g, 32 mmol) in diethyl ether (100 mL) was dropwise added to LiHMDS (1 M in tetrahydrofuran, 64 mL) with stirring under nitrogen atmosphere at 0° C. The resulting solution was stirred at 0° C.~room temperature for 16 hrs. The resulting solution was quenched with 3N hydrochloric acid (100 mL) at 0° C. The water phase was collected, the pH of the water phase was adjusted to 14 with NaOH aqueous, and extracted with ethyl acetate (100 mL×3). The combined organic phases were washed with brine (100 mL), dried over anhydrous $Na_2SO_4$ and evaporated in vacuo. This resulted in 2-chloro-4-fluorobenzimidamide (4.6 g, 84% yield) as a brown solid. MS (ESI): mass calcd. for $C_7H_6ClFN_2$ 172.02, m/z found 172.9 $[M+H]^+$.

The mixture of 2-chloro-4-fluorobenzimidamide (2 g, 11.6 mmol), tert-butyl 3-bromo-4-oxopiperidine-1-carboxylate (3.22 g, 11.6 mmol) and potassium carbonate (1.6 g, 11.6 mmol) in acetonitrile (40 mL) was stirred at 80° C. for 16 hrs. The resulting mixture was evaporated under vacuum and purified by silica column (0-50% ethyl acetate in petroleum ether). This resulted in tert-butyl 2-(2-chloro-4-fluorophenyl)-3,4,6,7-tetrahydro-5H-imidazo[4,5-c]pyridine-5-carboxylate (0.68 g, 17% yield). MS (ESI): mass calcd. for $C_{17}H_{19}ClFN_3O_2$ 351.11, m/z found 351.8 $[M+H]^+$.

The mixture of tert-butyl 2-(2-chloro-4-fluorophenyl)-3,4,6,7-tetrahydro-5H-imidazo[4,5-c]pyridine-5-carboxylate (680 mg, 1.9 mmol) in HCl (g) in dioxane (4 N, 20 mL) was stirred at room temperature for 16 hrs. The resulting mixture was basified by ammonia to free the product, then concentrated to give crude product, which was purified by chromatography on silica gel, eluting (10:1 dichloromethane:methanol) to afford 2-(2-chloro-4-fluorophenyl)-4,5,6,7-tetrahydro-3H-imidazo[4,5-c]pyridine (450 mg, 92% yield) as a yellow solid. MS (ESI): mass calcd. for $C_{12}H_{11}ClFN_3$ 251.06, m/z found 251.9 $[M+H]^+$.

To a solution of 2-(2-chloro-4-fluorophenyl)-4,5,6,7-tetrahydro-3H-imidazo[4,5-c]pyridine (120 mg, 0.48 mmol) and 7-chloro-3,4-dihydronaphthalen-2(1H)-one (87, 0.48 mmol) in methanol (5 mL) was added Ti(i-PrO)$_4$ (273 mg, 0.96 mmol), the resulting mixture was stirred at room temperature under N$_2$ for 1 h, NaBH$_3$CN (151 mg, 2.4 mmol) was added to the reaction mixture and stirred at 60° C. for 16 h. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-$C^{18}$ 150×21.2 mm, 5 μm, mobile phase: acetonitrile-H$_2$O (0.1% FA), gradient: 15-35) to afford 5-(7-chloro-1,2,3,4-tetrahydronaphthalen-2-yl)-2-(2-chloro-4-fluorophenyl)-4,5,6,7-tetrahydro-3H-imidazo[4,5-c]pyridine (41 mg, 21% yield) as white solid. MS (ESI): mass calcd. for $C_{22}H_{20}Cl_2FN_3$ 415.10, m/z found 415.7 $[M+H]^+$, $^1$H NMR (400 MHz, CD$_3$OD) δ ppm 7.73-7.76 (t, J=7.2 Hz, 1H), 7.38-7.41 (m, 1H), 7.20-7.25 (m, 2H), 7.11-7.16 (m, 2H), 4.11-4.19 (m, 2H), 3.37-3.48 (m, 3H), 2.88-3.22 (m, 6H), 2.35-2.38 (m, 1H), 1.86-1.96 (m, 1H).

Example 23: 5-(7-chloro-1,2,3,4-tetrahydronaphthalen-2-yl)-2-(2-chloro-4-methoxyphenyl)-4,5,6,7-tetrahydro-3H-imidazo[4,5-c]pyridine

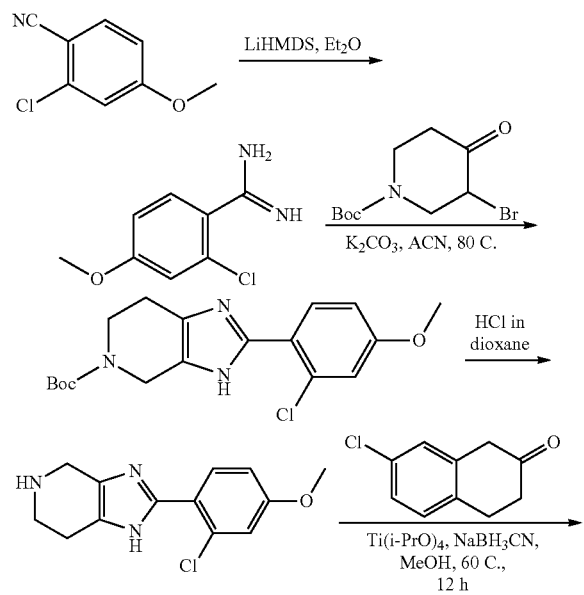

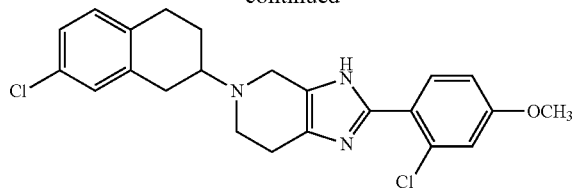

The solution of 2-chloro-4-methoxybenzonitrile (3 g, 18 mmol) in diethyl ether (60 mL) was dropwise added to LiHMDS (1 M in tetrahydrofuran, 36 mL) with stirring under nitrogen atmosphere at 0° C. The resulting solution was stirred at 60° C. for 16 hrs. The resulting solution was quenched with 3N hydrochloric acid (60 mL) at 0° C. The water phase was collected, the pH of the water phase was adjusted to 14 with NaOH aqueous, extracted with ethyl acetate (100 mL×2). The combined organic phases were washed with brine (100 mL), dried over anhydrous Na$_2$SO$_4$ and evaporated in vacuo. This resulted in 2-chloro-4-methoxybenzimidamide (2.4 g, 73% yield) as a brown solid. MS (ESI): mass calcd. for $C_8H_9ClN_2O$ 184.04, m/z found 184.8 $[M+H]^+$.

The mixture of 2-chloro-4-methoxybenzimidamide (2 g, 10.8 mmol), tert-butyl 3-bromo-4-oxopiperidine-1-carboxylate (5.56 g, 10.8 mmol) and potassium carbonate (1.5 g, 10.8 mmol) in acetonitrile (50 mL) was stirred at 80° C. for 16 hrs. The resulting mixture was evaporated under vacuum and purified by silica column (0-50% ethyl acetate in petroleum ether). This resulted in tert-butyl 2-(2-chloro-4-methoxyphenyl)-3,4,6,7-tetrahydro-5H-imidazo[4,5-c]pyridine-5-carboxylate (0.7 g, 18%). MS (ESI): mass calcd. for $C_{18}H_{22}ClN_3O_3$ 363.13, m/z found 363.9 $[M+H]^+$.

The mixture of tert-butyl 2-(2-chloro-4-methoxyphenyl)-3,4,6,7-tetrahydro-5H-imidazo[4,5-c]pyridine-5-carboxylate (700 mg, 1.92 mmol) in HCl (g) in dioxane (4N, 20 mL) was stirred at room temperature for 16 h. The resulting mixture was basified by ammonia to free the product, then concentrated to give crude product, which was purified by chromatography on silica gel, eluting (10:1 dichlorormiethane:methariol) to afford 2-(2-chloro-4-methoxyphenyl)-4,5,6,7-tetrahydro-3H-imidazo[4,5-c]pyridine (380 mg, 75% yield) as a yellow solid. MS (ESI): mass calcd. for $C_{13}H_{14}ClN_3O$ 263.08, m/z found 263.8 $[M+H]^+$.

To a solution of 2-(2-chloro-4-methoxyphenyl)-4,5,6,7-tetrahydro-3H-imidazo[4,5-c]pyridine (130 mg, 0.49 mmol) and 7-chloro-3,4-dihydronaphthalen-2(1H)-one (89 mg, 0.49 mmol) in methanol (5 mL) was added Ti(i-PrO)$_4$ (279 mg, 0.98 mmol), the resulting mixture was stirred at room temperature under N$_2$ for 1 h, NaBH$_3$CN (154 mg, 2.45 mmol) was added to the reaction mixture and stirred at 60° C. for 16 h. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-$C^{18}$ 150×21.2 mm, 5 μm, mobile phase: acetonitrile-H$_2$O (0.1% FA), gradient: 20-70) to afford 5-(7-chloro-1,2,3,4-tetrahydronaphthalen-2-yl)-2-(2-chloro-4-methoxyphenyl)-4,5,6,7-tetrahydro-3H-imidazo[4,5-c]pyridine (23 mg, 11% yield) as white solid. MS (ESI): mass calcd. for $C_{23}H_{23}Cl_2N_3O$ 427.12, m/z found 427.9 $[M+H]^+$, $^1$H NMR (400 MHz, CD$_3$OD) δ ppm 8.44 (s, 1H), 7.61-7.64 (d, J=8.8 Hz, 1H), 7.00-7.20 (m, 5H), 4.06-4.14

(m, 2H), 3.87 (s, 3H), 3.38-3.44 (m, 3H), 2.88-3.26 (m, 6H), 2.34-2.36 (m, 1H), 1.87-1.91 (m, 1H).

Example 24: 5-(7-chloro-1,2,3,4-tetrahydronaphthalen-2-yl)-2-(2-chloro-5-methoxyphenyl)-4,5,6,7-tetrahydro-3H-imidazo[4,5-c]pyridine

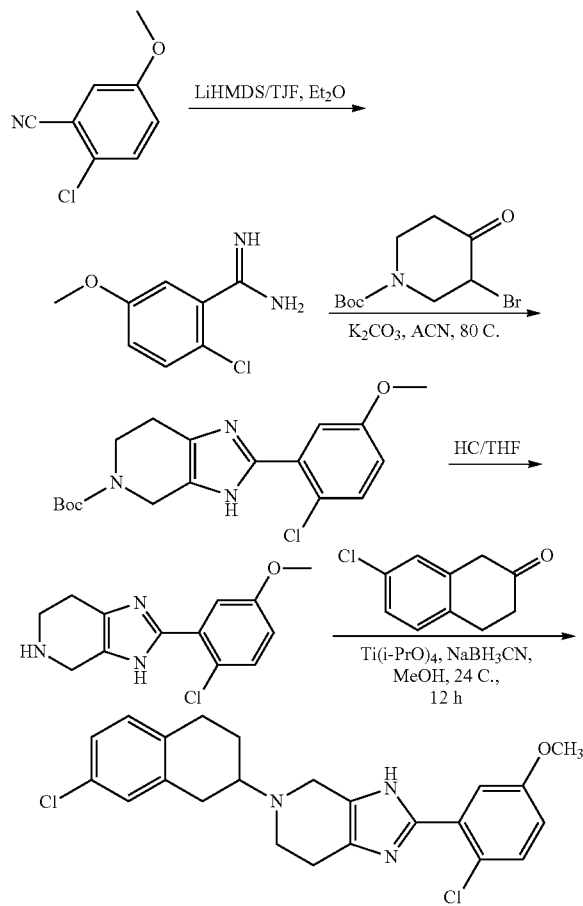

To a solution of 2-chloro-5-methoxybenzonitrile (5 g, 30 mmol) in ether (200 mL) was added dropwise LHMDS/tetrahydrofuran aqueous. (1 N, 60 mL, 60 mmol) at 0° C. The solution was stirred at room temperature for 15 hrs. After the reaction finished, ice water (100 mL) was added. The solution was adjusted pH to 3-4 with 3N HCl aqueous. The mixture was extracted with dichloromethane (100 mL×2). The aqueous phase was adjusted pH to 9-10 with sodium hydroxide solid. The mixture was extracted with dichloromethane (100 mL×3). The combined organic phases were dried with anhydrous sodium sulfate. Filtered. The filtrate was concentrated to give 2-chloro-5-methoxybenzimidamide (5 g, 91% yield) as a yellow solid. MS (ESI): mass calcd. for $C_8H_9ClN_2O$ 186.62, m/z found 184.9 $[M+H]^+$.

To a solution of 2-chloro-5-methoxybenzimidamide (3 g, 16 mmol), potassium carbonate (2.25 g, 16 mmol) in acetonitrile (50 mL) was added tert-butyl 3-bromo-4-oxopiperidine-1-carboxylate (4.5 g, 16 mmol). The solution was stirred at 80° C. for 15 hrs. After the reaction finished, ice water (50 mL) was added. The solution was extracted with dichloromethane (50 mL×3). The combined organic phases were concentrated and the residue was purified by Combi-Flash (silica column, 12 g, petroleum ether:ethyl acetate=5:1) to give tert-butyl 2-(2-chloro-5-methoxyphenyl)-3,4,6,7-tetrahydro-5H-imidazo[4,5-c]pyridine-5-carboxylate (2.5 g, 42% yield) as a white solid. MS (ESI): mass calcd. for $C_{18}H_{22}ClN_3O_3$ 363.84, m/z found 363.8 $[M+H]^+$.

To a solution of tert-butyl 2-(2-chloro-5-methoxyphenyl)-3,4,6,7-tetrahydro-5H-imidazo[4,5-c]pyridine-5-carboxylate (2.5 g, 6.8 mmol) in tetrahydrofuran (30 mL) was added HCl/tetrahydrofuran aqueous (30 mL). The solution was stirred at room temperature for 15 hrs. After the reaction was finished, the solution was adjusted pH to 13-14 with 3N NaOH aqueous. The solution was extracted with dichloromethane (50 mL×3). The combined organic phases were concentrated and the residue was purified by Combi-Flash (silica column, 12 g, dichloromethane:methanol=20:1) to give 2-(2-chloro-5-methoxyphenyl)-4,5,6,7-tetrahydro-3H-imidazo[4,5-c]pyridine (1.1 g, 61% yield) as a yellow solid. MS (ESI): mass calcd. for $C_{13}H_{14}ClN_3O$ 263.73, m/z found 263.9 $[M+H]^+$.

To a solution of 2-(2-chloro-5-methoxyphenyl)-4,5,6,7-tetrahydro-3H-imidazo[4,5-c]pyridine (180 mg, 0.68 mmol), 7-chloro-3,4-dihydronaphthalen-2(1H)-one (123 mg, 0.68 mmol), Ti(OiPr)$_4$ (386 mg, 1.36 mmol) in methanol (30 mL) was added NaBH$_3$CN (248 mg, 4 mmol). The solution was stirred at room temperature for 15 hrs. After the reaction was finished, ice water (30 mL) was added. The solution was extracted with dichloromethane (30 mL×3). The combined organic phases were concentrated and the residue was purified by prep-HPLC (Gemini-C$^{18}$ 150×21.2 mm, 5 µm, mobile phase: acetonitrile-H$_2$O (0.1% formic acid), gradient: 15-40) to give 5-(7-chloro-1,2,3,4-tetrahydronaphthalen-2-yl)-2-(2-chloro-5-)-4,5,6,7-tetrahydro-3H-imidazo[4,5-c]pyridine (93.1 mg, 31% yield) as a white solid. MS (ESI): mass calcd. for $C_{23}H_{23}Cl_2N_3O$ 428.36, m/z found 427.7 $[M+H]^+$, $^1$H NMR (400 MHz, DMSO-d$_6$) δ ppm 11.95 (s, 1H), 8.16 (s, 1H), 7.41 (d, J=8.8 Hz, 1H), 7.32 (s, 1H), 7.20 (s, 1H), 7.12 (q, J=8.1 Hz, 2H), 6.94 (dd, J=8.8, 2.9 Hz, 1H), 3.79 (s, 3H), 3.63 (s, 2H), 2.89 (m, J=25.0, 14.1, 8.2 Hz, 7H), 2.65 (s, 2H), 2.05 (d, J=11.6 Hz, 1H), 1.75 (s, 1H).

Example 25: 2-(2-chlorophenyl)-5-(6,8-dichloro-1,2,3,4-tetrahydronaphthalen-2-yl)-4,5,6,7-tetrahydro-3H-imidazo[4,5-c]pyridine

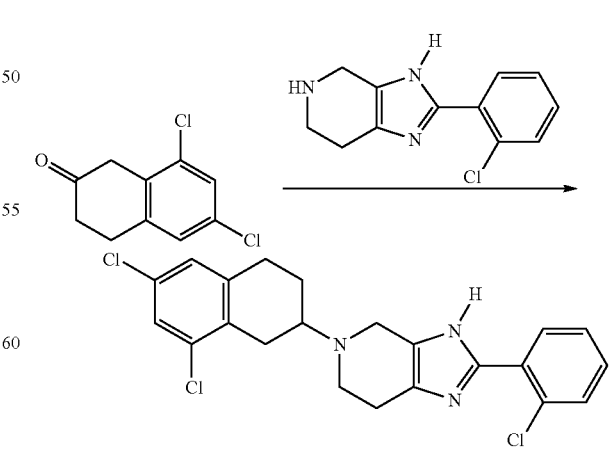

A mixture of 6,8-dichloro-3,4-dihydronaphthalen-2(1H)-one (129 mg, 0.6 mmol), 2-(2-chlorophenyl)-4,5,6,7-tetrahydro-3H-imidazo[4,5-c]pyridine (117 mg, 0.5 mmol), NaBH₃CN (66 mg, 1 mmol) and molecular sieve in 0.35% HCl-methanol (3 mL) and tetrahydrofuran (2 mL) was stirred at room temperature for 16 hours. The reaction solution was filtered and the filtrate was concentrated and purified by prep-HPLC to afford 2-(2-chlorophenyl)-5-(6,8-dichloro-1,2,3,4-tetrahydronaphthalen-2-yl)-4,5,6,7-tetrahydro-3H-imidazo[4,5-c]pyridine (30 mg, 12% yield) as white solid. MS (ESI): mass calcd. for $C_{22}H_{20}Cl_3N_3$ 431.07, m/z found 431.7 $[M+H]^+$. ¹H NMR (400 MHz, CD₃OD) δ ppm 8.31 (m, 1H), 7.55 (m, 1H), 7.46-7.41 (m, 2H), 7.33 (s, 1H), 7.18 (s, 1H), 4.18 (m, 2H), 3.47 (m, 2H), 3.37 (m, 1H), 3.28 (m, 1H), 3.01-2.86 (m, 5H), 2.37 (m, 1H), 1.92-1.82 (m, 1H).

Example 26: 5-(8-bromo-1,2,3,4-tetrahydronaphthalen-2-yl)-2-(2-chlorophenyl)-4,5,6,7-tetrahydro-3H-imidazo[4,5-c]pyridine

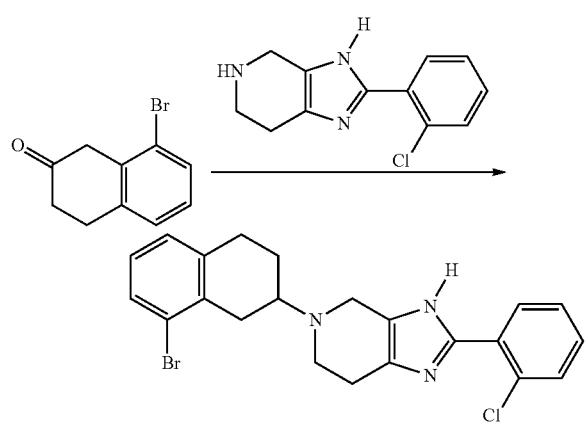

A mixture of 8-bromo-3,4-dihydronaphthalen-2(1H)-one (135 mg, 0.6 mmol), 2-(2-chlorophenyl)-4,5,6,7-tetrahydro-3H-imidazo[4,5-c]pyridine (117 mg, 0.5 mmol), NaBH3CN (63 mg, 1 mmol) and 4 A molecular sieve in 0.04 N HCl-methanol (3 mL) was stirred at room temperature for 16 hours. The reaction solution was filtered and the filtrate was concentrated and purified by prep-HPLC to afford 5-(8-bromo-1,2,3,4-tetrahydronaphthalen-2-yl)-2-(2-chlorophenyl)-4,5,6,7-tetrahydro-3H-imidazo[4,5-c]pyridine (10 mg, 4% yield) as white solid. MS (ESI): mass calcd. for $C_{22}H_{21}BrClN_3$ 441.06, m/z found 441.7, 443.6 $[M+H]^+$. ¹H NMR (400 MHz, CD₃OD) δ ppm 8.36 (bs, 1H), 7.33 (m, 1H), 7.55 (m, 1H), 7.45 (m, 3H), 7.15 (d, J=8 Hz, 1H), 7.08 (t, J=8 Hz, 1H), 4.15 (q, J=20 Hz, 16 Hz, 2H), 3.47 (m, 2H), 3.32 (m, 2H), 3.05-2.88 (m, 5H), 2.36 (m, 1H), 1.85 (m, 1H).

Example 27: 5-(7-bromo-1,2,3,4-tetrahydronaphthalen-2-yl)-2-(2-chlorophenyl)-4,5,6,7-tetrahydro-3H-imidazo[4,5-c]pyridine

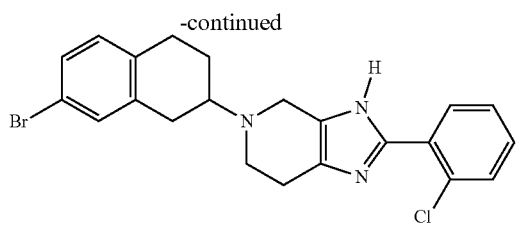

To a solution of 2-(2-chlorophenyl)-4,5,6,7-tetrahydro-3H-imidazo[4,5-c]pyridine (234 mg, 0.1 mmol) and 7-bromo-3,4-dihydronaphthalen-2(1H)-one (225 mg, 0.1 mmol) in methanol (10 mL) was added Ti(i-PrO)₄ (568 mg, 0.2 mmol), the resulting mixture was stirred at room temperature under N₂ for 1 h, NaBH₃CN (314 mg, 0.5 mmol) was added to the reaction mixture and stirred at 60° C. for 16 hrs. After the reaction was finished, it was quenched with H₂O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C¹⁸ 150×21.2 mm, 5 μm, mobile phase: acetonitrile-H₂O (0.1% formic acid), gradient: 20-40) to afford 5-(7-bromo-1,2,3,4-tetrahydronaphthalen-2-yl)-2-(2-chlorophenyl)-4,5,6,7-tetrahydro-3H-imidazo[4,5-c]pyridine (115 mg, 26% yield) as white solid. MS (ESI): mass calcd. for $C_{22}H_{21}BrClN_3$ 441.06, m/z found 441.7 $[M+H]^+$, ¹H NMR (400 MHz, CD₃OD) δ ppm 8.35 (s, 1H), 7.71-7.74 (m, 1H), 7.54-7.57 (m, 1H), 7.43-7.45 (m, 2H), 7.36 (s, 1H), 7.28-7.31 (m, 1H), 7.26-7.08 (d, J=8.4 Hz, 1H) 4.15-4.23 (m, 2H), 3.40-3.52 (m, 3H), 3.19-3.24 (m, 1H), 2.98-3.12 (m, 4H), 2.85-2.93 (m, 1H), 2.36-2.39 (m, 1H), 1.90-1.96 (m, 1H).

Example 28: 2-(2-bromophenyl)-5-(7-chloro-1,2,3,4-tetrahydronaphthalen-2-yl)-4,5,6,7-tetrahydro-3H-imidazo[4,5-c]pyridine

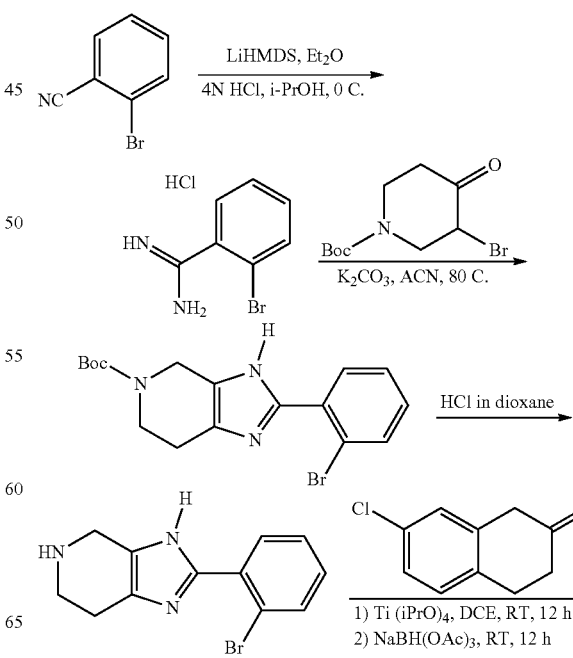

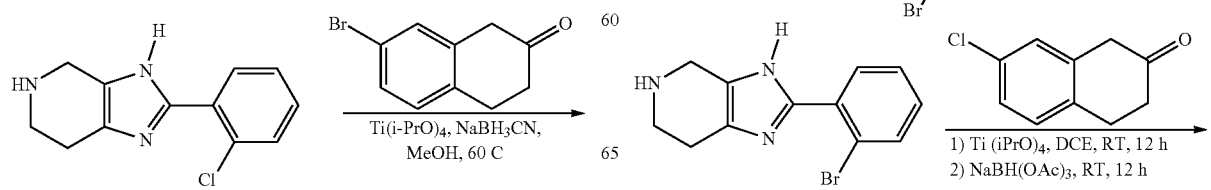

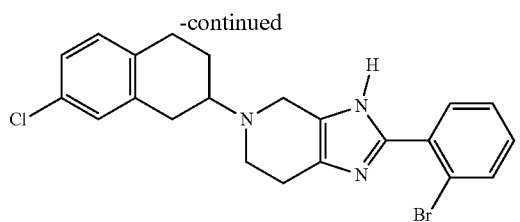

To a solution of 2-bromobenzonitrile (10 g, 54.9 mmol) in tetrahydrofuran (100 ml) was added LiHMDS (55 mL, 55 mmol) at 0° C. The reaction solution was stirred at room temperature for 4 hours. 4 N HCl in dioxane (15 mL) was added, follow by i-propanol (20 mL). The mixture was kept at 0° C. The precipitated was filtered, washed with Et$_2$O (50 mL) to afford 2-bromobenzimidamide hydrochloride (12 g, 92% yield) as white solid. MS (ESI): mass calcd. for C$_7$H$_8$BrClN$_2$ 235.51, m/z found 198.8, 200.8 [M+H]$^+$.

A mixture of 2-bromobenzimidamide hydrochloride (4.71 g, 20 mmol), tert-butyl 3-bromo-4-oxopiperidine-1-carboxylate (5.57 g, 20 mmol) and K$_2$CO$_3$ (4.14 g, 30 mmol) in acetonitrile (60 mL) was heated to reflux for 12 hours. The reaction was cooled and filtered. The filtrate was concentrated and purified on silica gel column (ethyl acetate) to afford tert-butyl 2-(2-bromophenyl)-3,4,6,7-tetrahydro-5H-imidazo[4,5-c]pyridine-5-carboxylate (3.8 g, 50% yield) as white solid. MS (ESI): mass calcd. for C$_{17}$H$_{20}$BrN$_3$O$_2$ 378.27, m/z found 377.8, 379.7 [M+H]$^+$.

tert-butyl 2-(2-bromophenyl)-3,4,6,7-tetrahydro-5H-imidazo[4,5-c]pyridine-5-carboxylate (3.8 g, 10 mmol) was dissolved in HCl-Dioxane (10 mL, 40 mmol). The mixture was stirred at room temperature for 2 hours. The reaction was concentrated and the residue was dissolved in a solution of ethanol (20 mL) and water (5 mL). The pH was adjusted to 8. The mixture was concentrated and purified on silica gel column (10:1 dichloromethane:methanol) to afford 2-(2-bromophenyl)-4,5,6,7-tetrahydro-3H-imidazo[4,5-c]pyridine (2.2 g, 79% yield) as white solid. MS (ESI): mass calcd. for C$_{12}$H$_{12}$BrN$_3$ 278.15, m/z found 277.8, 279.8 [M+H]$^+$.

To a solution of 2-(2-bromophenyl)-4,5,6,7-tetrahydro-3H-imidazo[4,5-c]pyridine (500 mg, 1.78 mmol), 7-chloro-3,4-dihydronaphthalen-2(1H)-one (324 mg, 1.8 mmol) in 1,2-dichloroethane (30 mL) was added Ti(iPrO)$_4$ (759 mg, 2.67 mmol). The mixture was stirred at room temperature for 12 hours. NaBH(OAc)$_3$ was added. The reaction solution was stirred at room temperature for 12 hours. The reaction was quenched with water (60 mL), extracted with ethyl acetate (30 mL×3). The combined organic layers were washed with sat. NaHCO$_3$ solution (30 mL), water (30 mL), brine (30 mL), dried, concentrated and purified on silica gel column (10:1 dichloromethane:methanol) to afford 2-(2-bromophenyl)-5-(7-chloro-1,2,3,4-tetrahydronaphthalen-2-yl)-4,5,6,7-tetrahydro-3H-imidazo[4,5-c]pyridine (260 mg, 32%) as yellow solid. 90 mg product was purified by prep-HPLC to afford 2-(2-bromophenyl)-5-(7-chloro-1,2,3,4-tetrahydronaphthalen-2-yl)-4,5,6,7-tetrahydro-3H-imidazo[4,5-c]pyridine (11.3 mg, 12% yield) as white solid. MS (ESI): mass calcd. for C$_{22}$H$_{21}$BrClN$_3$ 442.79, m/z found 441.7 [M+H]$^+$. $^1$H NMR (400 MHz, CD$_3$OD) δ ppm 8.32 (s, 1H), 7.75 (dd, J=8.0, 1.0 Hz, 1H), 7.62 (dd, J=7.7, 1.7 Hz, 1H), 7.48 (td, J=7.6, 1.2 Hz, 1H), 7.38 (td, J=7.8, 1.7 Hz, 1H), 7.21 (s, 1H), 7.15 (p, J=8.3 Hz, 2H), 4.28-4.12 (m, 2H), 3.61-3.38 (m, 3H), 3.22 (dd, J=15.9, 4.8 Hz, 1H), 3.15-3.09 (m, 1H), 3.08-2.99 (m, 3H), 2.98-2.86 (m, 1H), 2.43-2.34 (m, 1H), 1.99-1.87 (m, 1H).

Example 29: 2-(4-bromo-2-chlorophenyl)-5-(7-chloro-1,2,3,4-tetrahydronaphthalen-2-yl)-4,5,6,7-tetrahydro-3H-imidazo[4,5-c]pyridine

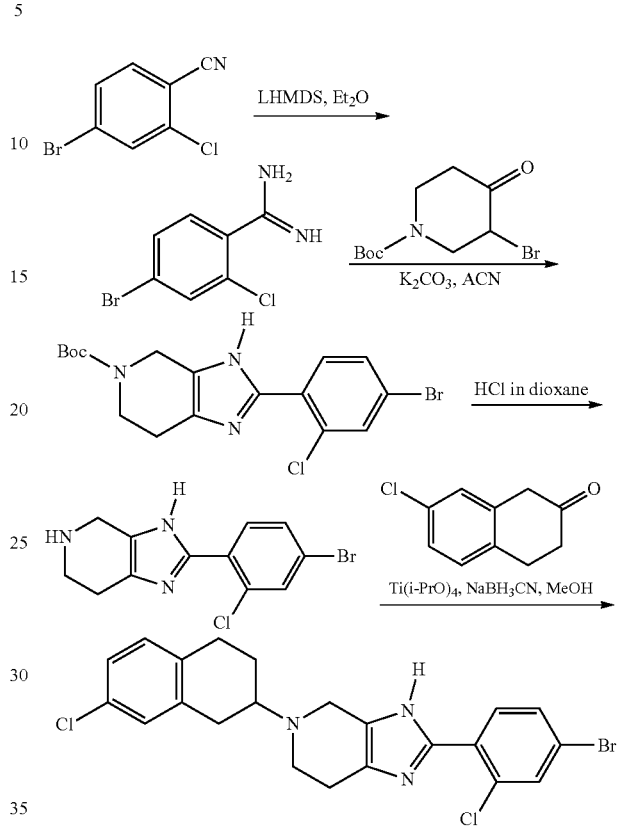

The solution of 4-bromo-2-chlorobenzonitrile (10 g, 46 mmol) in diethyl ether (100 mL) was dropwise added to LiHMDS (1 M in tetrahydrofuran, 92 mL) with stirring under nitrogen atmosphere at 0° C. The resulting solution was stirred at 0° C. to room temperature for 16 h. The resulting solution was quenched with 3N hydrochloric acid (100 mL) at 0° C. The water phase was collected, the pH of the water phase was adjusted to 14 with NaOH aqueous, and extracted with ethyl acetate (100 mL×2). The combined organic phases were washed with brine (100 mL), dried over anhydrous Na$_2$SO$_4$ and evaporated in vacuo. This resulted in 4-bromo-2-chlorobenzimidamide (9.6 g, 89% yield) as a brown solid. MS (ESI): mass calcd. for C$_7$H$_6$BrClN$_2$ 231.94, m/z found 232.7 [M+H]$^+$.

The mixture of 4-bromo-2-chlorobenzimidamide (8 g, 34 mmol), tert-butyl 3-bromo-4-oxopiperidine-1-carboxylate (9.45 g, 34 mmol) and potassium carbonate (4.7 g, 34 mmol) in acetonitrile (80 mL) was stirred at 80° C. for 16 h. The resulting mixture was evaporated under vacuum and purified by silica column (0-50% ethyl acetate in petroleum ether). This resulted in tert-butyl 2-(4-bromo-2-chlorophenyl)-3,4,6,7-tetrahydro-5H-imidazo[4,5-c]pyridine-5-carboxylate (3.8 g, 27% yield). MS (ESI): mass calcd. for C$_{17}$H$_{19}$BrClN$_3$O$_2$ 411.03, m/z found 411.8 [M+H]$^+$.

The mixture of tert-butyl 2-(4-bromo-2-chlorophenyl)-3,4,6,7-tetrahydro-5H-imidazo[4,5-c]pyridine-5-carboxylate (3.8 g, 9.2 mmol) in HCl (g) in dioxane (4 N, 50 mL) was stirred at room temperature for 16 h. The resulting mixture was basified by ammonia to free the product, then concentrated to give crude product, which was purified by chromatography on silica gel, eluting (10:1 dichloromethane:methanol) to afford 2-(4-bromo-2-chlorophenyl)-4,5,6,7-tetrahydro-3H-imidazo[4,5-c]pyridine (2.1 g, 76% yield) as a yellow solid. MS (ESI): mass calcd. for $C_{12}H_{11}BrClN_3$ 310.98, m/z found 311.7 $[M+H]^+$.

To a solution of 2-(4-bromo-2-chlorophenyl)-4,5,6,7-tetrahydro-3H-imidazo[4,5-c]pyridine (150 mg, 0.48 mmol) and 7-chloro-3,4-dihydronaphthalen-2(1H)-one (87 mg, 0.48 mmol) in methanol (5 mL) was added Ti(i-PrO)$_4$ (273 mg, 0.96 mmol), the resulting mixture was stirred at room temperature under N$_2$ for 1 h, NaBH$_3$CN (151 mg, 2.4 mmol) was added to the reaction mixture and stirred at 60° C. for 16 h. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 20-60) to afford 2-(4-bromo-2-chlorophenyl)-5-(7-chloro-1,2,3,4-tetrahydronaphthalen-2-yl)-4,5,6,7-tetrahydro-3H-imidazo[4,5-c]pyridine (48 mg, 21% yield) as white solid. MS (ESI): mass calcd. for $C_{22}H_{20}BrCl_2N_3$ 475.02, m/z found 475.6 $[M+H]^+$, $^1$H NMR (400 MHz, CD$_3$OD) δ ppm 8.32 (s, 1H), 7.78-7.79 (m, 1H), 7.60-7.66 (s, 2H), 7.20 (s, 1H), 7.11-7.16 (m, 2H), 4.14-4.19 (m, 2H), 3.38-3.50 (m, 3H), 2.88-3.22 (m, 6H), 2.35-2.38 (m, 1H), 1.87-1.96 (m, 1H).

Example 30: 2-(5-bromo-2-chlorophenyl)-5-(7-chloro-1,2,3,4-tetrahydronaphthalen-2-yl)-4,5,6,7-tetrahydro-3H-imidazo[4,5-c]pyridine

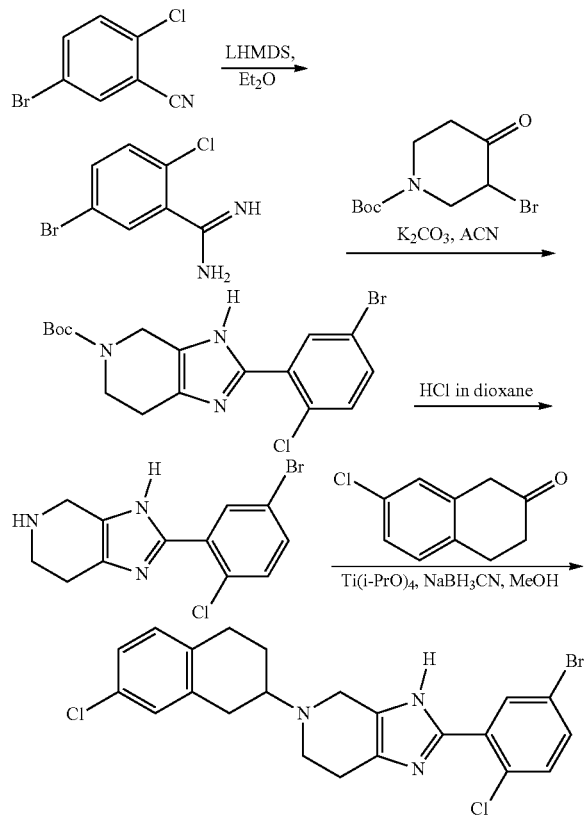

The solution of 5-bromo-2-chlorobenzonitrile (10 g, 46 mmol) in diethyl ether (100 mL) was dropwise added to LiHMDS (1 M in tetrahydrofuran, 92 mL) with stirring under nitrogen atmosphere at 0° C. The resulting solution was stirred at 0° C.~room temperature for 16 h. The resulting solution was quenched with 3N hydrochloric acid (100 mL) at 0° C. The water phase was collected, the pH of the water phase was adjusted to 14 with NaOH aqueous, extracted with ethyl acetate (100 mL×3). The combined organic phases were washed with brine (100 mL), dried over anhydrous Na$_2$SO$_4$ and evaporated in vacuo. This resulted in 5-bromo-2-chlorobenzimidamide (13 g, 89% yield) as a brown solid. MS (ESI): mass calcd. for $C_7H_6BrClN_2$ 231.94, m/z found 232.7 $[M+H]^+$.

The mixture of 5-bromo-2-chlorobenzimidamide (8 g, 34 mmol), tert-butyl 3-bromo-4-oxopiperidine-1-carboxylate (9.5 g, 34 mmol) and potassium carbonate (4.7 g, 34 mmol) in acetonitrile (40 mL) was stirred at 80° C. for 16 h. The resulting mixture was evaporated under vacuum and purified by silica column (0-50% ethyl acetate in petroleum ether). This resulted in tert-butyl 2-(5-bromo-2-chlorophenyl)-3,4,6,7-tetrahydro-5H-imidazo[4,5-c]pyridine-5-carboxylate (2.5 g, 25% yield). MS (ESI): mass calcd. for $C_{17}H_{19}BrClN_3O_2$ 411.03, m/z found 411.7 $[M+H]^+$.

The mixture of tert-butyl 2-(5-bromo-2-chlorophenyl)-3,4,6,7-tetrahydro-5H-imidazo[4,5-c]pyridine-5-carboxylate (3.5 g, 8.5 mmol) in HCl (g) in dioxane (4 N, 50 mL) was stirred at room temperature for 16 h. The resulting mixture was basified by ammonia to free the product, then concentrated to give crude product, which was purified by chromatography on silica gel, eluting (10:1 dichloromethane:methanol) to afford 2-(5-bromo-2-chlorophenyl)-4,5,6,7-tetrahydro-3H-imidazo[4,5-c]pyridine (2.4 g, 90% yield) as a yellow solid. MS (ESI): mass calcd. for $C_{12}H_{11}BrClN_3$ 310.98, m/z found 311.7 $[M+H]^+$.

To a solution of 2-(5-bromo-2-chlorophenyl)-4,5,6,7-tetrahydro-3H-imidazo[4,5-c]pyridine (160 mg, 0.51 mmol) and 7-chloro-3,4-dihydronaphthalen-2(1H)-one (93 mg, 0.51 mmol) in methanol (5 mL) was added Ti(i-PrO)$_4$ (290 mg, 1.02 mmol), the resulting mixture was stirred at room temperature under N$_2$ for 1 h, NaBH$_3$CN (160 mg, 2.55 mmol) was added to the reaction mixture and stirred at 60° C. for 16 h. After the reaction was finished, it was quenched with H$_2$O and filtered, the solid was washed with dichloromethane, the water phase and organic phase was combined and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 20-50) to afford 2-(5-bromo-2-chlorophenyl)-5-(7-chloro-1,2,3,4-tetrahydronaphthalen-2-yl)-4,5,6,7-tetrahydro-3H-imidazo[4,5-c]pyridine (44 mg, 18% yield) as white solid. MS (ESI): mass calcd. for $C_{22}H_{20}BrCl_2N_3$ 475.02, m/z found 475.6 $[M+H]^+$, $^1$H NMR (400 MHz, CD$_3$OD) δ ppm 8.05 (s, 1H), 7.84-7.87 (m, 1H), 7.65-7.67 (d, J=8.4 Hz, 1H), 7.27 (s, 1H), 7.18-7.22 (m, 2H), 4.70-4.79 (m, 2H), 4.01-4.11 (m, 3H), 3.26-3.44 (m, 4H), 2.96-3.13 (m, 2H), 2.54-2.58 (m, 1H), 2.08-2.13 (m, 1H).

Example 31: 2-(2-chlorophenyl)-5-(6-cyclopropyl-1,2,3,4-tetrahydronaphthalen-2-yl)-4,5,6,7-tetrahydro-3H-imidazo[4,5-c]pyridine

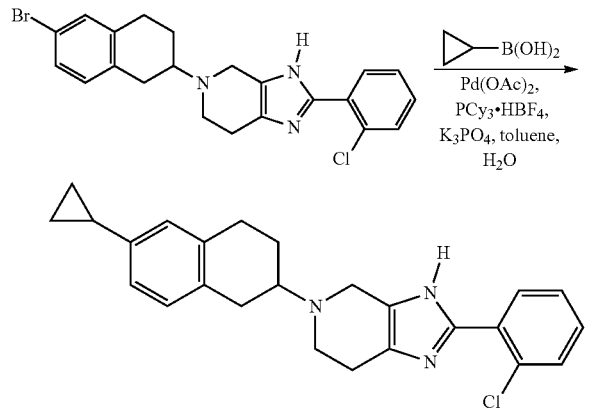

A mixture of 5-(6-bromo-1,2,3,4-tetrahydronaphthalen-2-yl)-2-(2-chlorophenyl)-4,5,6,7-tetrahydro-3H-imidazo[4,5-c]pyridine (111 mg, 0.25 mmol), cyclopropylboronic acid (43 mg, 05 mmol), Pd(OAc)$_2$ (11 mg, 0.05 mmol), PCy$_3$·HBF$_4$ (37 mg, 01 mmol) and K$_3$PO$_4$ (159 mg, 0.75 mmol) in toluene (5 mL) was stirred at 100° C. for 16 hours under nitrogen atmosphere. The reaction mixture was cooled and filtered through celite. The filtrate was concentrated and purified by prep-HPLC to afford 2-(2-chlorophenyl)-5-(6-cyclopropyl-1,2,3,4-tetrahydronaphthalen-2-yl)-4,5,6,7-tetrahydro-3H-imidazo[4,5-c]pyridine (25 mg, 22% yield) as white solid. MS (ESI): mass calcd. for $C_{25}H_{26}ClN_3$ 403.18, m/z found 403.8 [M+H]$^+$. $^1$H NMR (400 MHz, CD$_3$OD) δ ppm 8.41 (s, 1H), 7.72 (m, 1H), 7.54 (m, 1H), 7.44 (m, 2H), 7.06 (m, 1H), 6.88 (m, 2H), 4.26 (m, 2H), 3.56 (m, 3H), 3.18 (m, 1H), 3.06-2.88 (m, 5H), 2.39 (m, 1H), 1.93-1.83 (m, 2H), 0.93 (m, 2H), 0.65 (m, 2H).

Example 32: 2-(2-chlorophenyl)-5-(6-(4-methyl-1H-imidazol-1-yl)-1,2,3,4-tetrahydronaphthalen-2-yl)-4,5,6,7-tetrahydro-3H-imidazo[4,5-c]pyridine

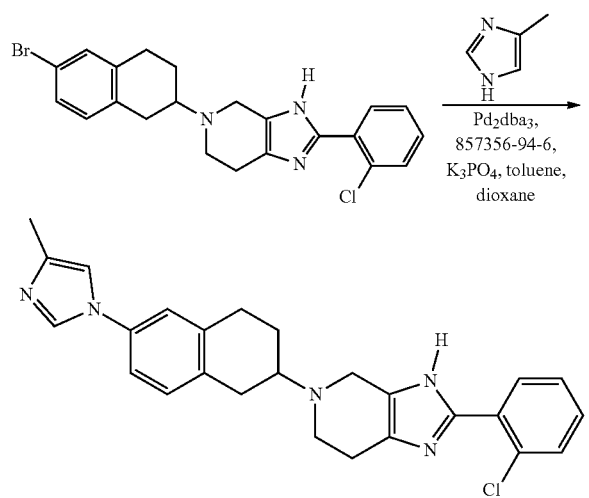

To 25 ml round bottom flask was added Pd$_2$(dba)$_3$ (92 mg, 0.1 mmol) and Ligand (115 mg, 0.24 mmol). The flask was evacuated and backfilled with nitrogen for 3 times. Anhydrous toluene (2 mL) and dioxane (0.4 mL) were added. The mixture was stirred at 120° C. for 3 mins. A second 25 mL flask was charged with 5-(6-bromo-1,2,3,4-tetrahydronaphthalen-2-yl)-2-(2-chlorophenyl)-4,5,6,7-tetrahydro-3H-imidazo[4,5-c]pyridine (222 mg, 0.5 mmol), 4-methyl-1H-imidazole (49 mg, 0.6 mmol) and K$_3$PO$_4$ (212 mg, 1 mmol). The second flask was evacuated and backfilled with nitrogen for 3 times. The preheated catalyst solution was added to the second flask. The reaction mixture was heated to 120° C. for 15 hours. The reaction mixture was cooled and filtered through celite. The filtrate was concentrated and purified by prep-HPLC to afford 2-(2-chlorophenyl)-5-(6-(4-methyl-1H-imidazol-1-yl)-1,2,3,4-tetrahydronaphthalen-2-yl)-4,5,6,7-tetrahydro-3H-imidazo[4,5-c]pyridine (5 mg, 2% yield) as white solid. MS (ESI): mass calcd. for $C_{26}H_{26}ClN_5$ 443.19, m/z found 443.8 [M+H]$^+$. $^1$H NMR (400 MHz, CD$_3$OD) δ ppm 8.32 (bs, 1H), 8.16 (s, 1H), 7.55 (m, 1H), 7.48-7.42 (m, 1H), 7.43-7.42 (m, 2H), 7.31 (m, 4H), 4.33 (m, 2H), 3.64-3.55 (m, 3H), 3.22-3.01 (m, 6H), 2.44 (m, 1H), 2.21 (s, 3H), 2.02 (m, 1H).

Example 33: methyl 2-(2-(2-chlorophenyl)-5-(8-methoxy-1,2,3,4-tetrahydronaphthalen-2-yl)-4,5,6,7-tetrahydro-3H-imidazo[4,5-c]pyridin-3-yl)acetate

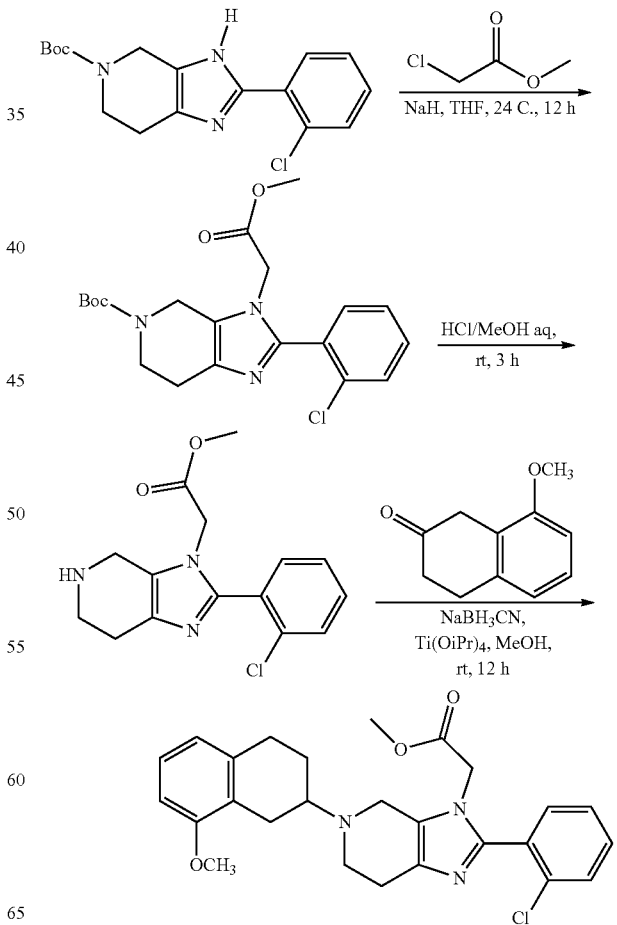

To a solution of tert-butyl 2-(2-chlorophenyl)-3,4,6,7-tetrahydro-5H-imidazo[4,5-c]pyridine-5-carboxylate (2 g, 6 mmol) in tetrahydrofuran (30 mL) was added sodium hydride (360 mg, 9 mmol) at 0° C. The solution was stirred at room temperature for 1.5 hours. Methyl 2-chloroacetate (640 mg, 6 mmol) was added. The solution was stirred at room temperature for 15 hours. After the reaction done, ice water (100 mL) was added. The mixture was extracted with dichloromethane (100 mL×3). The combined organic phases were concentrated and the residue was purified by Combi-Flash (silica column, 12 g, petroleum ether:ethyl acetate=20:1) to give the compound tert-butyl 2-(2-chlorophenyl)-3-(2-methoxy-2-oxoethyl)-3,4,6,7-tetrahydro-5H-imidazo[4,5-c]pyridine-5-carboxylate and tert-butyl 2-(2-chlorophenyl)-1-(2-methoxy-2-oxoethyl)-1,4,6,7-tetrahydro-5H-imidazo[4,5-c]pyridine-5-carboxylate (1.5 g, 60% yield) as a white solid. MS (ESI): mass calcd. for $C_{20}H_{24}ClN_3O_4$ 405.88, m/z found 405.8 $[M+H]^+$.

To a solution of tert-butyl 2-(2-chlorophenyl)-3-(2-methoxy-2-oxoethyl)-3,4,6,7-tetrahydro-5H-imidazo[4,5-c]pyridine-5-carboxylate (1.5 g, 3.7 mmol) in tetrahydrofuran (30 mL) was added HCl/tetrahydrofuran aqueous (30 mL). The solution was stirred at room temperature for 15 hrs. After the reaction done, the solution was adjusted pH to 8-9 with 3N NaOH aqueous. The solution was extracted with dichloromethane (50 mL×3). The combined organic phases were concentrated and the residue was purified to give methyl 2-(2-(2-chlorophenyl)-4,5,6,7-tetrahydro-3H-imidazo[4,5-c]pyridin-3-yl)acetate (320 mg, 30% yield) as a yellow solid. MS (ESI): mass calcd. for $C_{15}H_{16}ClN_3O_2$ 305.76, m/z found 305.9 $[M+H]+$.

To a solution of methyl 2-(2-(2-chlorophenyl)-4,5,6,7-tetrahydro-3H-imidazo[4,5-c]pyridin-3-yl)acetate (300 mg, 1 mmol), 8-methoxy-3,4-dihydronaphthalen-2(1H)-one (176 mg, 1 mmol), Ti(OiPr)$_4$ (568 mg, 2 mmol) in methanol (30 mL) was added NaBH$_3$CN (310 mg, 5 mmol). The solution was stirred at room temperature for 15 hrs. After the reaction done, ice water (30 mL) was added. The solution was extracted with dichloromethane (50 mL×3). The combined organic phases were concentrated to give the crude product (250 mg, 85% pure, 74% yield). 120 mg crude was purified by prep-HPLC (Gemini-C$^{18}$ 150×21.2 mm, 5 µm, mobile phase: acetonitrile-H$_2$O (0.1% formic acid), gradient: 20-70) to give methyl 2-(2-(2-chlorophenyl)-5-(8-methoxy-1,2,3,4-tetrahydronaphthalen-2-yl)-4,5,6,7-tetrahydro-3H-imidazo[4,5-c]pyridin-3-yl)acetate (2.4 mg) as a white solid. MS (ESI): mass calcd. for $C_{26}H_{28}ClN_3O_3$ 465.98, m/z found 465.8 $[M+H]^+$, $^1$H NMR (400 MHz, DMSO-d$_6$) δ ppm 8.39 (s, 0.5H), 7.64-7.52 (m, 2H), 7.51-7.39 (m, 2H), 7.12 (t, J=7.9 Hz, 1H), 6.76 (dd, J=12.7, 7.9 Hz, 2H), 4.66 (s, 2H), 4.14 (s, 2H), 3.85 (s, 3H), 3.71 (s, 3H), 3.42 (d, J=4.6 Hz, 1H), 3.41 (s, 1H), 3.26 (d, J=16.1 Hz, 1H), 3.05-2.86 (m, 4H), 2.72 (dd, J=15.8, 11.0 Hz, 1H), 2.33 (d, J=11.7 Hz, 1H), 1.84 (td, J=11.9, 5.2 Hz, 1H).

Example 34: 2-(2-chlorophenyl)-5-(7-cyclopropyl-1,2,3,4-tetrahydronaphthalen-2-yl)-4,5,6,7-tetrahydro-3H-imidazo[4,5-c]pyridine

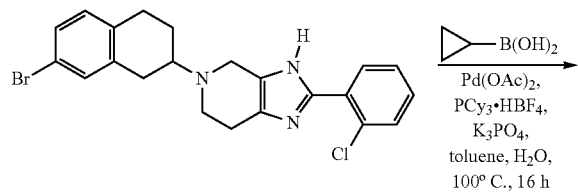

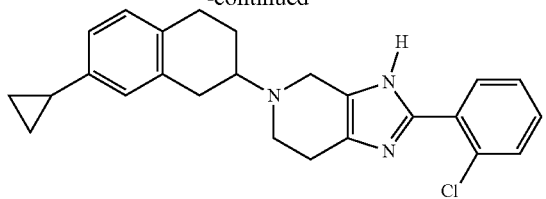

A solution of 5-(7-bromo-1,2,3,4-tetrahydronaphthalen-2-yl)-2-(2-chlorophenyl)-4,5,6,7-tetrahydro-3H-imidazo[4,5-c]pyridine (111 mg, 0.25 mmol), cyclopropylboronic acid (41 mg, 0.5 mmol), Pd(AcO)$_2$ (3 mg, 0.0125 mmol), PCy$_3$·HBF$_4$ (9 mg, 0.025 mmol) and K$_3$PO$_4$ (106 mg, 0.5 mmol) in toluene/H$_2$O=5/0.5 mL was stirred at 100° C. for 16 hours under N$_2$ atmosphere. After the reaction was finished, it was quenched with H$_2$O and extracted with dichloromethane (20 mL×3), the combined organic phases were washed with brine then concentrated to give a crude product, which was purified by prep-HPLC (Gemini-C$^{18}$ 150×21.2 mm, 5 µm, mobile phase: acetonitrile-H$_2$O (0.1% formic acid), gradient: 20-35) to afford 2-(2-chlorophenyl)-5-(7-cyclopropyl-1,2,3,4-tetrahydronaphthalen-2-yl)-4,5,6,7-tetrahydro-3H-imidazo[4,5-c]pyridine (17 mg, 16% yield) as white solid. MS (ESI): mass calcd. for $C_{25}H_{26}ClN_3$ 403.18, m/z found 403.9 $[M+H]+$, $^1$H NMR (400 MHz, CD$_3$OD) δ ppm 8.40 (s, 1H), 7.71-7.40 (m, 1H), 7.55-7.57 (m, 1H), 7.44-7.47 (m, 2H), 6.69-7.03 (m, 3H), 4.24-4.33 (m, 2H), 3.50-3.61 (m, 3H), 2.92-3.24 (m, 6H), 2.37-2.40 (m, 1H), 1.83-1.96 (m, 2H), 0.91-0.97 (m, 2H), 0.62-0.67 (m, 2H).

Example 35: 2-(2-chlorophenyl)-5-(7-(cyclopropylethynyl)-1,2,3,4-tetrahydronaphthalen-2-yl)-4,5,6,7-tetrahydro-3H-imidazo[4,5-c]pyridine

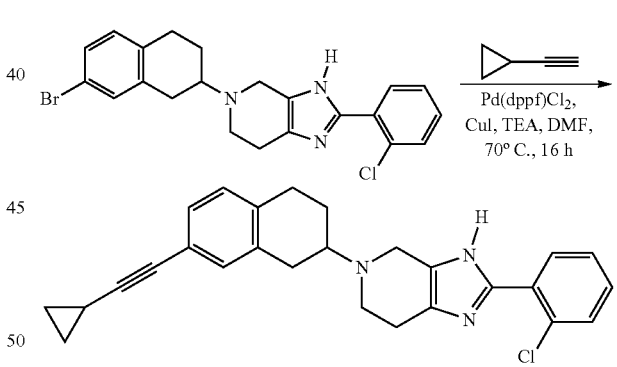

A solution of 5-(7-bromo-1,2,3,4-tetrahydronaphthalen-2-yl)-2-(2-chlorophenyl)-4,5,6,7-tetrahydro-3H-imidazo[4,5-c]pyridine (111 mg, 0.25 mmol), ethynylcyclopropane (33 mg, 0.125 mmol), Pd(dppf)Cl$_2$ (9 mg, 0.0125 mmol), CuI (5 mg, 0.025 mmol) and triethylamine (76 mg, 0.75 mmol) in dimethylformamide (5 mL) was stirred at 70° C. for 16 hours under N$_2$ atmosphere. After the reaction was finished, it was quenched with H$_2$O and extracted with dichloromethane (20 mL×3), the combined organic phases were washed with brine then concentrated to give a crude product, which was purified by prep-HPLC (Gemini-C$^{18}$ 150×21.2 mm, 5 µm, mobile phase: acetonitrile-H$_2$O (0.1% FA), gradient: 25-55) to afford 2-(2-chlorophenyl)-5-(7-(cyclopropylethynyl)-1,2,3,4-tetrahydronaphthalen-2-yl)-4,5,6,7-tetrahydro-3H-imidazo[4,5-c]pyridine (20 mg, 19% yield) as white solid. MS (ESI): mass calcd. for $C_{27}H_{26}ClN_3$ 427.18, m/z found 427.9 [M+H]+, $^1$H NMR (400 MHz, $CD_3OD$) δ ppm 7.71-7.73 (m, 1H), 7.54-7.56 (m, 1H), 7.42-7.44 (m, 2H), 7.04-7.15 (m, 3H), 4.03-4.11 (m, 2H), 3.29-3.38 (m, 2H), 2.88-3.12 (m, 7H), 2.32-2.35 (m, 1H), 1.84-1.89 (m, 1H), 1.42-1.48 (m, 1H), 0.86-0.88 (m, 2H), 0.70-0.74 (m, 2H).

Example 36: 2-(2-chlorophenyl)-5-(8-cyclopropyl-1,2,3,4-tetrahydronaphthalen-2-yl)-4,5,6,7-tetrahydro-3H-imidazo[4,5-c]pyridine

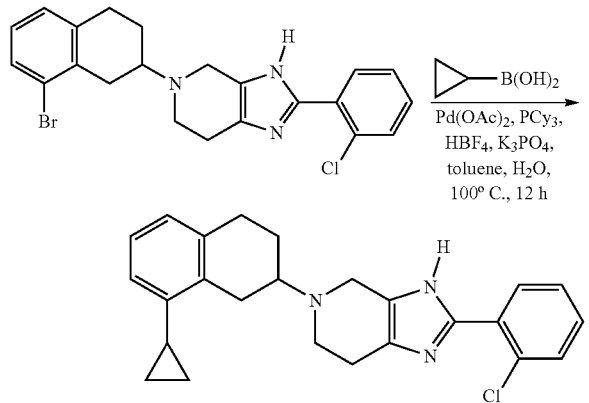

To a solution of 5-(8-bromo-1,2,3,4-tetrahydronaphthalen-2-yl)-2-(2-chlorophenyl)-4,5,6,7-tetrahydro-3H-imidazo[4,5-c]pyridine (150 mg, 0.34 mmol), cyclopropylboronic acid (59 mg, 0.68 mmol), Pd(OAc)2 (7.6 mg, 0.03 mmol), PCy$_3$·HBF$_4$ (25 mg, 0.068 mmol), $K_3PO_4$ (144 mg, 0.68 mmol) in toluene (20 mL) and $H_2O$ (2 mL) was added. The solution was stirred at 100° C. for 15 hrs. LCMS showed the reaction was finished, water (20 mL) was added. The solution was extracted with dichloromethane (30 mL×3). The combined organic phases were concentrated and the residue was purified by Prep-HPLC (Gemini-C18 150×21.2 mm, 5 μm, mobile phase: acetonitrile-$H_2O$ (0.1% formic acid), gradient: 20-70) to give 2-(2-chlorophenyl)-5-(8-cyclopropyl-1,2,3,4-tetrahydronaphthalen-2-yl)-4,5,6,7-tetrahydro-3H-imidazo[4,5-c]pyridine (2.3 mg, 1.6% yield) as a white solid. MS (ESI): mass calcd. for $C_{25}H_{26}ClN_3$ 403.95, m/z found 403.9 [M+H]$^+$, $^1$H NMR (400 MHz, DMSO-$d_6$) δ ppm 10.26 (s, 1H), 7.85-7.73 (m, 1H), 7.69-7.58 (m, 1H), 7.48 (dd, J=5.7, 3.6 Hz, 1H), 7.10 (t, J=7.6 Hz, 1H), 6.99 (d, J=7.4 Hz, 1H), 6.88 (d, J=7.5 Hz, 1H), 4.93-4.43 (m, 4H), 3.92 (s, 2H), 3.47 (s, 2H), 3.06 (s, 2H), 2.99-2.87 (m, 1H), 2.36 (d, J=17.1 Hz, 1H), 1.92 (s, 2H), 0.94 (ddd, J=14.3, 8.8, 4.9 Hz, 2H), 0.72 (s, 1H), 0.53 (s, 1H).

Example 37: 5-(7-chloro-1,2,3,4-tetrahydronaphthalen-2-yl)-2-(2-chloro-4-cyclopropylphenyl)-4,5,6,7-tetrahydro-3H-imidazo[4,5-c]pyridine

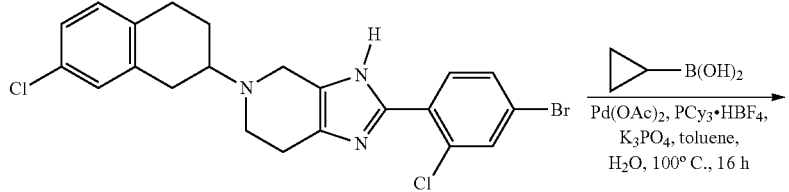

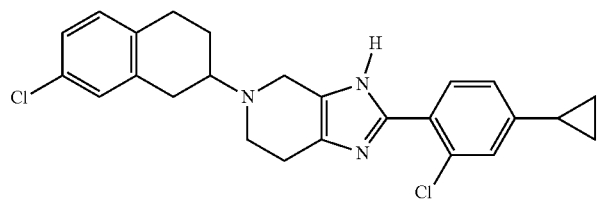

A solution of 2-(4-bromo-2-chlorophenyl)-5-(7-chloro-1,2,3,4-tetrahydronaphthalen-2-yl)-4,5,6,7-tetrahydro-3H-imidazo[4,5-c]pyridine (119 mg, 0.25 mmol), cyclopropylboronic acid (41 mg, 0.5 mmol), Pd(AcO)$_2$ (6 mg, 0.025 mmol), PCy$_3$·HBF$_4$ (19 mg, 0.05 mmol) and K$_3$PO$_4$ (106 mg, 0.5 mmol) in toluene/H$_2$O=5/0.5 mL was stirred at 100° C. for 16 hours under N$_2$ atmosphere. After the reaction was finished, it was quenched with H$_2$O and extracted with dichloromethane (20 mL×3), the combined organic phases were washed with brine then concentrated to give a crude product, which was purified by prep-HPLC (Gemini-C$^{18}$ 150×21.2 mm, 5 μm, mobile phase: acetonitrile-H$_2$O (0.1% formic acid), gradient: 20-60) to afford 5-(7-chloro-1,2,3,4-tetrahydronaphthalen-2-yl)-2-(2-chloro-4-cyclopropylphenyl)-4,5,6,7-tetrahydro-3H-imidazo[4,5-c]pyridine (17 mg, 16% yield) as white solid. MS (ESI): mass calcd. for C$_{25}$H$_{25}$Cl$_2$N$_3$ 437.14, m/z found 437.9 [M+H]$^+$, $^1$H NMR (400 MHz, CD$_3$OD) δ ppm 7.57-7.59 (m, 1H), 7.08-7.23 (m, 5H), 3.85-3.92 (m, 2H), 2.85-3.23 (m, 9H), 2.27-2.30 (in, 1H), 1.94-1.98 (m, 1H), 1.78-1.85 (m, 1H), 1.04-1.09 (m, 2H), 0.75-0.79 (in, 2H).

Examples 38-184

The following compounds are prepared substantially according to the procedures described above:

| Ex. No. | Chemical structure | Chemical name |
|---|---|---|
| 38 | 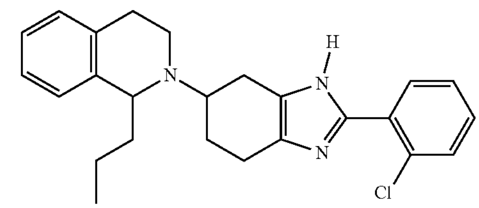 [SMILES: CCCC1c2ccccc2CCN1C1CCc2nc(-c3ccccc3Cl)[nH]c2C1] | 2-(2-(2-chlorophenyl)-4,5,6,7-tetrahydro-1H-benzo[d]imidazol-6-yl)-1-propyl-1,2,3,4-tetrahydroisoquinoline |
| 39 | 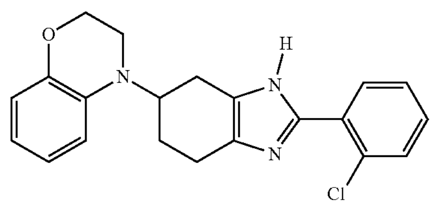 [SMILES: Clc1ccccc1-c1nc2c([nH]1)CC(N1CCOc3ccccc31)CC2] | 2-(2-chlorophenyl)-5-(chroman-4-yl)-4,5,6,7-tetrahydro-3H-imidazo[4,5-c]pyridine |
| 40 | 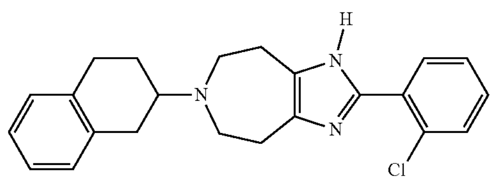 [SMILES: Clc1ccccc1-c1nc2c([nH]1)CCN(C1CCc3ccccc3C1)CC2] | 2-(2-chlorophenyl)-6-(1,2,3,4-tetrahydronaphthalen-2-yl)-1,4,5,6,7,8-hexahydroimidazo[4,5-d]azepine |
| 41 | 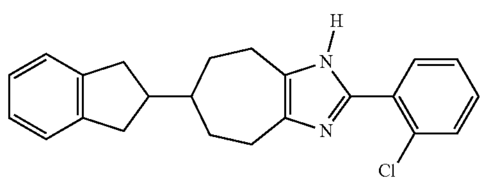 [SMILES: Clc1ccccc1-c1nc2c([nH]1)CCC(C1Cc3ccccc3C1)CC2] | 2-(2-chlorophenyl)-6-(2,3-dihydro-1H-inden-2-yl)-1,4,5,6,7,8-hexahydroimidazo[4,5-d]azepine |
| 42 | 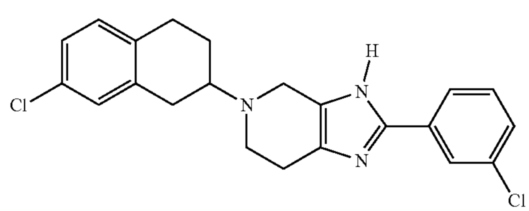 [SMILES: Clc1cccc(-c2nc3c([nH]2)CN(C2CCc4ccc(Cl)cc4C2)CC3)c1] | 5-(7-chloro-1,2,3,4-tetrahydronaphthalen-2-yl)-2-(3-chlorophenyl)-4,5,6,7-tetrahydro-3H-imidazo[4,5-c]pyridine |
| 43 | 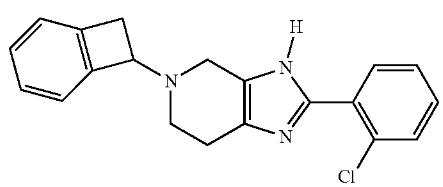 [SMILES: Clc1ccccc1-c1nc2c([nH]1)CN(C1Cc3ccccc31)CC2] | 5-(bicyclo[4.2.0]octa-1(6),2,4-trien-7-yl)-2-(2-chlorophenyl)-4,5,6,7-tetrahydro-3H-imidazo[4,5-c]pyridine |

-continued

| Ex. No. | Chemical structure | Chemical name |
|---|---|---|
| 44 | 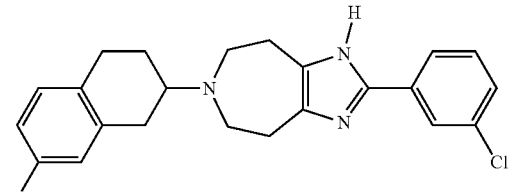 | 6-(7-chloro-1,2,3,4-tetrahydronaphthalen-2-yl)-2-(3-chlorophenyl)-1,4,5,6,7,8-hexahydroimidazo[4,5-d]azepine |
| 45 | 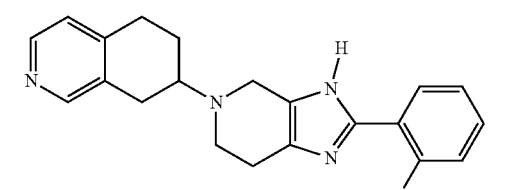 | 7-(2-(2-fluorophenyl)-3,4,6,7-tetrahydro-5H-imidazo[4,5-c]pyridin-5-yl)-5,6,7,8-tetrahydroisoquinoline |
| 46 | 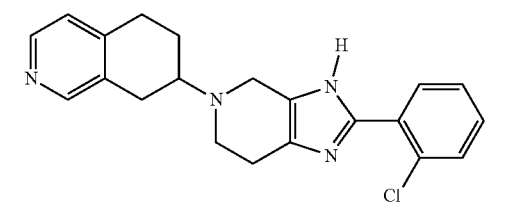 [SMILES: Clc1ccccc1-c1nc2c([nH]1)CN(C1CCc3ccncc3C1)CC2] | 7-(2-(2-chlorophenyl)-3,4,6,7-tetrahydro-5H-imidazo[4,5-c]pyridin-5-yl)-5,6,7,8-tetrahydroisoquinoline |
| 47 | 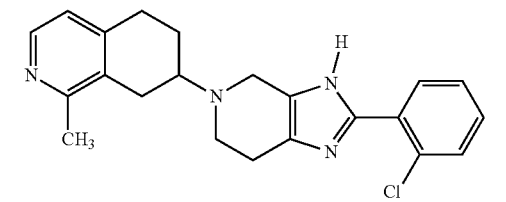 [SMILES: Cc1nccc2c1CC(N1CCc3nc(-c4ccccc4Cl)[nH]c3C1)CC2] | 7-(2-(2-chlorophenyl)-3,4,6,7-tetrahydro-5H-imidazo[4,5-c]pyridin-5-yl)-1-methyl-5,6,7,8-tetrahydroisoquinoline |
| 48 | 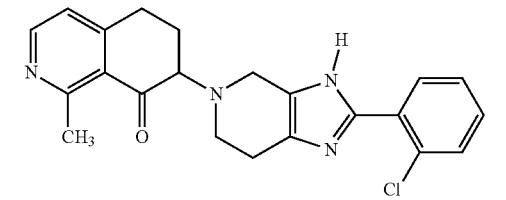 [SMILES: Cc1nccc2c1C(=O)C(N1CCc3nc(-c4ccccc4Cl)[nH]c3C1)CC2] | 7-(2-(2-chlorophenyl)-3,4,6,7-tetrahydro-5H-imidazo[4,5-c]pyridin-5-yl)-1-methyl-6,7-dihydroisoquinolin-8(5H)-one |
| 49 | 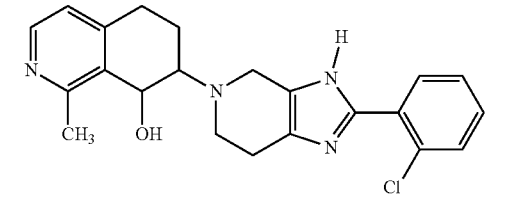 [SMILES: Cc1nccc2c1C(O)C(N1CCc3nc(-c4ccccc4Cl)[nH]c3C1)CC2] | 7-(2-(2-chlorophenyl)-3,4,6,7-tetrahydro-5H-imidazo[4,5-c]pyridin-5-yl)-1-methyl-5,6,7,8-tetrahydroisoquinolin-8-ol |
| 50 | 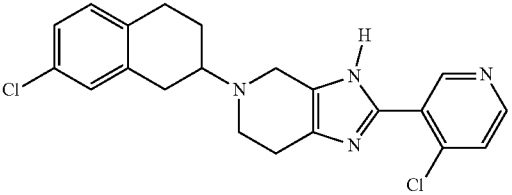 [SMILES: Clc1ccc2c(c1)CC(N1CCc3nc(-c4cnccc4Cl)[nH]c3C1)CC2] | 5-(7-chloro-1,2,3,4-tetrahydronaphthalen-2-yl)-2-(4-chloropyridin-3-yl)-4,5,6,7-tetrahydro-3H-imidazo[4,5-c]pyridine |

| Ex. No. | Chemical structure | Chemical name |
|---|---|---|
| 51 | 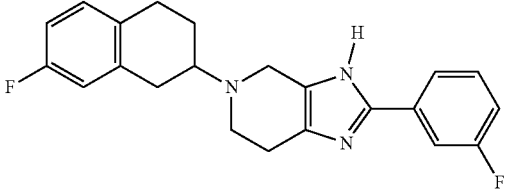 [SMILES: Fc1cccc(-c2nc3c([nH]2)CN(C2CCc4ccc(F)cc4C2)CC3)c1] | 5-(7-fluoro-1,2,3,4-tetrahydronaphthalen-2-yl)-2-(3-fluorophenyl)-4,5,6,7-tetrahydro-3H-imidazo[4,5-c]pyridine |
| 52 | 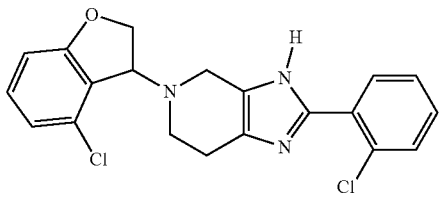 [SMILES: Clc1ccccc1-c1nc2c([nH]1)CN(C1COc3cccc(Cl)c31)CC2] | 5-(4-chloro-2,3-dihydrobenzofuran-3-yl)-2-(2-chlorophenyl)-4,5,6,7-tetrahydro-3H-imidazo[4,5-c]pyridine |
| 53 | 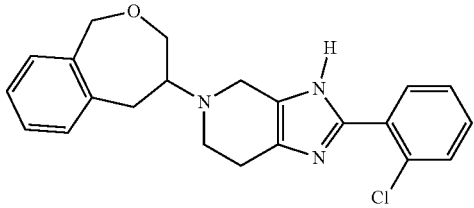 [SMILES: Clc1ccccc1-c1nc2c([nH]1)CN(C1COCc3ccccc3C1)CC2] | 2-(2-chlorophenyl)-5-(1,3,4,5-tetrahydrobenzo[c]oxepin-4-yl)-4,5,6,7-tetrahydro-3H-imidazo[4,5-c]pyridine |
| 54 | 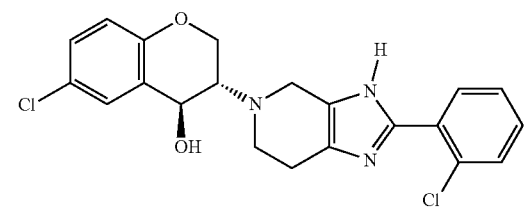 [SMILES: O[C@H]1c2cc(Cl)ccc2OC[C@@H]1N1CCc2nc(-c3ccccc3Cl)[nH]c2C1] | trans-6-chloro-3-(2-(2-chlorophenyl)-3,4,6,7-tetrahydro-5H-imidazo[4,5-c]pyridin-5-yl)chroman-4-ol |
| 55 | 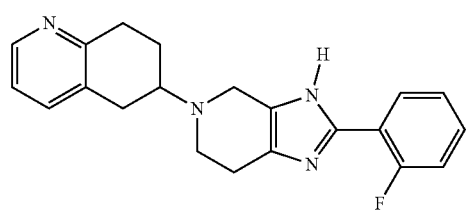 [SMILES: Fc1ccccc1-c1nc2c([nH]1)CN(C1CCc3ncccc3C1)CC2] | 6-(2-(2-fluorophenyl)-3,4,6,7-tetrahydro-5H-imidazo[4,5-c]pyridin-5-yl)-5,6,7,8-tetrahydroquinoline |
| 56 | 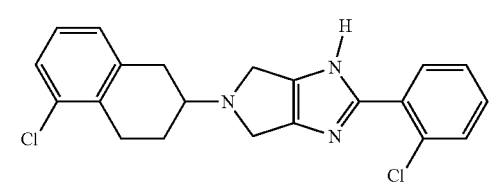 [SMILES: Clc1ccccc1-c1nc2c([nH]1)CN(C1CCc3c(Cl)cccc3C1)C2] | 5-(5-chloro-1,2,3,4-tetrahydronaphthalen-2-yl)-2-(2-chlorophenyl)-1,4,5,6-tetrahydropyrrolo[3,4-d]imidazole |
| 57 | 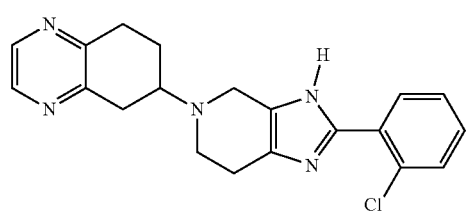 [SMILES: Clc1ccccc1-c1nc2c([nH]1)CN(C1CCc3nccnc3C1)CC2] | 6-(2-(2-chlorophenyl)-3,4,6,7-tetrahydro-5H-imidazo[4,5-c]pyridin-5-yl)-5,6,7,8-tetrahydroquinoxaline |

-continued

| Ex. No. | Chemical structure | Chemical name |
|---|---|---|
| 58 | 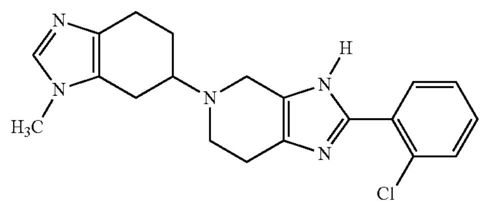 [SMILES: Cn1cnc2c1CC(N1CCc3nc(-c4ccccc4Cl)[nH]c3C1)CC2] | 2-(2-chlorophenyl)-5-(1-methyl-4,5,6,7-tetrahydro-1H-benzo[d]imidazol-6-yl)-4,5,6,7-tetrahydro-3H-imidazo[4,5-c]pyridine |
| 59 | 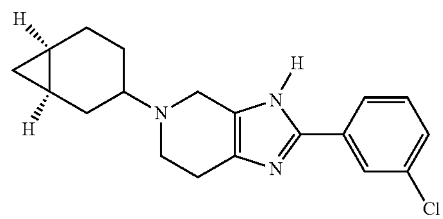 [SMILES: Clc1cccc(-c2nc3c([nH]2)CN(C2CC[C@@H]4C[C@@H]4C2)CC3)c1] | 5-(cis-bicyclo[4.1.0]heptan-3-yl)-2-(3-chlorophenyl)-4,5,6,7-tetrahydro-3H-imidazo[4,5-c]pyridine |
| 60 | 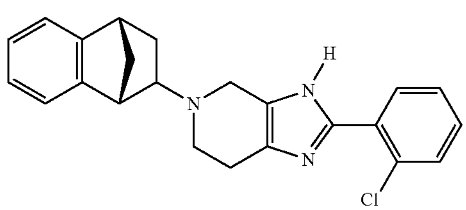 [SMILES: Clc1ccccc1-c1nc2c([nH]1)CN(C1C[C@@H]3C[C@H]1c1ccccc13)CC2] | 2-(2-chlorophenyl)-5-((1S,4S)-1,2,3,4-tetrahydro-1,4-methanonaphthalen-2-yl)-4,5,6,7-tetrahydro-3H-imidazo[4,5-c]pyridine |
| 61 | 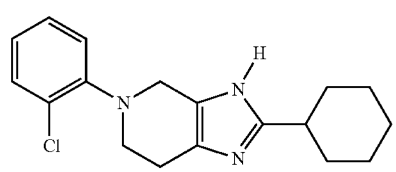 [SMILES: Clc1ccccc1N1CCc2nc(C3CCCCC3)[nH]c2C1] | 5-(8-chloro-1,2,3,4-tetrahydronaphthalen-2-yl)-2-cyclohexyl-4,5,6,7-tetrahydro-3H-imidazo[4,5-c]pyridine |
| 62 | 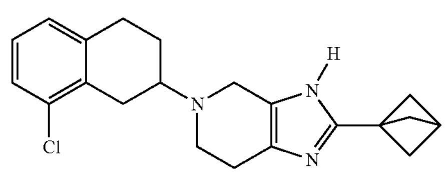 [SMILES: Clc1cccc2c1CC(N1CCc3nc(C45CC(C4)C5)[nH]c3C1)CC2] | 2-(bicyclo[1.1.1]pentan-1-yl)-5-(8-chloro-1,2,3,4-tetrahydronaphthalen-2-yl)-4,5,6,7-tetrahydro-3H-imidazo[4,5-c]pyridine |
| 63 | 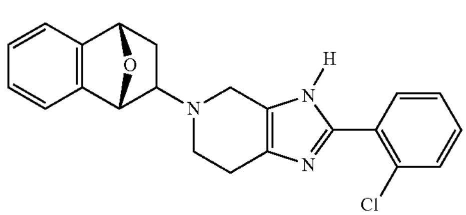 [SMILES: Clc1ccccc1-c1nc2c([nH]1)CN(C1C[C@@H]3O[C@H]1c1ccccc13)CC2] | 2-(2-chlorophenyl)-5-((1S,4S)-1,2,3,4-tetrahydro-1,4-epoxynaphthalen-2-yl)-4,5,6,7-tetrahydro-3H-imidazo[4,5-c]pyridine |
| 64 | 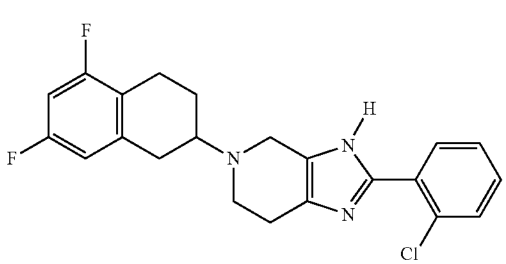 [SMILES: Fc1cc(F)c2c(c1)CC(N1CCc3nc(-c4ccccc4Cl)[nH]c3C1)CC2] | 2-(2-chlorophenyl)-5-(5,7-difluoro-1,2,3,4-tetrahydronaphthalen-2-yl)-4,5,6,7-tetrahydro-3H-imidazo[4,5-c]pyridine |

-continued

| Ex. No. | Chemical structure | Chemical name |
|---|---|---|
| 65 | 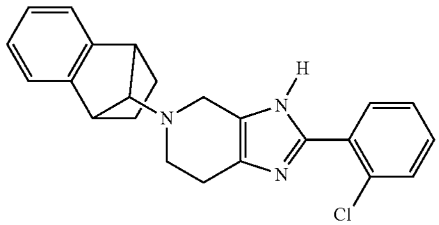 [SMILES: Clc1ccccc1-c1nc2c([nH]1)CN(C1C3CCC1c1ccccc13)CC2] | 2-(2-chlorophenyl)-5-(1,2,3,4-tetrahydro-1,4-methanonaphthalen-9-yl)-4,5,6,7-tetrahydro-3H-imidazo[4,5-c]pyridine |
| 66 | 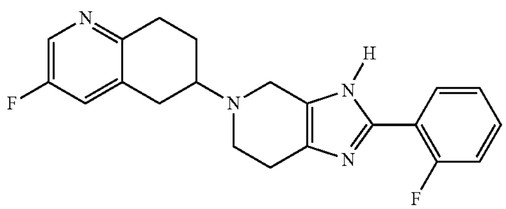 [SMILES: Fc1cnc2c(c1)CC(N1CCc3nc(-c4ccccc4F)[nH]c3C1)CC2] | 3-fluoro-6-(2-(2-fluorophenyl)-3,4,6,7-tetrahydro-5H-imidazo[4,5-c]pyridin-5-yl)-5,6,7,8-tetrahydroquinoline |
| 67 | 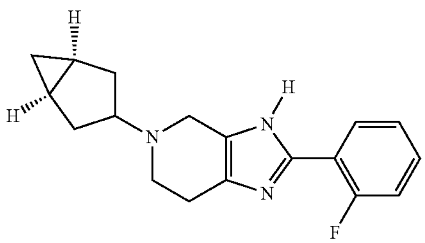 [SMILES: Fc1ccccc1-c1nc2c([nH]1)CN(C1C[C@@H]3C[C@@H]3C1)CC2] | 5-(cis-bicyclo[3.1.0]hexan-3-yl)-2-(2-fluorophenyl)-4,5,6,7-tetrahydro-3H-imidazo[4,5-c]pyridine |
| 68 | 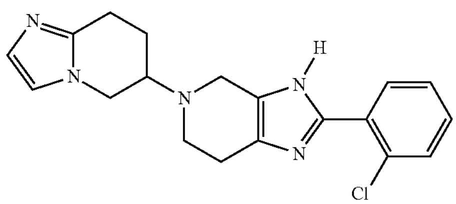 [SMILES: Clc1ccccc1-c1nc2c([nH]1)CN(C1CCc3nccn3C1)CC2] | 2-(2-chlorophenyl)-5-(5,6,7,8-tetrahydroimidazo[1,2-a]pyridin-6-yl)-4,5,6,7-tetrahydro-3H-imidazo[4,5-c]pyridine |
| 69 | 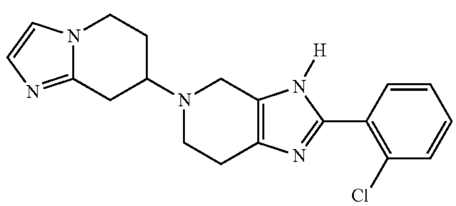 [SMILES: Clc1ccccc1-c1nc2c([nH]1)CN(C1CCn3ccnc3C1)CC2] | 2-(2-chlorophenyl)-5-(5,6,7,8-tetrahydroimidazo[1,2-a]pyridin-7-yl)-4,5,6,7-tetrahydro-3H-imidazo[4,5-c]pyridine |
| 70 | 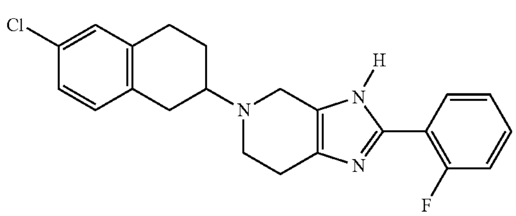 [SMILES: Fc1ccccc1-c1nc2c([nH]1)CN(C1CCc3cc(Cl)ccc3C1)CC2] | 5-(6-chloro-1,2,3,4-tetrahydronaphthalen-2-yl)-2-(2-fluorophenyl)-4,5,6,7-tetrahydro-3H-imidazo[4,5-c]pyridine |
| 71 | 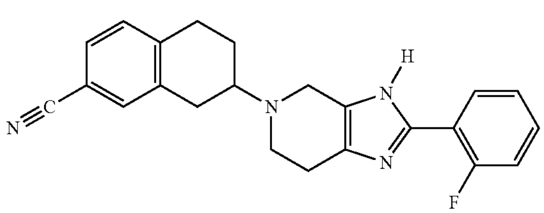 [SMILES: N#Cc1ccc2c(c1)CC(N1CCc3nc(-c4ccccc4F)[nH]c3C1)CC2] | 7-(2-(2-fluorophenyl)-3,4,6,7-tetrahydro-5H-imidazo[4,5-c]pyridin-5-yl)-5,6,7,8-tetrahydronaphthalene-2-carbonitrile |

-continued

| Ex. No. | Chemical structure | Chemical name |
|---|---|---|
| 72 | 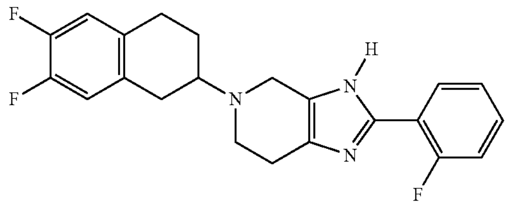 [SMILES: Fc1cc2c(cc1F)CC(N1CCc3nc(-c4ccccc4F)[nH]c3C1)CC2] | 5-(6,7-difluoro-1,2,3,4-tetrahydronaphthalen-2-yl)-2-(2-fluorophenyl)-4,5,6,7-tetrahydro-3H-imidazo[4,5-c]pyridine |
| 73 | 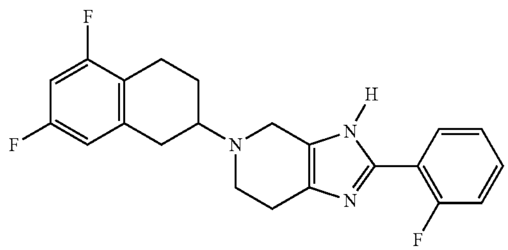 [SMILES: Fc1cc(F)c2c(c1)CC(N1CCc3nc(-c4ccccc4F)[nH]c3C1)CC2] | 5-(5,7-difluoro-1,2,3,4-tetrahydronaphthalen-2-yl)-2-(2-fluorophenyl)-4,5,6,7-tetrahydro-3H-imidazo[4,5-c]pyridine |
| 74 | 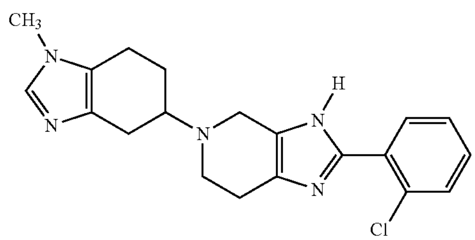 [SMILES: Cn1cnc2c1CCC(N1CCc3nc(-c4ccccc4Cl)[nH]c3C1)C2] | 2-(2-chlorophenyl)-5-(1-methyl-4,5,6,7-tetrahydro-1H-benzo[d]imidazol-5-yl)-4,5,6,7-tetrahydro-3H-imidazo[4,5-c]pyridine |
| 75 | 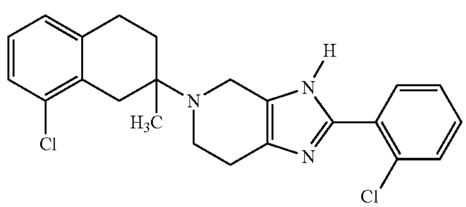 [SMILES: CC1(N2CCc3nc(-c4ccccc4Cl)[nH]c3C2)CCc2cccc(Cl)c2C1] | 5-(8-chloro-2-methyl-1,2,3,4-tetrahydronaphthalen-2-yl)-2-(2-chlorophenyl)-4,5,6,7-tetrahydro-3H-imidazo[4,5-c]pyridine |
| 76 | 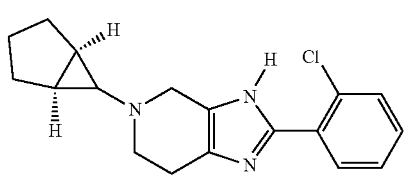 [SMILES: Clc1ccccc1-c1nc2c([nH]1)CN(C1[C@H]3CCC[C@@H]13)CC2] | 5-((1R,5S)-bicyclo[3.1.0]hexan-6-yl)-2-(2-chlorophenyl)-4,5,6,7-tetrahydro-3H-imidazo[4,5-c]pyridine |
| 77 | 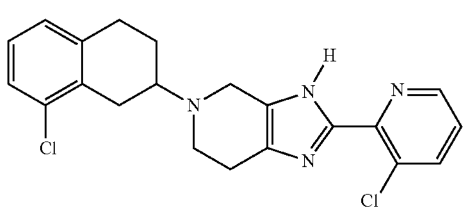 [SMILES: Clc1cccnc1-c1nc2c([nH]1)CN(C1CCc3cccc(Cl)c3C1)CC2] | 5-(8-chloro-1,2,3,4-tetrahydronaphthalen-2-yl)-2-(3-chloropyridin-2-yl)-4,5,6,7-tetrahydro-3H-imidazo[4,5-c]pyridine |
| 78 | 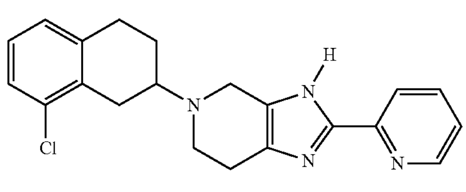 [SMILES: Clc1cccc2c1CC(N1CCc3nc(-c4ccccn4)[nH]c3C1)CC2] | 5-(8-chloro-1,2,3,4-tetrahydronaphthalen-2-yl)-2-(pyridin-2-yl)-4,5,6,7-tetrahydro-3H-imidazo[4,5-c]pyridine |

| Ex. No. | Chemical structure | Chemical name |
|---|---|---|
| 79 | 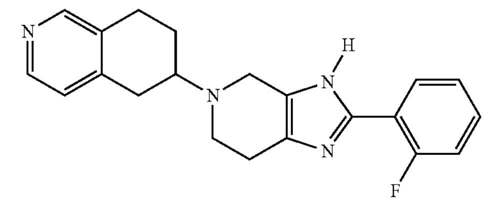 | 6-(2-(2-fluorophenyl)-3,4,6,7-tetrahydro-5H-imidazo[4,5-c]pyridin-5-yl)-5,6,7,8-tetrahydroisoquinoline |
| 80 | 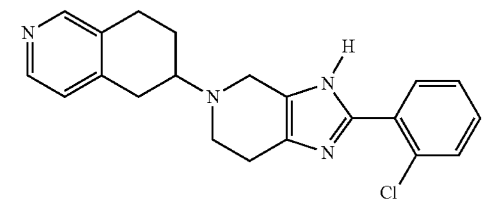 [SMILES: Clc1ccccc1-c1nc2c([nH]1)CN(C1CCc3cnccc3C1)CC2] | 6-(2-(2-chlorophenyl)-3,4,6,7-tetrahydro-5H-imidazo[4,5-c]pyridin-5-yl)-5,6,7,8-tetrahydroisoquinoline |
| 81 | 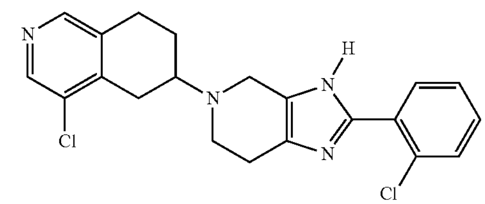 [SMILES: Clc1ccccc1-c1nc2c([nH]1)CN(C1CCc3cncc(Cl)c3C1)CC2] | 4-chloro-6-(2-(2-chlorophenyl)-3,4,6,7-tetrahydro-5H-imidazo[4,5-c]pyridin-5-yl)-5,6,7,8-tetrahydroisoquinoline |
| 82 | 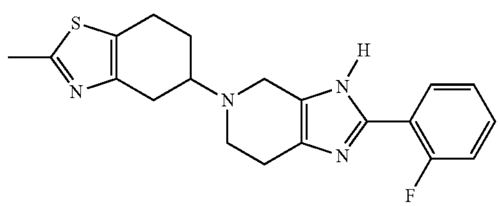 [SMILES: Cc1nc2c(s1)CCC(N1CCc3nc(-c4ccccc4F)[nH]c3C1)C2] | 5-(2-(2-fluorophenyl)-3,4,6,7-tetrahydro-5H-imidazo[4,5-c]pyridin-5-yl)-2-methyl-4,5,6,7-tetrahydrobenzo[d]thiazole |
| 83 | 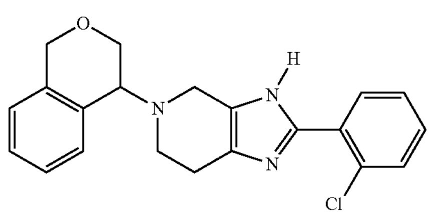 [SMILES: Clc1ccccc1-c1nc2c([nH]1)CN(C1COCc3ccccc31)CC2] | 2-(2-chlorophenyl)-5-(isochroman-4-yl)-4,5,6,7-tetrahydro-3H-imidazo[4,5-c]pyridine |
| 84 | 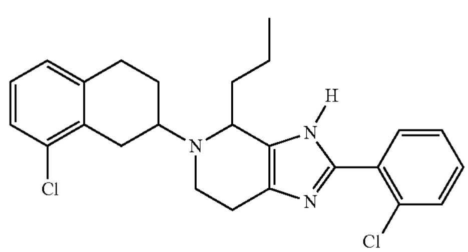 [SMILES: CCCC1c2[nH]c(-c3ccccc3Cl)nc2CCN1C1CCc2cccc(Cl)c2C1] | 5-(8-chloro-1,2,3,4-tetrahydronaphthalen-2-yl)-2-(2-chlorophenyl)-4-propyl-4,5,6,7-tetrahydro-3H-imidazo[4,5-c]pyridine |
| 85 | 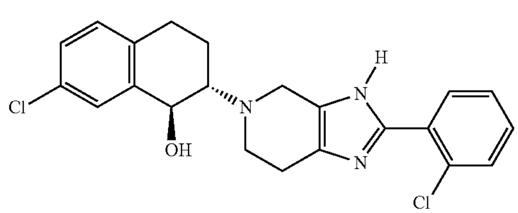 [SMILES: O[C@H]1c2cc(Cl)ccc2CC[C@@H]1N1CCc2nc(-c3ccccc3Cl)[nH]c2C1] | trans-7-chloro-2-(2-(2-chlorophenyl)-3,4,6,7-tetrahydro-5H-imidazo[4,5-c]pyridin-5-yl)-1,2,3,4-tetrahydronaphthalen-1-ol |

| Ex. No. | Chemical structure | Chemical name |
|---|---|---|
| 86 | 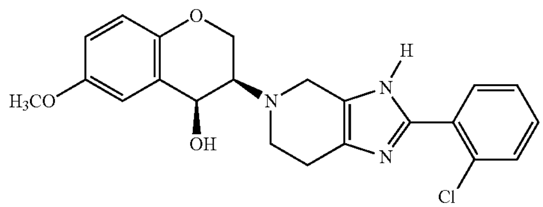 [SMILES: COc1ccc2c(c1)[C@H](O)[C@H](N1CCc3nc(-c4ccccc4Cl)[nH]c3C1)CO2] | cis-3-(2-(2-chlorophenyl)-3,4,6,7-tetrahydro-5H-imidazo[4,5-c]pyridin-5-yl)-6-methoxychroman-4-ol |
| 87 | 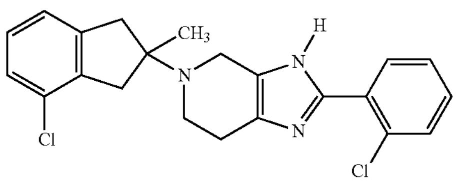 [SMILES: CC1(N2CCc3nc(-c4ccccc4Cl)[nH]c3C2)Cc2cccc(Cl)c2C1] | 5-(4-chloro-2-methyl-2,3-dihydro-1H-inden-2-yl)-2-(2-chlorophenyl)-4,5,6,7-tetrahydro-3H-imidazo[4,5-c]pyridine |
| 88 | 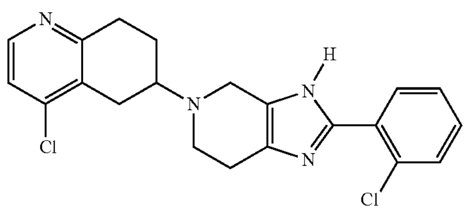 [SMILES: Clc1ccccc1-c1nc2c([nH]1)CN(C1CCc3nccc(Cl)c3C1)CC2] | 4-chloro-6-(2-(2-chlorophenyl)-3,4,6,7-tetrahydro-5H-imidazo[4,5-c]pyridin-5-yl)-5,6,7,8-tetrahydroquinoline |
| 89 | 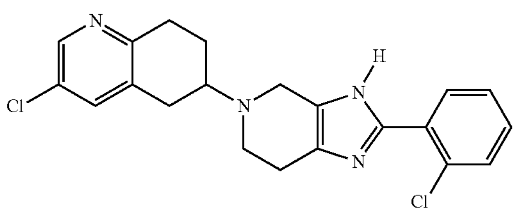 [SMILES: Clc1cnc2c(c1)CC(N1CCc3nc(-c4ccccc4Cl)[nH]c3C1)CC2] | 3-chloro-6-(2-(2-chlorophenyl)-3,4,6,7-tetrahydro-5H-imidazo[4,5-c]pyridin-5-yl)-5,6,7,8-tetrahydroquinoline |
| 90 | 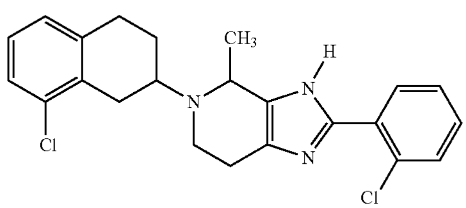 [SMILES: CC1c2[nH]c(-c3ccccc3Cl)nc2CCN1C1CCc2cccc(Cl)c2C1] | 5-(8-chloro-1,2,3,4-tetrahydronaphthalen-2-yl)-2-(2-chlorophenyl)-4-methyl-4,5,6,7-tetrahydro-3H-imidazo[4,5-c]pyridine |
| 91 | 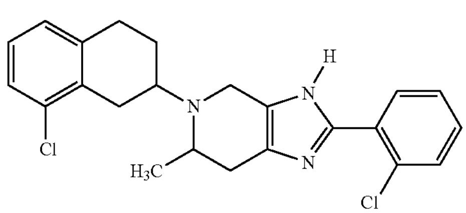 [SMILES: CC1Cc2nc(-c3ccccc3Cl)[nH]c2CN1C1CCc2cccc(Cl)c2C1] | 5-(8-chloro-1,2,3,4-tetrahydronaphthalen-2-yl)-2-(2-chlorophenyl)-6-methyl-4,5,6,7-tetrahydro-3H-imidazo[4,5-c]pyridine |
| 92 | 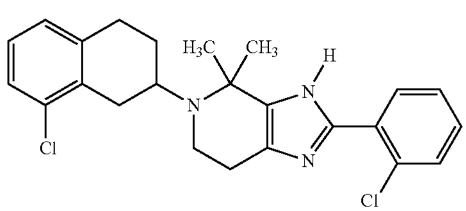 [SMILES: CC1(C)c2[nH]c(-c3ccccc3Cl)nc2CCN1C1CCc2cccc(Cl)c2C1] | 5-(8-chloro-1,2,3,4-tetrahydronaphthalen-2-yl)-2-(2-chlorophenyl)-4,4-dimethyl-4,5,6,7-tetrahydro-3H-imidazo[4,5-c]pyridine |

| Ex. No. | Chemical structure | Chemical name |
|---|---|---|
| 93 | 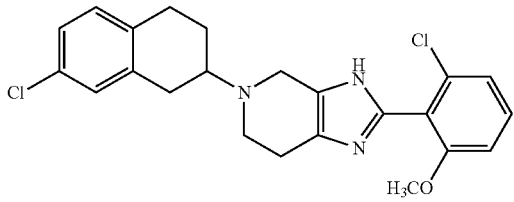 [SMILES: COc1cccc(Cl)c1-c1nc2c([nH]1)CN(C1CCc3ccc(Cl)cc3C1)CC2] | 5-(7-chloro-1,2,3,4-tetrahydronaphthalen-2-yl)-2-(2-chloro-6-methoxyphenyl)-4,5,6,7-tetrahydro-3H-imidazo[4,5-c]pyridine |
| 94 | 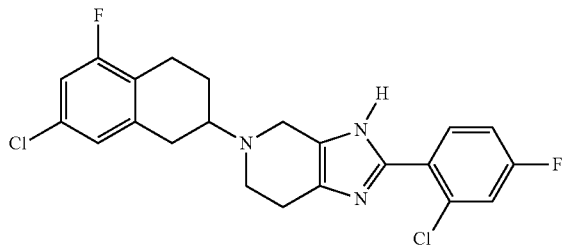 [SMILES: Fc1ccc(-c2nc3c([nH]2)CN(C2CCc4c(F)cc(Cl)cc4C2)CC3)c(Cl)c1] | 2-(2-chloro-4-fluorophenyl)-5-(7-chloro-5-fluoro-1,2,3,4-tetrahydronaphthalen-2-yl)-4,5,6,7-tetrahydro-3H-imidazo[4,5-c]pyridine |
| 95 | 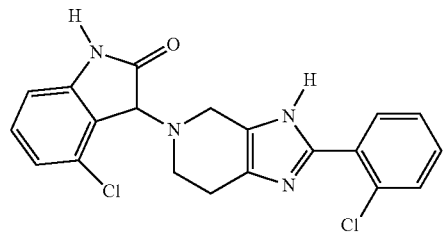 [SMILES: O=C1Nc2cccc(Cl)c2C1N1CCc2nc(-c3ccccc3Cl)[nH]c2C1] | 4-chloro-3-(2-(2-chlorophenyl)-3,4,6,7-tetrahydro-5H-imidazo[4,5-c]pyridin-5-yl)indolin-2-one |
| 96 | 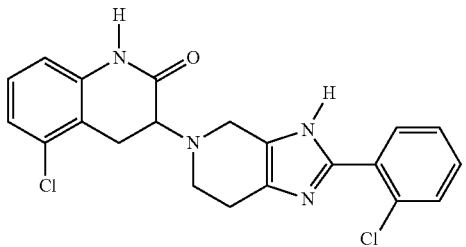 [SMILES: O=C1Nc2cccc(Cl)c2CC1N1CCc2nc(-c3ccccc3Cl)[nH]c2C1] | 5-chloro-3-(2-(2-chlorophenyl)-3,4,6,7-tetrahydro-5H-imidazo[4,5-c]pyridin-5-yl)-3,4-dihydroquinolin-2(1H)-one |
| 97 | 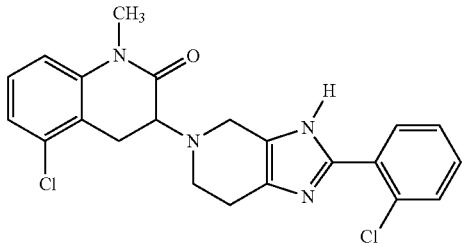 [SMILES: CN1C(=O)C(N2CCc3nc(-c4ccccc4Cl)[nH]c3C2)Cc2c(Cl)cccc21] | 5-chloro-3-(2-(2-chlorophenyl)-3,4,6,7-tetrahydro-5H-imidazo[4,5-c]pyridin-5-yl)-1-methyl-3,4-dihydroquinolin-2(1H)-one |
| 98 | 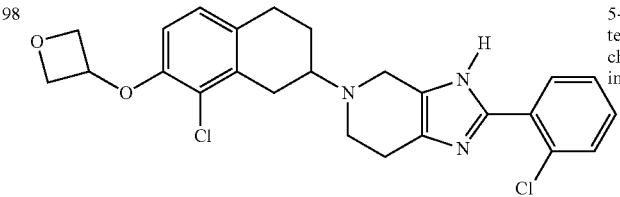 | 5-(8-chloro-7-(oxetan-3-yloxy)-1,2,3,4-tetrahydronaphthalen-2-yl)-2-(2-chlorophenyl)-4,5,6,7-tetrahydro-3H-imidazo[4,5-c]pyridine |

-continued

| Ex. No. | Chemical structure | Chemical name |
|---|---|---|
| 99 | 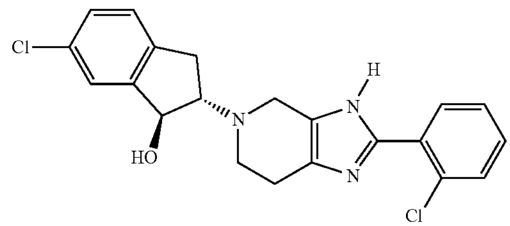 [SMILES: O[C@H]1c2cc(Cl)ccc2C[C@@H]1N1CCc2nc(-c3ccccc3Cl)[nH]c2C1] | trans-6-chloro-2-(2-(2-chlorophenyl)-3,4,6,7-tetrahydro-5H-imidazo[4,5-c]pyridin-5-yl)-2,3-dihydro-1H-inden-1-ol |
| 100 | 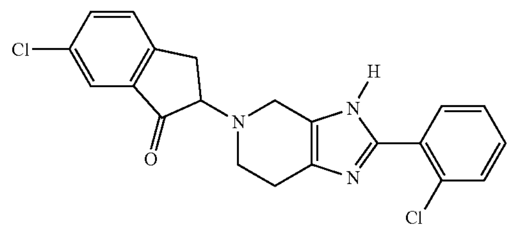 [SMILES: O=C1c2cc(Cl)ccc2CC1N1CCc2nc(-c3ccccc3Cl)[nH]c2C1] | 6-chloro-2-(2-(2-chlorophenyl)-3,4,6,7-tetrahydro-5H-imidazo[4,5-c]pyridin-5-yl)-2,3-dihydro-1H-inden-1-one |
| 101 | 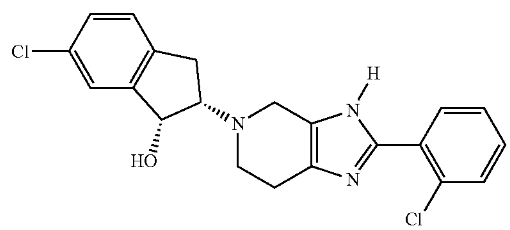 [SMILES: O[C@@H]1c2cc(Cl)ccc2C[C@@H]1N1CCc2nc(-c3ccccc3Cl)[nH]c2C1] | cis-6-chloro-2-(2-(2-chlorophenyl)-3,4,6,7-tetrahydro-5H-imidazo[4,5-c]pyridin-5-yl)-2,3-dihydro-1H-inden-1-ol |
| 102 | 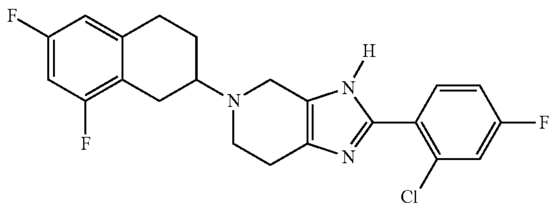 [SMILES: Fc1ccc(-c2nc3c([nH]2)CN(C2CCc4cc(F)cc(F)c4C2)CC3)c(Cl)c1] | 2-(2-chloro-4-fluorophenyl)-5-(6,8-difluoro-1,2,3,4-tetrahydronaphthalen-2-yl)-4,5,6,7-tetrahydro-3H-imidazo[4,5-c]pyridine |
| 103 | 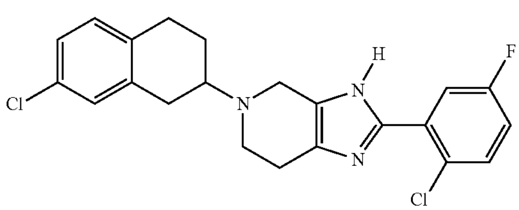 [SMILES: Fc1ccc(Cl)c(-c2nc3c([nH]2)CN(C2CCc4ccc(Cl)cc4C2)CC3)c1] | 5-(7-chloro-1,2,3,4-tetrahydronaphthalen-2-1-2-2-chloro-5-fluorophenyl)-4,5,6,7-tetrahydro-3H-imidazo[4,5-c]pyridine |
| 104 | 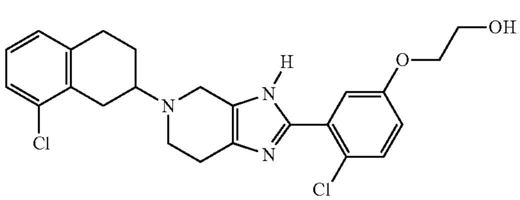 [SMILES: OCCOc1ccc(Cl)c(-c2nc3c([nH]2)CN(C2CCc4cccc(Cl)c4C2)CC3)c1] | 2-(4-chloro-3-(5-(8-chloro-1,2,3,4-tetrahydronaphthalen-2-yl)-4,5,6,7-tetrahydro-3H-imidazo[4,5-c]pyridin-2-yl)phenoxy)ethan-1-ol |
| 105 | 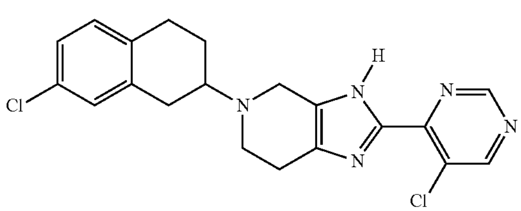 [SMILES: Clc1ccc2c(c1)CC(N1CCc3nc(-c4ncncc4Cl)[nH]c3C1)CC2] | 5-(7-chloro-1,2,3,4-tetrahydronaphthalen-2-yl)-2-(5-chloropyrimidin-4-yl)-4,5,6,7-tetrahydro-3H-imidazo[4,5-c]pyridine |

-continued

| Ex. No. | Chemical structure | Chemical name |
|---|---|---|
| 106 | 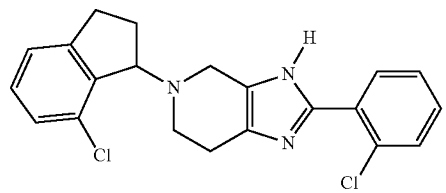 [SMILES: Clc1ccccc1-c1nc2c([nH]1)CN(C1CCc3cccc(Cl)c31)CC2] | 5-(7-chloro-2,3-dihydro-1H-inden-1-yl)-2-(2-chlorophenyl)-4,5,6,7-tetrahydro-3H-imidazo[4,5-c]pyridine |
| 107 | 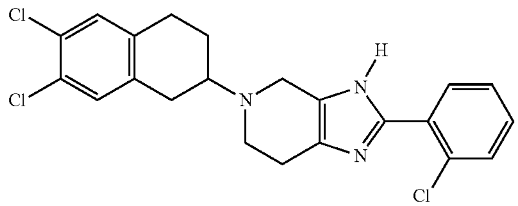 [SMILES: Clc1cc2c(cc1Cl)CC(N1CCc3nc(-c4ccccc4Cl)[nH]c3C1)CC2] | 2-(2-chlorophenyl)-5-(6,7-dichloro-1,2,3,4-tetrahydronaphthalen-2-yl)-4,5,6,7-tetrahydro-3H-imidazo[4,5-c]pyridine |
| 108 | 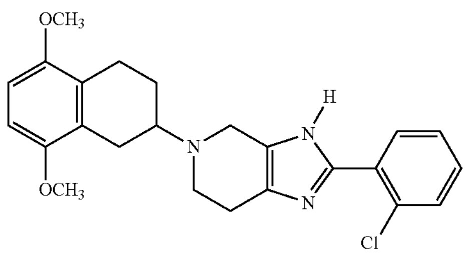 [SMILES: COc1ccc(OC)c2c1CCC(N1CCc3nc(-c4ccccc4Cl)[nH]c3C1)C2] | 2-(2-chlorophenyl)-5-(5,8-dimethoxy-1,2,3,4-tetrahydronaphthalen-2-yl)-4,5,6,7-tetrahydro-3H-imidazo[4,5-c]pyridine |
| 109 | 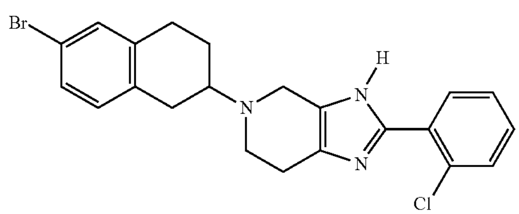 [SMILES: Clc1ccccc1-c1nc2c([nH]1)CN(C1CCc3cc(Br)ccc3C1)CC2] | 5-(6-bromo-1,2,3,4-tetrahydronaphthalen-2-yl)-2-(2-chlorophenyl)-4,5,6,7-tetrahydro-3H-imidazo[4,5-c]pyridine |
| 110 | 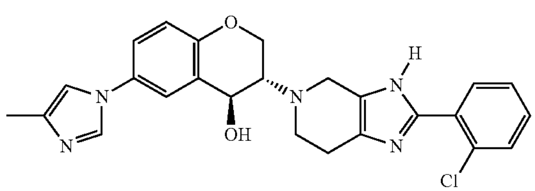 [SMILES: Cc1cn(-c2ccc3c(c2)[C@H](O)[C@@H](N2CCc4nc(-c5ccccc5Cl)[nH]c4C2)CO3)cn1] | (3S,4S)-3-(2-(2-chlorophenyl)-3,4,6,7-tetrahydro-5H-imidazo[4,5-c]pyridin-5-yl)-6-(4-methyl-1H-imidazol-1-yl)chroman-4-ol |
| 111 | 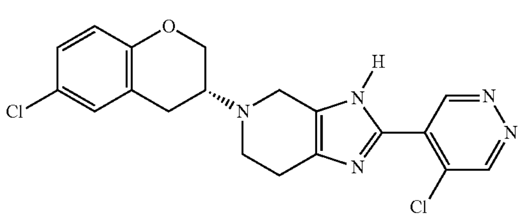 [SMILES: Clc1ccc2c(c1)C[C@@H](N1CCc3nc(-c4cnncc4Cl)[nH]c3C1)CO2] | (R)-5-(6-chlorochroman-3-yl)-2-(5-chloropyridazin-4-yl)-4,5,6,7-tetrahydro-3H-imidazo[4,5-c]pyridine |
| 112 | 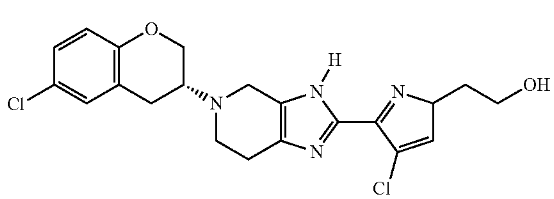 [SMILES: OCCC1C=C(Cl)C(c2nc3c([nH]2)CN([C@H]2COc4ccc(Cl)cc4C2)CC3)=N1] | (R)-2-(4-chloro-3-(5-(6-chlorochroman-3-yl)-4,5,6,7-tetrahydro-3H-imidazo[4,5-c]pyridin-2-yl)-1H-pyrazol-1-yl)ethan-1-ol |

-continued

| Ex. No. | Chemical structure | Chemical name |
|---|---|---|
| 113 | 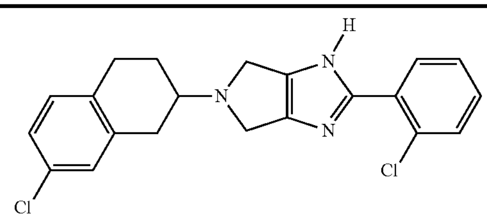 | 5-(7-chloro-1,2,3,4-tetrahydronaphthalen-2-yl)-2-(2-chlorophenyl)-1,4,5,6-tetrahydropyrrolo[3,4-d]imidazole |
| 114 | 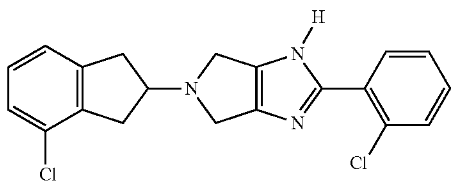 [SMILES: Clc1ccccc1-c1nc2c([nH]1)CN(C1Cc3cccc(Cl)c3C1)C2] | 5-(4-chloro-2,3-dihydro-1H-inden-2-yl)-2-(2-chlorophenyl)-1,4,5,6-tetrahydropyrrolo[3,4-d]imidazole |
| 115 | 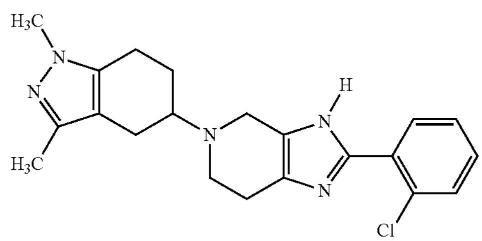 [SMILES: Cc1nn(C)c2c1CC(N1CCc3nc(-c4ccccc4Cl)[nH]c3C1)CC2] | 2-(2-chlorophenyl)-5-(1,3-dimethyl-4,5,6,7-tetrahydro-1H-indazol-5-yl)-4,5,6,7-tetrahydro-3H-imidazo[4,5-c]pyridine |
| 116 | 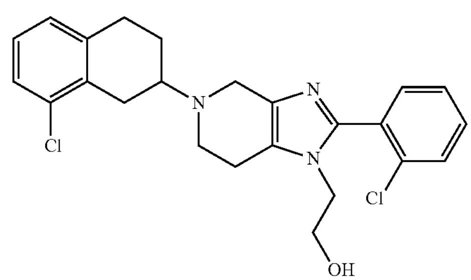 [SMILES: OCCn1c(-c2ccccc2Cl)nc2c1CCN(C1CCc3cccc(Cl)c3C1)C2] | 2-(5-(8-chloro-1,2,3,4-tetrahydronaphthalen-2-yl)-2-(2-chlorophenyl)-4,5,6,7-tetrahydro-1H-imidazo[4,5-c]pyridin-1-yl)ethan-1-ol |
| 117 | 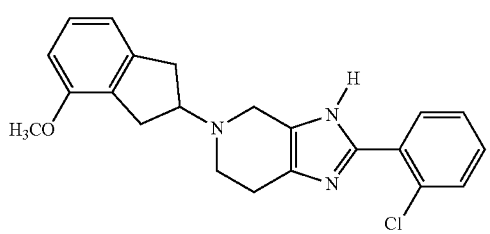 [SMILES: COc1cccc2c1CC(N1CCc3nc(-c4ccccc4Cl)[nH]c3C1)C2] | 2-(2-chlorophenyl)-5-(4-methoxy-2,3-dihydro-1H-inden-2-yl)-4,5,6,7-tetrahydro-3H-imidazo[4,5-c]pyridine |
| 118 | 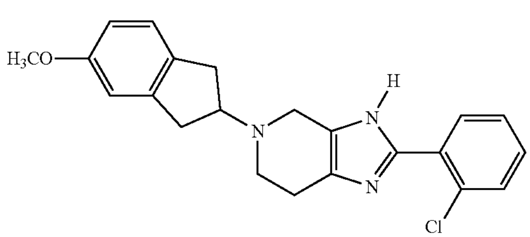 [SMILES: COc1ccc2c(c1)CC(N1CCc3nc(-c4ccccc4Cl)[nH]c3C1)C2] | 2-(2-chlorophenyl)-5-(5-methoxy-2,3-dihydro-1H-inden-2-yl)-4,5,6,7-tetrahydro-3H-imidazo[4,5-c]pyridine |
| 119 | 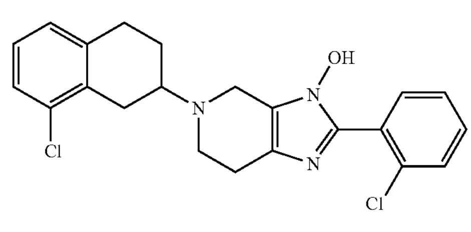 [SMILES: On1c(-c2ccccc2Cl)nc2c1CN(C1CCc3cccc(Cl)c3C1)CC2] | 5-(8-chloro-1,2,3,4-tetrahydronaphthalen-2-yl)-2-(2-chlorophenyl)-4,5,6,7-tetrahydro-3H-imidazo[4,5-c]pyridin-3-ol |

| Ex. No. | Chemical structure | Chemical name |
|---|---|---|
| 120 | 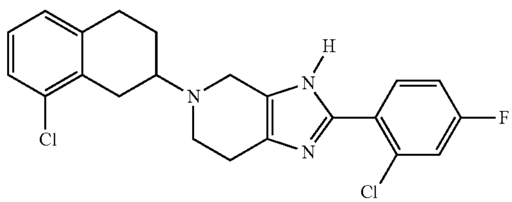 [SMILES: Fc1ccc(-c2nc3c([nH]2)CN(C2CCc4cccc(Cl)c4C2)CC3)c(Cl)c1] | 5-(8-chloro-1,2,3,4-tetrahydronaphthalen-2-yl)-2-(2-chloro-4-fluorophenyl)-4,5,6,7-tetrahydro-3H-imidazo[4,5-c]pyridine |
| 121 | 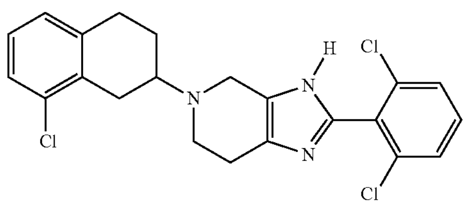 [SMILES: Clc1cccc2c1CC(N1CCc3nc(-c4c(Cl)cccc4Cl)[nH]c3C1)CC2] | 5-(8-chloro-1,2,3,4-tetrahydronaphthalen-2-yl)-2-(2,6-dichlorophenyl)-4,5,6,7-tetrahydro-3H-imidazo[4,5-c]pyridine |
| 122 | 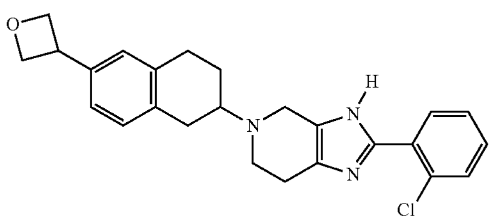 [SMILES: Clc1ccccc1-c1nc2c([nH]1)CN(C1CCc3cc(C4COC4)ccc3C1)CC2] | 2-(2-chlorophenyl)-5-(6-(oxetan-3-yl)-1,2,3,4-tetrahydronaphthalen-2-yl)-4,5,6,7-tetrahydro-3H-imidazo[4,5-c]pyridine |
| 123 | 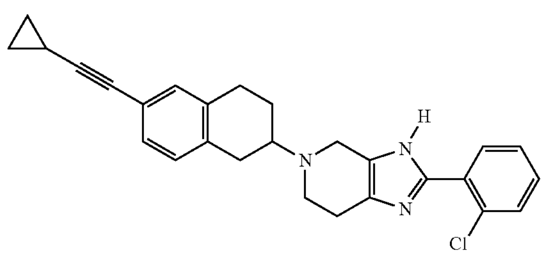 [SMILES: Clc1ccccc1-c1nc2c([nH]1)CN(C1CCc3cc(C#CC4CC4)ccc3C1)CC2] | 2-(2-chlorophenyl)-5-(6-(cyclopropylethynyl)-1,2,3,4-tetrahydronaphthalen-2-yl)-4,5,6,7-tetrahydro-3H-imidazol[4,5-c]pyridine |
| 124 | 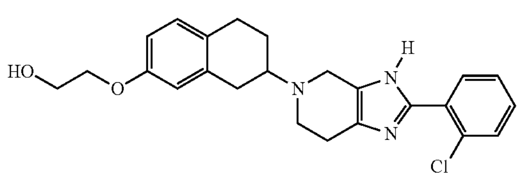 [SMILES: OCCOc1ccc2c(c1)CC(N1CCc3nc(-c4ccccc4Cl)[nH]c3C1)CC2] | 2-((7-(2-(2-chlorophenyl)-3,4,6,7-tetrahydro-5H-imidazo[4,5-c]pyridin-5-yl)-5,6,7,8-tetrahydronaphthalen-2-yl)oxy)ethan-1-ol |
| 125 | 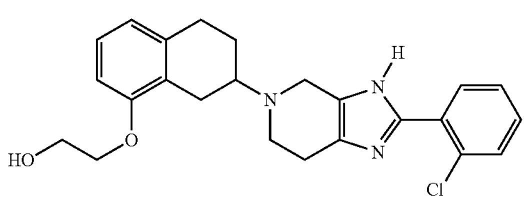 [SMILES: OCCOc1cccc2c1CC(N1CCc3nc(-c4ccccc4Cl)[nH]c3C1)CC2] | 2-((7-(2-(2-chlorophenyl)-3,4,6,7-tetrahydro-5H-imidazo[4,5-c]pyridin-5-yl)-5,6,7,8-tetrahydronaphthalen-1-yl)oxy)ethan-1-ol |
| 126 | 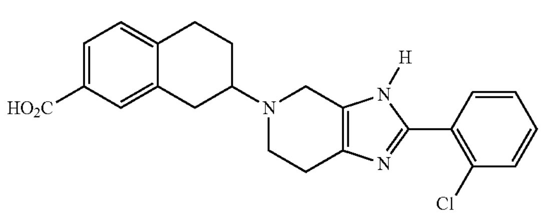 [SMILES: O=C(O)c1ccc2c(c1)CC(N1CCc3nc(-c4ccccc4Cl)[nH]c3C1)CC2] | 7-(2-(2-chlorophenyl)-3,4,6,7-tetrahydro-5H-imidazo[4,5-c]pyridin-5-yl)-5,6,7,8-tetrahydronaphthalene-2-carboxylic acid |

-continued

| Ex. No. | Chemical structure | Chemical name |
|---|---|---|
| 127 | 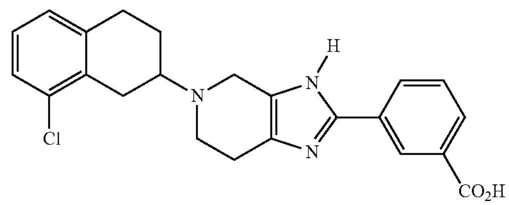 [SMILES: O=C(O)c1cccc(-c2nc3c([nH]2)CN(C2CCc4cccc(Cl)c4C2)CC3)c1] | 3-(5-(8-chloro-1,2,3,4-tetrahydronaphthalen-2-yl)-4,5,6,7-tetrahydro-3H-imidazo[4,5-c]pyridin-2-yl)benzoic acid |
| 128 | 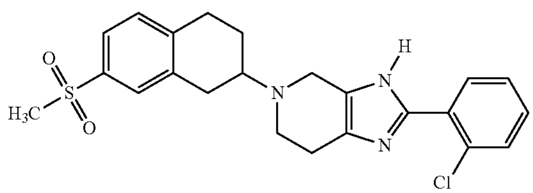 [SMILES: CS(=O)(=O)c1ccc2c(c1)CC(N1CCc3nc(-c4ccccc4Cl)[nH]c3C1)CC2] | 2-(2-chlorophenyl)-5-(7-(methylsulfonyl)-1,2,3,4-tetrahydronaphthalen-2-yl)-4,5,6,7-tetrahydro-3H-imidazo[4,5-c]pyridine |
| 129 | 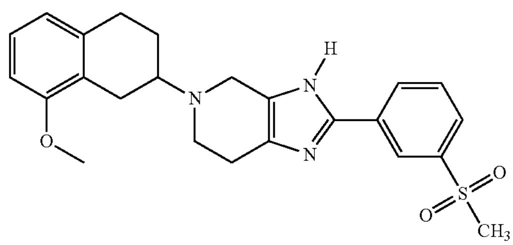 [SMILES: COc1cccc2c1CC(N1CCc3nc(-c4cccc(S(C)(=O)=O)c4)[nH]c3C1)CC2] | 5-(8-methoxy-1,2,3,4-tetrahydronaphthalen-2-yl)-2-(3-(methylsulfonyl)phenyl)-4,5,6,7-tetrahydro-3H-imidazo[4,5-c]pyridine |
| 130 | 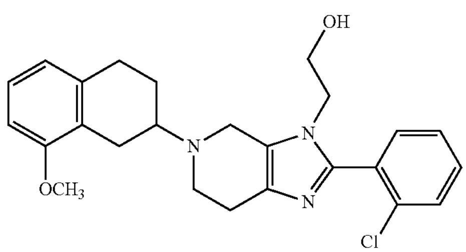 [SMILES: COc1cccc2c1CC(N1CCc3nc(-c4ccccc4Cl)n(CCO)c3C1)CC2] | 2-(2-(2-chlorophenyl)-5-(8-methoxy-1,2,3,4-tetrahydronaphthalen-2-yl)-4,5,6,7-tetrahydro-3H-imidazo[4,5-c]pyridin-3-yl)ethan-1-ol |
| 131 | 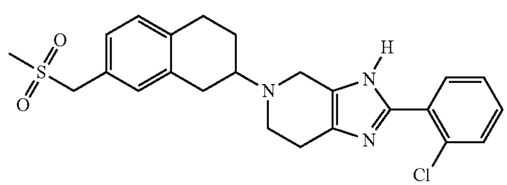 [SMILES: CS(=O)(=O)Cc1ccc2c(c1)CC(N1CCc3nc(-c4ccccc4Cl)[nH]c3C1)CC2] | 2-(2-chlorophenyl)-5-(7-((methylsulfonyl)methyl)-1,2,3,4-tetrahydronaphthalen-2-yl)-4,5,6,7-tetrahydro-3H-imidazo[4,5-c]pyridine |
| 132 | 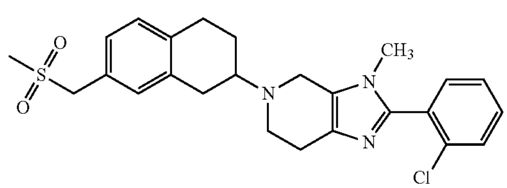 [SMILES: Cn1c(-c2ccccc2Cl)nc2c1CN(C1CCc3ccc(CS(C)(=O)=O)cc3C1)CC2] | 2-(2-chlorophenyl)-3-methyl-5-(7-((methylsulfonyl)methyl)-1,2,3,4-tetrahydronaphthalen-2-yl)-4,5,6,7-tetrahydro-3H-imidazo[4,5-c]pyridine |
| 133 | 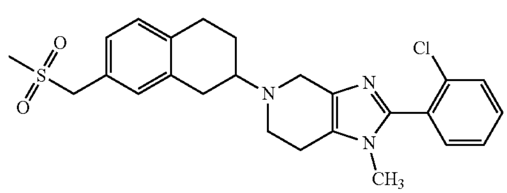 [SMILES: Cn1c(-c2ccccc2Cl)nc2c1CCN(C1CCc3ccc(CS(C)(=O)=O)cc3C1)C2] | 2-(2-chlorophenyl)-1-methyl-5-(7-((methylsulfonyl)methyl)-1,2,3,4-tetrahydronaphthalen-2-yl)-4,5,6,7-tetrahydro-1H-imidazo[4,5-c]pyridine |

| Ex. No. | Chemical structure | Chemical name |
|---|---|---|
| 134 | 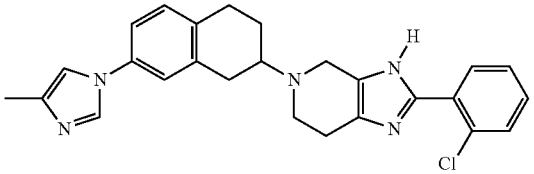 [SMILES: Cc1cn(-c2ccc3c(c2)CC(N2CCc4nc(-c5ccccc5Cl)[nH]c4C2)CC3)cn1] | 2-(2-chlorophenyl)-5-(7-(4-methyl-1H-imidazol-1-yl)-1,2,3,4-tetrahydronaphthalen-2-yl)-4,5,6,7-tetrahydro-3H-imidazo[4,5-c]pyridine |
| 135 | 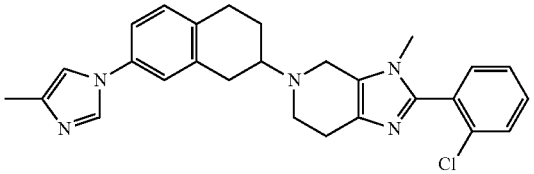 | 2-(2-chlorophenyl)-3-methyl-5-(7-(4-methyl-1H-imidazol-1-yl)-1,2,3,4-tetrahydronaphthalen-2-yl)-4,5,6,7-tetrahydro-3H-imidazo[4,5-c]pyridine |
| 136 | 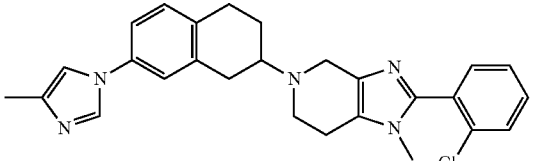 | 2-(2-chlorophenyl)-1-methyl-5-(7-(4-methyl-1H-imidazol-1-yl)-1,2,3,4-tetrahydronaphthalen-2-yl)-4,5,6,7-tetrahydro-1H-imidazo[4,5-c]pyridine |
| 137 | 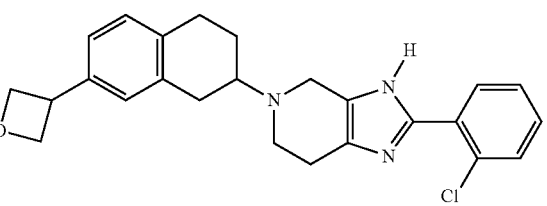 | 2-(2-chlorophenyl)-5-(7-(oxetan-3-yl)-1,2,3,4-tetrahydronaphthalen-2-yl)-4,5,6,7-tetrahydro-3H-imidazo[4,5-c]pyridine |
| 138 | 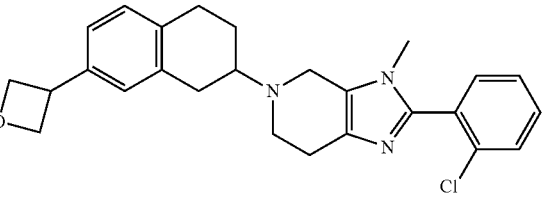 | 2-(2-chlorophenyl)-3-methyl-5-(7-(oxetan-3-yl)-1,2,3,4-tetrahydronaphthalen-2-yl)-4,5,6,7-tetrahydro-3H-imidazo[4,5-c]pyridine |
| 139 | 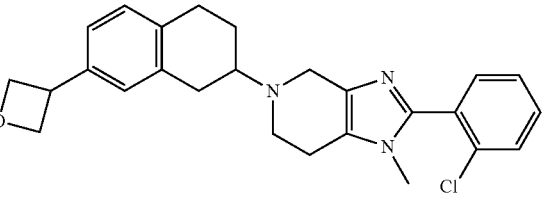 | 2-(2-chlorophenyl)-1-methyl-5-(7-(oxetan-3-yl)-1,2,3,4-tetrahydronaphthalen-2-yl)-4,5,6,7-tetrahydro-1H-imidazo[4,5-c]pyridine |
| 140 | 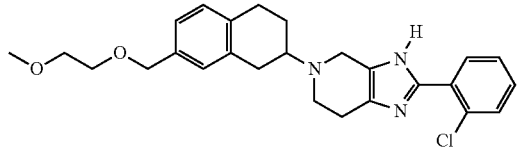 [SMILES: COCCOCc1ccc2c(c1)CC(N1CCc3nc(-c4ccccc4Cl)n(C)c3C1)CC2] | 2-(2-chlorophenyl)-5-(7-((2-methoxyethoxy)methyl)-1,2,3,4-tetrahydronaphthalen-2-yl)-4,5,6,7-tetrahydro-3H-imidazo[4,5-c]pyridine |
| 141 | 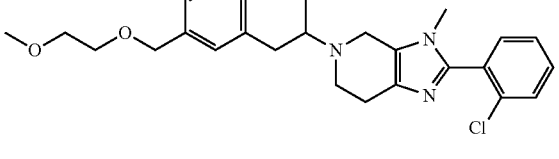 | 2-(2-chlorophenyl)-5-(7-((2-methoxyethoxy)methyl)-1,2,3,4-tetrahydronaphthalen-2-yl)-3-methyl-4,5,6,7-tetrahydro-3H-imidazo[4,5-c]pyridine |

| Ex. No. | Chemical structure | Chemical name |
|---|---|---|
| 142 | 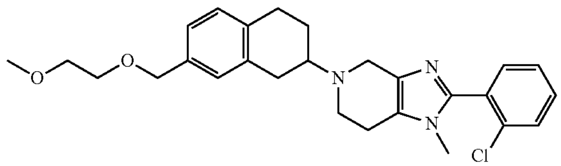 [SMILES: COCCOCc1ccc2c(c1)CC(N1CCc3c(nc(-c4ccccc4Cl)n3C)C1)CC2] | 2-(2-chlorophenyl)-5-(7-((2-methoxyethoxy)methyl)-1,2,3,4-tetrahydronaphthalen-2-yl)-1-methyl-4,5,6,7-tetrahydro-1H-imidazo[4,5-c]pyridine |
| 143 | 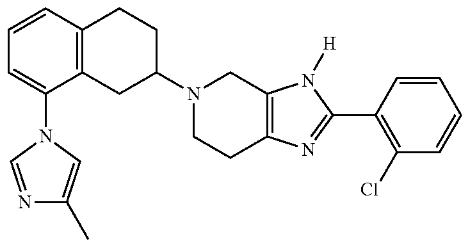 [SMILES: Cc1cn(-c2cccc3c2CC(N2CCc4nc(-c5ccccc5Cl)[nH]c4C2)CC3)cn1] | 2-(2-chlorophenyl)-5-(8-(4-methyl-1H-imidazol-1-yl)-1,2,3,4-tetrahydronaphthalen-2-yl)-4,5,6,7-tetrahydro-3H-imidazo[4,5-c]pyridine |
| 144 | 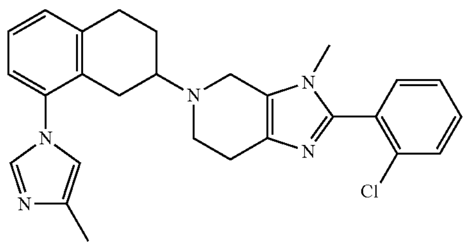 [SMILES: Cc1cn(-c2cccc3c2CC(N2CCc4nc(-c5ccccc5Cl)n(C)c4C2)CC3)cn1] | 2-(2-chlorophenyl)-3-methyl-5-(8-(4-methyl-1H-imidazol-1-yl)-1,2,3,4-tetrahydronaphthalen-2-yl)-4,5,6,7-tetrahydro-3H-imidazo[4,5-c]pyridine |
| 145 | 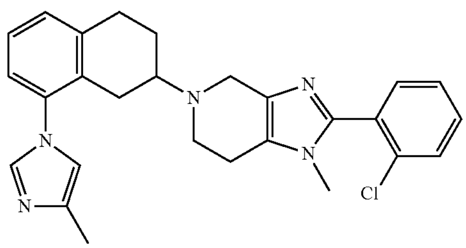 [SMILES: Cc1cn(-c2cccc3c2CC(N2CCc4c(nc(-c5ccccc5Cl)n4C)C2)CC3)cn1] | 2-(2-chlorophenyl)-1-methyl-5-(8-(4-methyl-1H-imidazol-1-yl)-1,2,3,4-tetrahydronaphthalen-2-yl)-4,5,6,7-tetrahydro-1H-imidazo[4,5-c]pyridine |
| 146 | 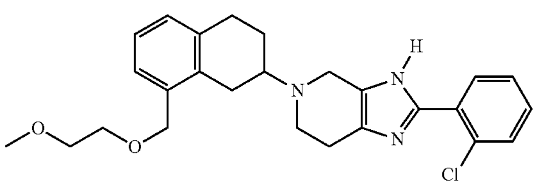 [SMILES: COCCOCc1cccc2c1CC(N1CCc3nc(-c4ccccc4Cl)[nH]c3C1)CC2] | 2-(2-chlorophenyl)-5-(8-((2-methoxyethoxy)methyl)-1,2,3,4-tetrahydronaphthalen-2-yl)-4,5,6,7-tetrahydro-3H-imidazo[4,5-c]pyridine |
| 147 | 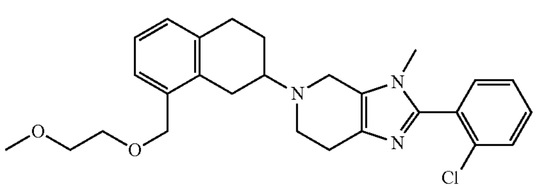 [SMILES: COCCOCc1cccc2c1CC(N1CCc3nc(-c4ccccc4Cl)n(C)c3C1)CC2] | 2-(2-chlorophenyl)-5-(8-((2-methoxyethoxy)methyl)-1,2,3,4-tetrahydronaphthalen-2-yl)-3-methyl-4,5,6,7-tetrahydro-3H-imidazo[4,5-c]pyridine |
| 148 | 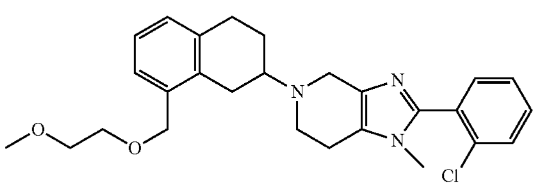 [SMILES: COCCOCc1cccc2c1CC(N1CCc3c(nc(-c4ccccc4Cl)n3C)C1)CC2] | 2-(2-chlorophenyl)-5-(8-((2-methoxyethoxy)methyl)-1,2,3,4-tetrahydronaphthalen-2-yl)-1-methyl-4,5,6,7-tetrahydro-1H-imidazo[4,5-c]pyridine |

| Ex. No. | Chemical structure | Chemical name |
|---|---|---|
| 149 | 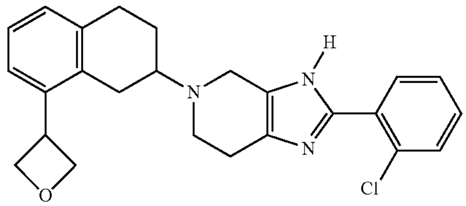 [SMILES: Clc1ccccc1-c1nc2c([nH]1)CN(C1CCc3cccc(C4COC4)c3C1)CC2] | 2-(2-chlorophenyl)-5-(8-(oxetan-3-yl)-1,2,3,4-tetrahydronaphthalen-2-yl)-4,5,6,7-tetrahydro-3H-imidazo[4,5-c]pyridine |
| 150 | 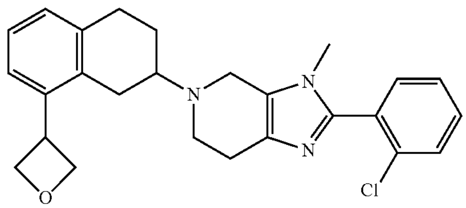 [SMILES: Cn1c(-c2ccccc2Cl)nc2c1CN(C1CCc3cccc(C4COC4)c3C1)CC2] | 2-(2-chlorophenyl)-3-methyl-5-(8-(oxetan-3-yl)-1,2,3,4-tetrahydronaphthalen-2-yl)-4,5,6,7-tetrahydro-3H-imidazo[4,5-c]pyridine |
| 151 | 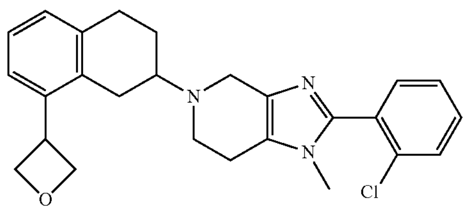 [SMILES: Cn1c(-c2ccccc2Cl)nc2c1CCN(C1CCc3cccc(C4COC4)c3C1)C2] | 2-(2-chlorophenyl)-1-methyl-5-(8-(oxetan-3-yl)-1,2,3,4-tetrahydronaphthalen-2-yl)-4,5,6,7-tetrahydro-1H-imidazo[4,5-c]pyridine |
| 152 | 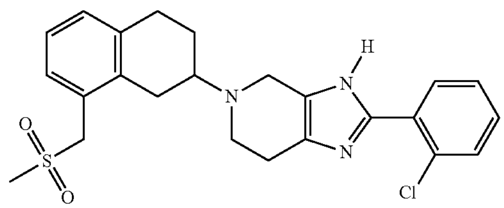 [SMILES: CS(=O)(=O)Cc1cccc2c1CC(N1CCc3nc(-c4ccccc4Cl)[nH]c3C1)CC2] | 2-(2-chlorophenyl)-5-(8-((methylsulfonyl)methyl)-1,2,3,4-tetrahydronaphthalen-2-yl)-4,5,6,7-tetrahydro-3H-imidazo[4,5-c]pyridine |
| 153 | 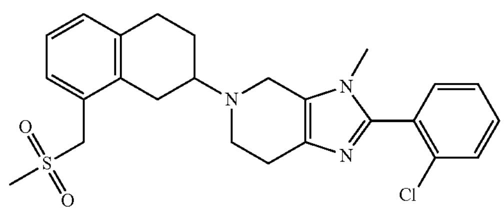 [SMILES: Cn1c(-c2ccccc2Cl)nc2c1CN(C1CCc3cccc(CS(C)(=O)=O)c3C1)CC2] | 2-(2-chlorophenyl)-3-methyl-5-(8-((methylsulfonyl)methyl)-1,2,3,4-tetrahydronaphthalen-2-yl)-4,6,6,7-tetrahydro-3H-imidazo[4,5-c]pyridine |
| 154 | 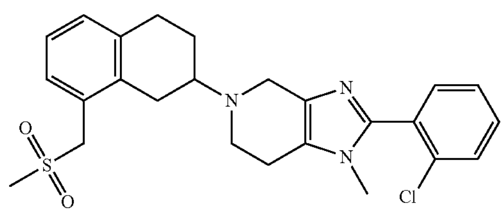 [SMILES: Cn1c(-c2ccccc2Cl)nc2c1CCN(C1CCc3cccc(CS(C)(=O)=O)c3C1)C2] | 2-(2-chlorophenyl)-1-methyl-5-(8-((methylsulfonyl)methyl)-1,2,3,4-tetrahydronaphthalen-2-yl)-4,6,6,7-tetrahydro-1H-imidazo[4,5-c]pyridine |
| 155 | 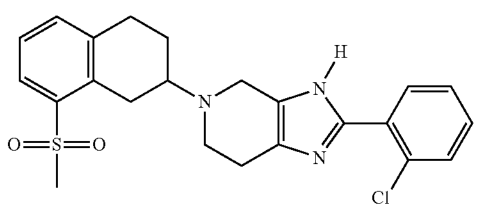 [SMILES: CS(=O)(=O)c1cccc2c1CC(N1CCc3nc(-c4ccccc4Cl)[nH]c3C1)CC2] | 2-(2-chlorophenyl)-5-(8-(methylsulfonyl)-1,2,3,4-tetrahydronaphthalen-2-yl)-4,6,6,7-tetrahydro-3H-imidazo[4,5-c]pyridine |

-continued

| Ex. No. | Chemical structure | Chemical name |
|---|---|---|
| 156 | 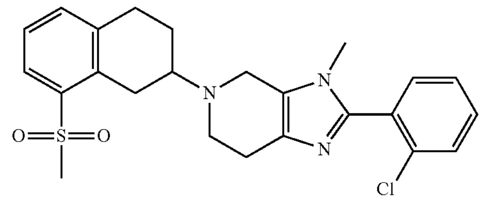 [SMILES: Cn1c(-c2ccccc2Cl)nc2c1CN(C1CCc3cccc(S(C)(=O)=O)c3C1)CC2] | 2-(2-chlorophenyl)-3-methyl-5-(8-(methylsulfonyl)-1,2,3,4-tetrahydronaphthalen-2-yl)-4,6,6,7-tetrahydro-3H-imidazo[4,5-c]pyridine |
| 157 | 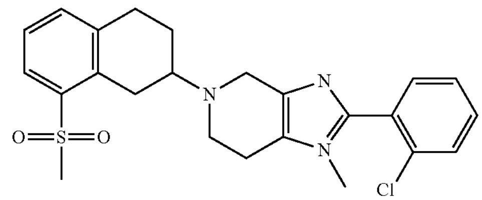 | 2-(2-chlorophenyl)-1-methyl-5-(8-(methylsulfonyl)-1,2,3,4-tetrahydronaphthalen-2-yl)-4,6,6,7-tetrahydro-1H-imidazo[4,5-c]pyridine |
| 158 | 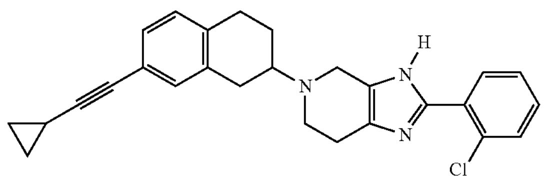 [SMILES: Clc1ccccc1-c1nc2c([nH]1)CN(C1CCc3ccc(C#CC4CC4)cc3C1)CC2] | 2-(2-chlorophenyl)-5-(7-(cyclopropylethynyl)-1,2,3,4-tetrahydronaphthalen-2-yl)-4,6,6,7-tetrahydro-3H-imidazo[4,5-c]pyridine |
| 159 | 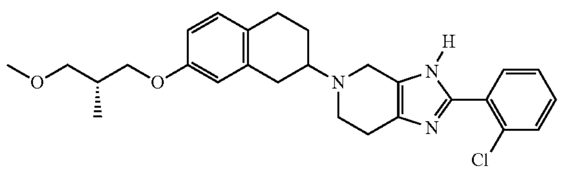 [SMILES: COC[C@@H](C)COc1ccc2c(c1)CC(N1CCc3nc(-c4ccccc4Cl)[nH]c3C1)CC2] | (2R)-1-((7-(2-(2-chlorophenyl)-3,4,6,7-tetrahydro-5H-1-imidazo[4,5-c]pyridin-5-yl)-5,6,7,8-tetrahydronaphthalen-2-yl)oxy)-3-methoxypropan-2-ol |
| 160 | 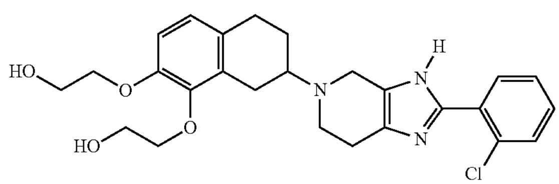 [SMILES: OCCOc1ccc2c(c1OCCO)CC(N1CCc3nc(-c4ccccc4Cl)[nH]c3C1)CC2] | 2,2'-((7-(2-(2-chlorophenyl)-3,4,6,7-tetrahydro-5H-imidazo[4,5-c]pyridin-5-yl)-5,6,7,8-tetrahydronaphthalene-1,2-diyl)bis(oxy))bis(ethan-1-ol) |
| 161 | 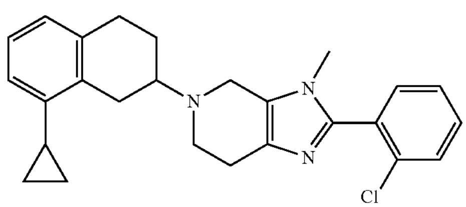 [SMILES: Cn1c(-c2ccccc2Cl)nc2c1CN(C1CCc3cccc(C4CC4)c3C1)CC2] | 2-(2-chlorophenyl)-5-(8-cyclopropyl-1,2,3,4-tetrahydronaphthalen-2-yl)-3-methyl-4,5,6,7-tetrahydro-3H-imidazo[4,5-c]pyridine |
| 162 | 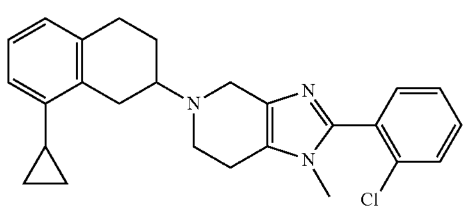 [SMILES: Cn1c(-c2ccccc2Cl)nc2c1CCN(C1CCc3cccc(C4CC4)c3C1)C2] | 2-(2-chlorophenyl)-5-(8-cyclopropyl-1,2,3,4-tetrahydronaphthalen-2-yl)-1-methyl-4,5,6,7-tetrahydro-1H-imidazo[4,5-c]pyridine |
| 163 | 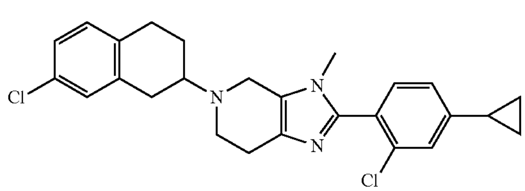 [SMILES: Cn1c(-c2ccc(C3CC3)cc2Cl)nc2c1CN(C1CCc3ccc(Cl)cc3C1)CC2] | 5-(7-chloro-1,2,3,4-tetrahydronaphthalen-2-yl)-2-(2-chloro-4-cyclopropylphenyl)-3-methyl-4,5,6,7-tetrahydro-3H-imidazo[4,5-c]pyridine |

| Ex. No. | Chemical structure | Chemical name |
|---|---|---|
| 164 | 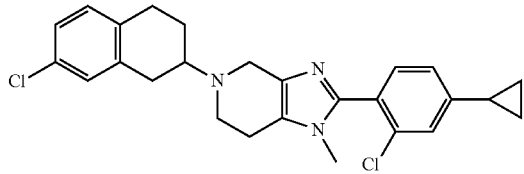 [SMILES: Cn1c(-c2ccc(C3CC3)cc2Cl)nc2c1CCN(C1CCc3ccc(Cl)cc3C1)C2] | 5-(7-chloro-1,2,3,4-tetrahydronaphthalen-2-yl)-2-(2-chloro-4-cyclopropylphenyl)-1-methyl-4,5,6,7-tetrahydro-1H-imidazo[4,5-c]pyridine |
| 165 | 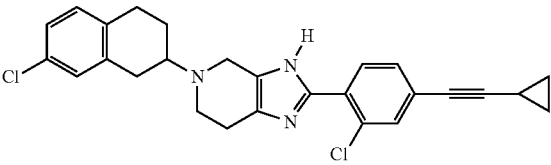 [SMILES: Clc1ccc2c(c1)CC(N1CCc3nc(-c4ccc(C#CC5CC5)cc4Cl)[nH]c3C1)CC2] | 5-(7-chloro-1,2,3,4-tetrahydronaphthalen-2-yl)-2-(2-chloro-4-(cyclopropylethynyl)phenyl)-4,5,6,7-tetrahydro-3H-imidazo[4,5-c]pyridine |
| 166 | 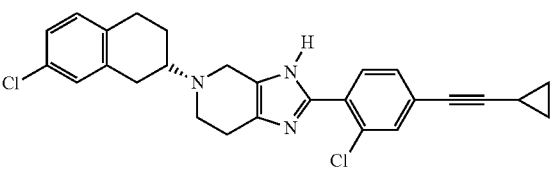 | (S)-5-(7-chloro-1,2,3,4-tetrahydronaphthalen-2-yl)-2-(2-chloro-4-(cyclopropylethynyl)phenyl)-4,5,6,7-tetrahydro-3H-imidazo[4,5-c]pyridine |
| 167 | 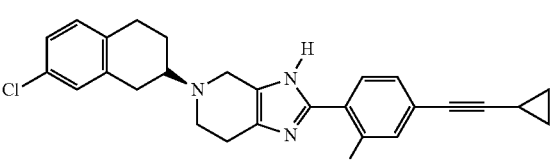 | (R)-5-(7-chloro-1,2,3,4-tetrahydronaphthalen-2-yl)-2-(2-chloro-4-(cyclopropylethynyl)phenyl)-4,5,6,7-tetrahydro-3H-imidazo[4,5-c]pyridine |
| 168 | 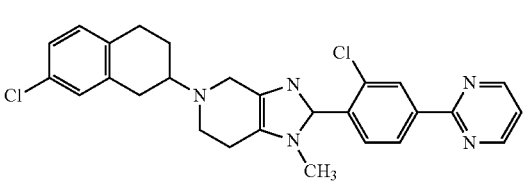 [SMILES: CN1C2=C(CN(C3CCc4ccc(Cl)cc4C3)CC2)NC1c1ccc(-c2ncccn2)cc1Cl] | 5-(7-chloro-1,2,3,4-tetrahydronaphthalen-2-yl)-2-(2-chloro-4-(pyrimidin-2-yl)phenyl)-1-methyl-4,5,6,7-tetrahydro-1H-imidazo[4,5-c]pyridine |
| 169 | 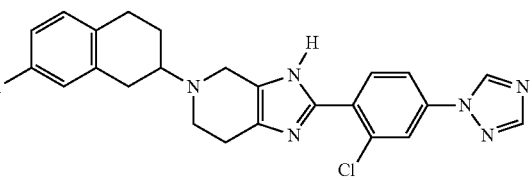 | 5-(7-chloro-1,2,3,4-tetrahydronaphthalen-2-yl)-2-(2-chloro-4-(1H-1,2,4-triazol-1-yl)phenyl)-4,5,6,7-tetrahydro-3H-imidazo[4,5-c]pyridine |
| 170 | 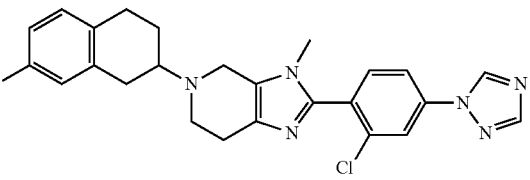 | 5-(7-chloro-1,2,3,4-tetrahydronaphthalen-2-yl)-2-(2-chloro-4-(1H-1,2,4-triazol-1-yl)phenyl)-3-methyl-4,5,6,7-tetrahydro-3H-imidazo[4,5-c]pyridine |
| 171 | 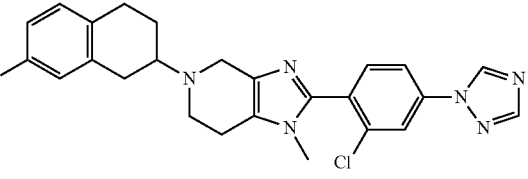 | 5-(7-chloro-1,2,3,4-tetrahydronaphthalen-2-yl)-2-(2-chloro-4-(1H-1,2,4-triazol-1-yl)phenyl)-1-methyl-4,5,6,7-tetrahydro-1H-imidazo[4,5-c]pyridine |

| Ex. No. | Chemical structure | Chemical name |
|---|---|---|
| 172 | 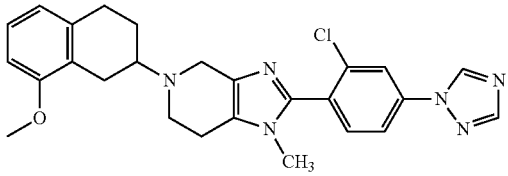 [SMILES: COc1cccc2c1CC(N1CCc3c(nc(-c4ccc(-n5cncn5)cc4Cl)n3C)C1)CC2] | 2-(2-chloro-4-(1H-1,2,4-triazol-1-yl)phenyl)-5-(8-methoxy-1,2,3,4-tetrahydronaphthalen-2-yl)-1-methyl-4,5,6,7-tetrahydro-1H-imidazo[4,5-c]pyridine |
| 173 | 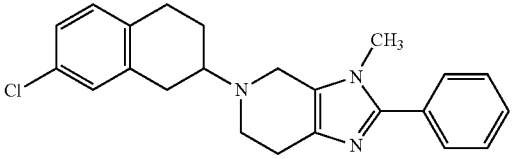 [SMILES: Cn1c(-c2ccccc2)nc2c1CN(C1CCc3ccc(Cl)cc3C1)CC2] | 5-(7-chloro-1,2,3,4-tetrahydronaphthalen-2-yl)-3-methyl-2-phenyl-4,5,6,7-tetrahydro-3H-imidazo[4,5-c]pyridine |
| 174 | 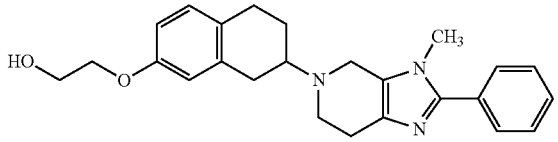 [SMILES: Cn1c(-c2ccccc2)nc2c1CN(C1CCc3ccc(OCCO)cc3C1)CC2] | 2-((7-(3-methyl-2-phenyl-3,4,6,7-tetrahydro-5H-imidazo[4,5-c]pyridin-5-yl)-5,6,7,8-tetrahydronaphthalen-2-yl)oxy)ethan-1-ol |
| 175 | 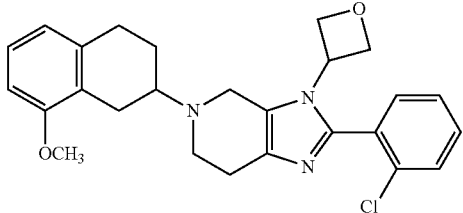 [SMILES: COc1cccc2c1CC(N1CCc3nc(-c4ccccc4Cl)n(C4COC4)c3C1)CC2] | 2-(2-chlorophenyl)-5-(8-methoxy-1,2,3,4-tetrahydronaphthalen-2-yl)-3-(oxetan-3-yl)-4,5,6,7-tetrahydro-3H-imidazo[4,5-c]pyridine |
| 176 | 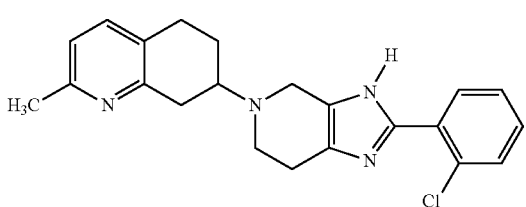 [SMILES: Cc1ccc2c(n1)CC(N1CCc3nc(-c4ccccc4Cl)[nH]c3C1)CC2] | 7-(2-(2-chlorophenyl)-3,4,6,7-tetrahydro-5H-imidazo[4,5-c]pyridin-5-yl)-2-methyl-5,6,7,8-tetrahydroquinoline |
| 177 | 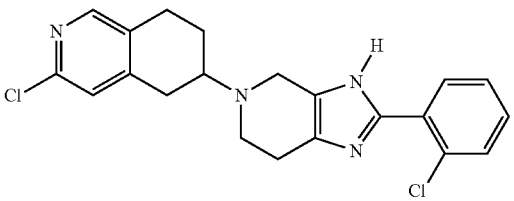 [SMILES: Clc1cc2c(cn1)CCC(N1CCc3nc(-c4ccccc4Cl)[nH]c3C1)C2] | 6-(2-(2-chlorophenyl)-3,4,6,7-tetrahydro-5H-imidazo[4,5-c]pyridin-5-yl)-3-methyl-5,6,7,8-tetrahydroisoquinoline |
| 178 | 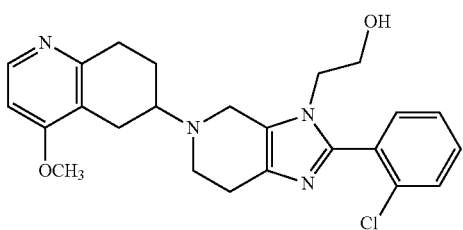 [SMILES: COc1ccnc2c1CC(N1CCc3nc(-c4ccccc4Cl)n(CCO)c3C1)CC2] | 2-(2-(2-chlorophenyl)-5-(4-methoxy-5,6,7,8-tetrahydroquinolin-6-yl)-4,5,6,7-tetrahydro-3H-imidazo[4,5-c]pyridin-3-yl)ethan-1-ol |

-continued

| Ex. No. | Chemical structure | Chemical name |
|---|---|---|
| 179 | 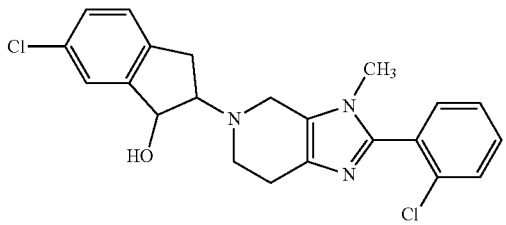 [SMILES: Cn1c(-c2ccccc2Cl)nc2c1CN(C1Cc3ccc(Cl)cc3C1O)CC2] | 6-chloro-2-(2-(2-chlorophenyl)-3-methyl-3,4,6,7-tetrahydro-5H-imidazo[4,5-c]pyridin-5-yl)-2,3-dihydro-1H-inden-1-ol |
| 180 | 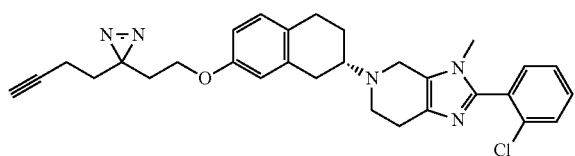 [SMILES: C#CCCC1(CCOc2ccc3c(c2)C[C@@H](N2CCc4nc(-c5ccccc5Cl)n(C)c4C2)CC3)N=N1] | (S)-5-(7-(2-(3-(but-3-yn-1-yl)-3H-diazirin-3-yl)ethoxy)-1,2,3,4-tetrahydronaphthalen-2-yl)-2-(2-chlorophenyl)-3-methyl-4,5,6,7-tetrahydro-3H-imidazo[4,5-c]pyridine |
| 181 | 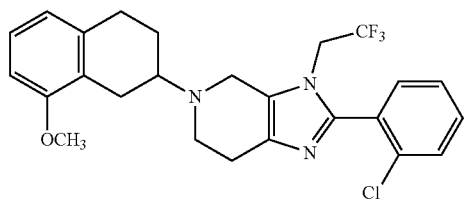 [SMILES: COc1cccc2c1CC(N1CCc3nc(-c4ccccc4Cl)n(CC(F)(F)F)c3C1)CC2] | 2-(2-chlorophenyl)-5-(8-methoxy-1,2,3,4-tetrahydronaphthalen-2-yl)-3-(2,2,2-trifluoroethyl)-4,5,6,7-tetrahydro-3H-imidazo[4,5-c]pyridine |
| 182 | 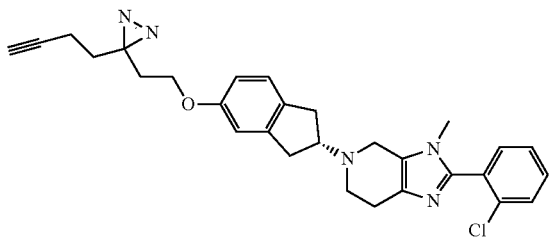 [SMILES: C#CCCC1(CCOc2ccc3c(c2)C[C@@H](N2CCc4nc(-c5ccccc5Cl)n(C)c4C2)C3)N=N1] | 5-(5-(2-(3-(but-3-yn-1-yl)-3H-diazirin-3-yl)ethoxy)-2,3-dihydro-1H-inden-2-yl)-2-(2-chlorophenyl)-3-methyl-4,5,6,7-tetrahydro-3H-imidazo[4,5-c]pyridine |
| 183 | 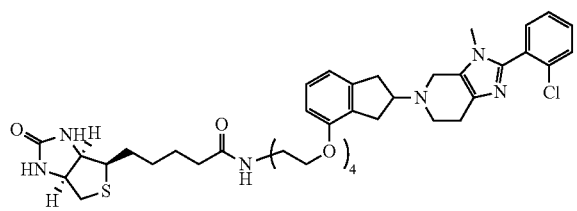 | N-(2-(2-(2-(2-((2-(2-(2-chlorophenyl)-3-methyl-3,4,6,7-tetrahydro-5H-imidazo[4,5-c]pyridin-5-yl)-2,3-dihydro-1H-inden-4-yl)oxy)ethoxy)ethoxy)ethoxy)ethyl)-5-((3aR,4R,6aS)-2-oxohexahydro-1H-thieno[3,4-d]imidazol-4-yl)pentanamide |
| 184 | 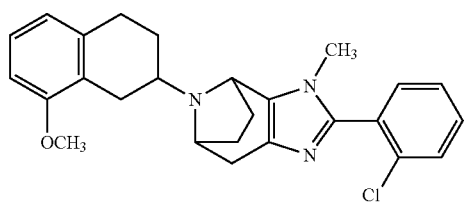 [SMILES: COc1cccc2c1CC(N1C3CCC1c1c(nc(-c4ccccc4Cl)n1C)C3)CC2] | 2-(2-chlorophenyl)-9-(8-methoxy-1,2,3,4-tetrahydronaphthalen-2-yl)-3-methyl-3,4,5,6,7,8-hexahydro-4,7-epiminocyclohepta[d]imidazole |

Example 185: 8-chloro-2-(2-(2-chlorophenyl)-4,5,6,7-tetrahydro-1H-benzo[d]imidazol-6-yl)-1,2,3,4-tetrahydroisoquinoline

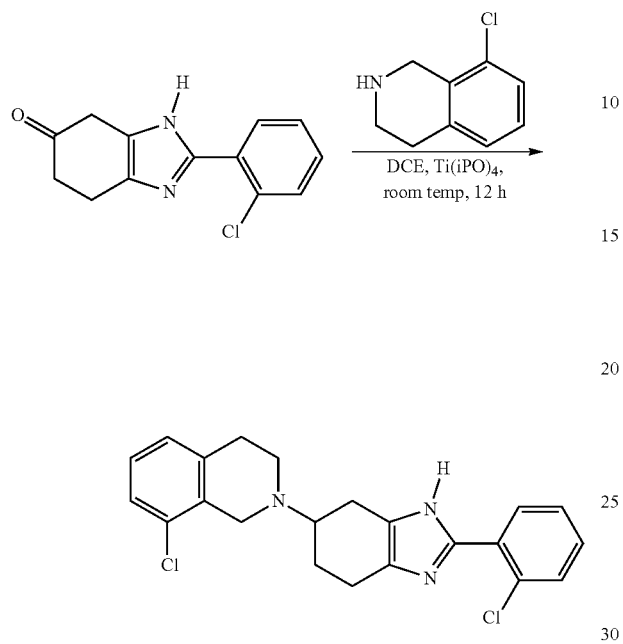

To a solution of 2-(2-chlorophenyl)-3,4,6,7-tetrahydro-5H-benzo[d]imidazol-5-one (70 mg, 0.28 mmol) and 8-chloro-1,2,3,4-tetrahydroisoquinoline (50 mg, 0.3 mmol) in 1,2-dichloroethane (30 mL) was added Ti(iPrO)$_4$ (159 mg, 0.56 mmol). The mixture was stirred at room temperature for 12 hours under nitrogen atmosphere. The mixture was diluted with dichloromethane (60 mL), washed with sat. NaHCO$_3$ solution (30 mL), water (30 mL), brine (30 mL), dried, concentrated, and purified on prep-TLC (20:1 dichloromethane:methanol) to afford 8-chloro-2-(2-(2-chlorophenyl)-4,5,6,7-tetrahydro-1H-benzo[d]imidazol-6-yl)-1,2,3,4-tetrahydroisoquinoline (5 mg, 4% yield) as white solid. MS (ESI): mass calcd. for C$_{22}$H$_{21}$Cl$_2$N$_3$ 397.11, m/z found 397.7 [M+H]$^+$. $^1$H NMR (400 MHz, CD$_3$OD) δ ppm 7.72 (dt, J=6.6, 3.1 Hz, 1H), 7.56 (dd, J=6.0, 3.3 Hz, 1H), 7.49-7.33 (m, 2H), 7.23 (m, 3H), 4.26-4.04 (m, 2H), 3.46-3.34 (m, 1H), 3.27-2.98 (m, 5H), 2.98-2.75 (m, 3H), 2.39 (d, J=11.4 Hz, 1H), 2.01 (dd, J=12.0, 5.4 Hz, 1H).

8-chloro-2-(2-(2-chlorophenyl)-4,5,6,7-tetrahydro-1H-benzo[d]imidazol-6-yl)-1,2,3,4-tetra-hydroisoquinoline (300 mg, 0.75 mmol) was separated by chiral separation. This resulted Example 185-R: (R)-8-chloro-2-(2-(2-chlorophenyl)-4,5,6,7-tetrahydro-1H-benzo[d]imidazol-6-yl)-1,2,3,4-tetrahydroisoquinoline (50 mg, 16.7%) as white solid (MS (ESI): mass calcd. for C$_{22}$H$_{21}$Cl$_2$N$_3$ 397.11, m/z found 397.8 [M+H]$^+$. $^1$H NMR (400 MHz, CD$_3$OD) δ ppm 8.34 (s, 1H), 7.79-7.67 (m, 1H), 7.62-7.52 (m, 1H), 7.50-7.39 (m, 2H), 7.28 (d, J=7.6 Hz, 1H), 7.23 (d, J=7.5 Hz, 1H), 7.18 (t, J=7.8 Hz, 1H), 4.11 (s, 2H), 3.43-3.36 (m, 1H), 3.27-3.16 (m, 1H), 3.13-2.96 (m, 4H), 2.98-2.73 (m, 4H)) and Example 185-S: (S)-8-chloro-2-(2-(2-chlorophenyl)-4,5,6,7-tetrahydro-1H-benzo[d]imidazol-6-yl)-1,2,3,4-tetrahydroisoquinoline (60 mg, 20%) as white solid (MS (ESI): mass calcd. for C$_{22}$H$_{21}$Cl$_2$N$_3$ 397.11, m/z found 397.8 [M+H]$^+$. $^1$H NMR (400 MHz, CD$_3$OD) δ ppm 8.31 (d, J=11.1 Hz, 1H), 7.77-7.68 (m, 1H), 7.61-7.53 (m, 1H), 7.50-7.39 (m, 2H), 7.29 (d, J=7.8 Hz, 1H), 7.23 (t, J=7.7 Hz, 1H), 7.18 (d, J=7.6 Hz, 1H), 4.13 (s, 2H), 3.43 (s, 1H), 3.25 (s, 1H), 3.17-3.01 (m, 4H), 2.99-2.87 (m, 2H), 2.86-2.77 (m, 1H), 2.40 (d, J=10.3 Hz, 1H), 2.09-1.96 (m, 1H)).

Example 186: 6-(4-chloroisoindolin-2-yl)-2-(2-chlorophenyl)-4,5,6,7-tetrahydro-1H-benzo[d]imidazole

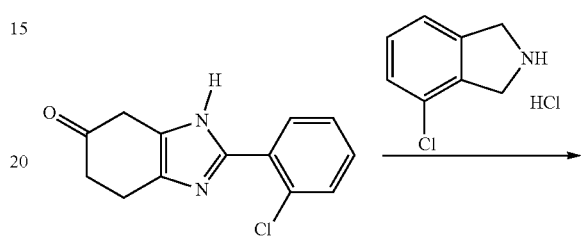

To a solution of 2-(2-chlorophenyl)-3,4,6,7-tetrahydro-5H-benzo[d]imidazol-5-one and 4-chloroisoindoline hydrochloride (47 mg, 0.25 mmol) in 1,2-dichloroethane (30 mL) was added N,N-diisopropylethylamine (33 mg, 0.25 mmol). The mixture was stirred at room temperature for 30 mins under nitrogen atmosphere. 2-(2-chlorophenyl)-3,4,6,7-tetrahydro-5H-benzo[d]imidazol-5-one (60 mg, 0.25 mmol) was added, followed by acetic acid (1 drop). The solution was stirred at room temperature for 6 hours. NaBH$_3$CN (80 mg, 0.38 mmol) was added. The solution was stirred at room temperature for 12 hours. The reaction solution was quenched with water (50 mL) and separated. The organic phase was washed with brine (30 mL), dried, concentrated and purified by prep-HPLC to afford 6-(4-chloroisoindolin-2-yl)-2-(2-chlorophenyl)-4,5,6,7-tetrahydro-1H-benzo[d]imidazole (28 mg, 29% yield). MS (ESI): mass calcd. for C$_{21}$H$_{19}$Cl$_2$N$_3$ 383.10, m/z found 383.8 [M+H]$^+$. $^1$H NMR (400 MHz, CD$_3$OD) δ ppm 8.26 (s, 1H), 7.72 (dd, J=6.0, 3.3 Hz, 1H), 7.63-7.53 (m, 1H), 7.51-7.39 (m, 2H), 7.34-7.26 (m, 2H), 4.44-4.25 (m, 3H), 3.31-3.21 (m, 1H), 3.19-3.11 (m, 1H), 2.84 (dt, J=22.8, 14.7 Hz, 3H), 2.42 (d, J=13.0 Hz, 1H), 1.98 (d, J=21.3 Hz, 1H).

Examples 187 and 188: 8-chloro-2-(2-(2-chlorophenyl)-1-methyl-4,5,6,7-tetrahydro-1H-benzo[d]imidazol-6-yl)-1,2,3,4-tetrahydroisoquinoline and 8-chloro-2-(2-(2-chlorophenyl)-1-methyl-4,5,6,7-tetrahydro-1H-benzo[d]imidazol-5-yl)-1,2,3,4-tetrahydroisoquinoline

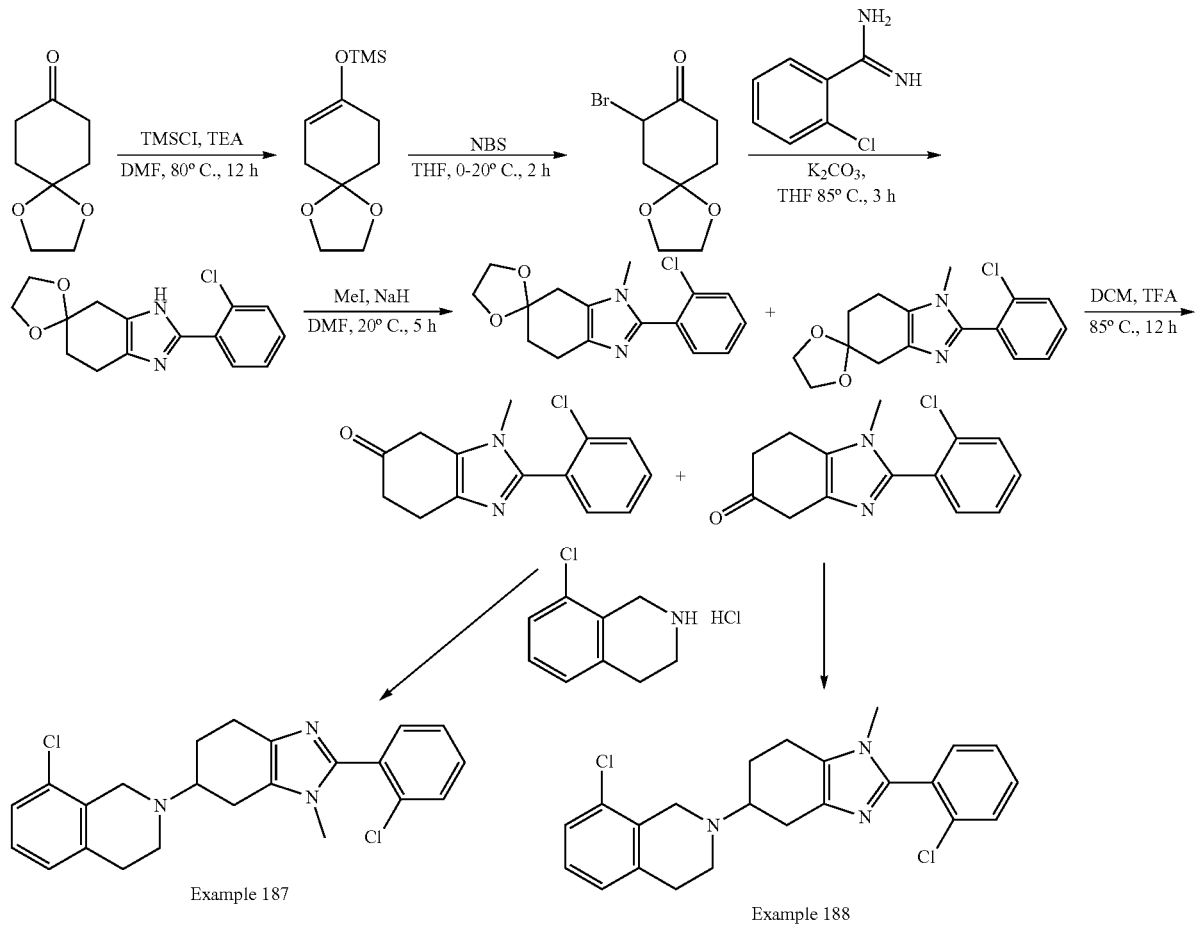

To a mixture of 1,4-dioxaspiro[4.5]decan-8-one (50 g, 320.15 mmol) in dimethylformamide (400 mL) was added triethylamine (64.79 g, 640.29 mmol, 89.12 mL) and chloro(trimethyl)silane (69.56 g, 640.29 mmol, 81.26 mL). The mixture was heated to 80° C. and stirred for 12 hours. The reaction mixture was quenched by addition water (100 mL) at 20° C. and then it was diluted with water (300 mL). The mixture was extracted with ethyl acetate (200 mL×3). The combined organic layers were washed with water (500 mL×3) and brine (500 mL), dried over Na₂SO₄, filtered and concentrated under reduced pressure to give a residue, which was purified by column chromatography (SiO₂, petroleum ether). 1,4-dioxaspiro[4.5]dec-7-en-8-yloxy(trimethyl)silane (40 g, 175.16 mmol, 54.71% yield) was obtained as a yellow oil.

To a solution of 1,4-dioxaspiro[4.5]dec-7-en-8-yloxy (trimethyl)silane (70 g, 306.53 mmol) in tetrahydrofuran (500 mL) was added N-bromosuccinimide (54.56 g, 306.53 mmol) at 0° C. The mixture was stirred at 20° C. for 2 hr, and the obtained 7-bromo-1,4-dioxaspiro[4.5]decan-8-one was used directly in the next step without work-up or purification.

To a solution of 7-bromo-1,4-dioxaspiro[4.5]decan-8-one and 2-chlorobenzamidine (46.04 g, 297.78 mmol) in tetrahydrofuran (500 mL) was added K₂CO₃ (102.89 g, 744.44 mmol) in one portion under N₂. The mixture was heated to 85° C. and stirred for 3 hours. The reaction mixture was diluted with water (200 mL) and extracted with ethyl acetate (200 mL×3). The combined organic layers were washed with brine (500 mL), dried over Na₂SO₄, filtered and concentrated under reduced pressure to give a residue, which was purified by column chromatography (SiO₂, petroleum ether:ethyl acetate (1:0 to 0:1)). 2-(2-chlorophenyl)-3,4,6,7-tetrahydrospiro[benzo[d]imidazole-5,2'-[1,3]dioxolane] (50 g, 171.97 mmol, 57.75% yield) was obtained as a yellow solid. ¹H NMR (400 MHz, CDCl₃): δ ppm 9.92 (br, 1H), 8.23 (d, J=6.4 Hz, 1H), 7.39 (d, J=8 Hz, 1H), 7.38-7.24 (m, 2H), 4.05 (s, 4H), 2.95 (s, 2H), 2.80 (t, J=2.0 Hz, 2H), 2.04 (t, J=2.0 Hz, 2H).

To a solution of 2-(2-chlorophenyl)-3,4,6,7-tetrahydrospiro[benzo[d]imidazole-5,2'-[1,3]dioxolane] (20 g, 68.79 mmol) in dimethylformamide (200 mL) was slowly added NaH (3.30 g, 82.55 mmol) at 20° C. After addition, the mixture was stirred at 20° C. for 1 hr, and then iodomethane (11.72 g, 82.55 mmol) was added dropwise at 20° C. The resulting mixture was stirred at 20° C. for 4 hr. The reaction mixture was quenched by dropwise addition water (50 mL) at 0° C., diluted with water (200 mL) and extracted with ethyl acetate (300 mL×3). The combined organic layers were washed with water 200 mL (100 mL×2) and brine 200 mL, dried over $Na_2SO_4$, filtered and concentrated under reduced pressure to give a residue, which was purified by column chromatography ($SiO_2$, petroleum ether:ethyl acetate (1:0 to 0:1)). A mixture of 2-(2-chlorophenyl)-3-methyl-3,4,6,7-tetrahydrospiro[benzo[d]imidazole-5,2'-[1,3]dioxolane] and 2-(2-chlorophenyl)-3-methyl-3,4,6,7-tetrahydrospiro[benzo[d]imidazole-6,2'-[1,3]dioxolane] was obtained as a brown oil (13 g, crude).

A mixture of 2-(2-chlorophenyl)-3-methyl-3,4,6,7-tetrahydrospiro[benzo[d]imidazole-5,2'-[1,3]dioxolane] and 2-(2-chlorophenyl)-3-methyl-3,4,6,7-tetrahydrospiro[benzo[d]imidazole-6,2'-[1,3]dioxolane] (13 g, 42.66 mmol) in trifluoroacetic acid (50 mL) and dichloromethane (10 mL) was degassed and purged with $N_2$ for 3 times, and then the mixture was stirred at 85° C. for 12 hr under $N_2$ atmosphere. The reaction mixture was concentrated under reduced pressure. The residue was diluted with aqueous $NaHCO_3$ (200 mL) and extracted with ethyl acetate (200 mL×5). The combined organic layers were washed with brine 300 mL, dried over $Na_2SO_4$, filtered and concentrated under reduced pressure to give a residue, which was first purified by column chromatography ($SiO_2$, petroleum ether:ethyl acetate (1:0 to 0:1)). The mixture was then purified by supercritical fluid chromatography (column: DAICEL CHIRALPAK IC (250 mm×50 mm, 10 μm); mobile phase: 0.1% $NH_3H_2O$ ethanol; B %: 50%-50%, 6 minutes). 2-(2-chlorophenyl)-3-methyl-3,4,6,7-tetrahydro-5H-benzo[d]imidazol-5-one ($^1$H NMR (400 MHz, $CDCl_3$): δ ppm 7.48-7.35 (m, 4H), 3.48-3.37 (m, 2H), 3.37 (s, 3H), 3.04 (t, J=6.8 Hz, 2H), 2.78 (t, J=6.8 Hz, 2H)) and 2-(2-chlorophenyl)-1-methyl-1,4,6,7-tetrahydro-5H-benzo[d]imidazol-5-one were obtained.

2-(2-chlorophenyl)-3-methyl-3,4,6,7-tetrahydro-5H-benzo[d]imidazol-5-one was coupled with 8-chloro-1,2,3,4-tetrahydroisoquinoline in a same manner as in Example 185 to obtain Example 187, 8-chloro-2-(2-(2-chlorophenyl)-1-methyl-4,5,6,7-tetrahydro-1H-benzo[d]imidazol-6-yl)-1,2,3,4-tetrahydroisoquinoline (ESI-MS [M+H]$^+$: 412.1; $^1$H NMR (400 MHz, $CD_3OD$): δ ppm 7.78-7.75 (m, 2H), 7.67-7.64 (m, 2H), 7.42 (d, J=8.0 Hz, 1H), 7.37 (m, 1H), 7.30 (t, J=6.8 Hz, 1H), 4.66-4.60 (m, 2H), 4.05 (m, 1H), 3.68-3.36 (m, 5H), 3.33 (m, 3H), 3.04 (m, 3H), 2.59 (m, 1H), 2.30 (m, 1H)) and 2-(2-chlorophenyl)-1-methyl-1,4,6,7-tetrahydro-5H-benzo[d]imidazol-5-one was coupled with 8-chloro-1,2,3,4-tetrahydroisoquinoline in a same manner as in Example 185 to obtain Example 188, 8-chloro-2-(2-(2-chlorophenyl)-1-methyl-4,5,6,7-tetrahydro-1H-benzo[d]imidazol-5-yl)-1,2,3,4-tetrahydroisoquinoline (ESI-MS [M+H]$^+$: 412.1; $^1$H NMR (400 MHz, $CD_3OD$): δ ppm 7.75-7.63 (m, 4H), 7.42 (d, J=8.0 Hz, 1H), 7.39-7.37 (m, 1H), 7.30 (d, J=8.0 Hz, 1H), 4.61-4.55 (m, 2H), 4.05 (m, 1H), 3.68-3.62 (m, 5H), 3.15-3.14 (m, 3H), 3.09-2.95 (m, 3H), 2.64 (m, 1H), 2.30 (m, 1H)).

8-chloro-2-(2-(2-chlorophenyl)-1-methyl-4,5,6,7-tetrahydro-1H-benzo[d]imidazol-6-yl)-1,2,3,4-tetrahydroisoquinoline was separated by chiral separation. This resulted in Example 187-R: (R)-8-chloro-2-(2-(2-chlorophenyl)-1-methyl-4,5,6,7-tetrahydro-1H-benzo[d]imidazol-6-yl)-1,2,3,4-tetrahydroisoquinoline, and Example 187-S: (S)-8-chloro-2-(2-(2-chlorophenyl)-1-methyl-4,5,6,7-tetrahydro-1H-benzo[d]imidazol-6-yl)-1,2,3,4-tetrahydroisoquinoline, shown below.

Example 187-S

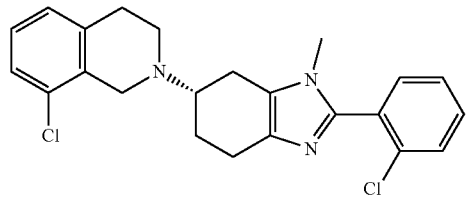

Example 187-R

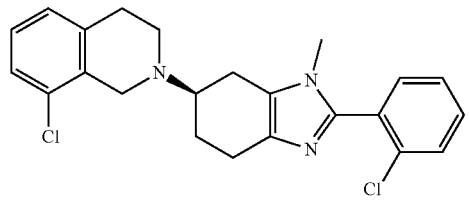

8-chloro-2-(2-(2-chlorophenyl)-1-methyl-4,5,6,7-tetrahydro-1H-benzo[d]imidazol-5-yl)-1,2,3,4-tetrahydroisoquinoline was separated by chiral separation. This resulted in Example 188-R: (R)-8-chloro-2-(2-(2-chlorophenyl)-1-methyl-4,5,6,7-tetrahydro-1H-benzo[d]imidazol-5-yl)-1,2, 3,4-tetrahydroisoquinoline, and Example 188-S: (S)-8-chloro-2-(2-(2-chlorophenyl)-1-methyl-4,5,6,7-tetrahydro-1H-benzo[d]imidazol-5-yl)-1,2,3,4-tetrahydroisoquinoline, shown below.

Example 188-S

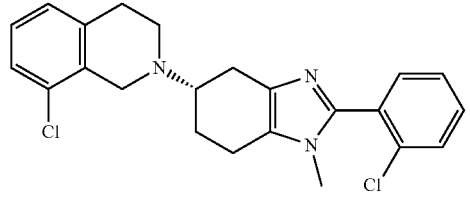

Example 188-R

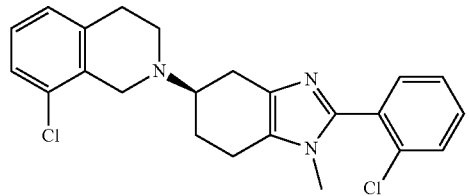

In an alternative procedure, a solution of 8-chloro-2-(2-(2-chlorophenyl)-4,5,6,7-tetrahydro-1H-benzo[d]imidazol-6-yl)-1,2,3,4-tetrahydroisoquinoline (460 mg, 1.16 mmol; Example 185) in dimethylformamide (5 mL) was added NaH (89 mg, 1.28 mmol) at 0° C. under nitrogen atmosphere. The solution was stirred at room temperature for 1 hour, MeI (165 mg, 1.16 mmol) was added dropwise. The reaction solution was stirred at room temperature for 12 hours. The solution was diluted with water (30 mL), extracted with ethyl acetate (30 mL×3). The organic phase was washed with water (30 mL), brine (30 mL), dried, Examples 189 and 190: 6-(4-chloroisoindolin-2-yl)-2-(2-chlorophenyl)-1-methyl-4,5,6,7-tetrahydro-1H-benzo[d]imidazole and 5-(4-chloroisoindolin-2-yl)-2-(2-chlorophenyl)-1-methyl-4,5,6,7-tetrahydro-1H-benzo[d]imidazole

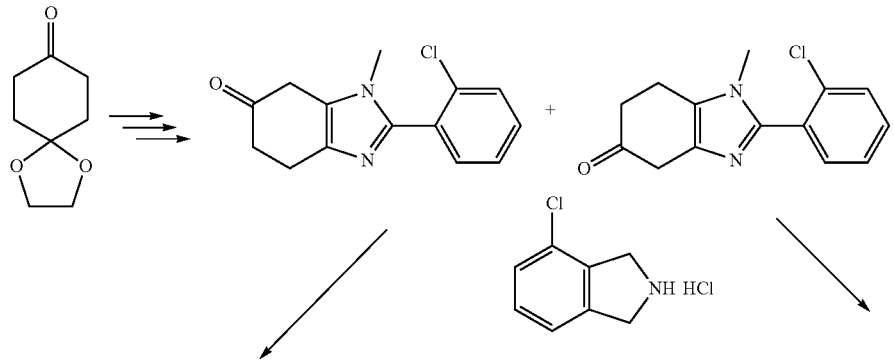

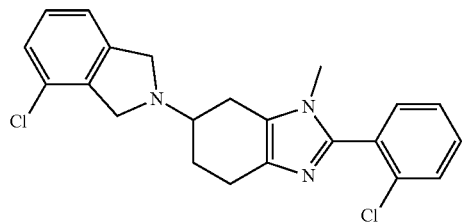

Example 189

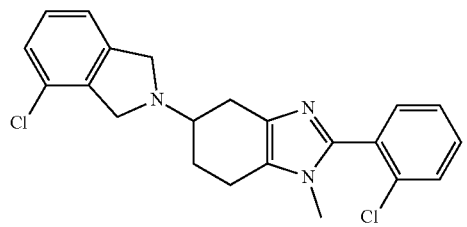

Example 190

2-(2-chlorophenyl)-3-methyl-3,4,6,7-tetrahydro-5H-benzo[d]imidazol-5-one (from Example 187/188) was coupled with 4-chloroisoindoline hydrochloride in a same manner as in Example 186 to obtain Example 189, 6-(4-chloroisoindolin-2-yl)-2-(2-chlorophenyl)-1-methyl-4,5,6,7-tetrahydro-1H-benzo[d]imidazole (ESI-MS [M+H]$^+$: 398.1; $^1$H NMR H NMR (400 MHz, CD$_3$OD): δ ppm 7.78 (m, 2H), 7.66 (m, 2H), 7.45-7.40 (m, 3H), 4.90 (m, 2H), 3.94 (m, 1H), 3.69 (s, 3H), 3.50 (m, 2H), 3.15-3.00 (m, 4H), 2.60 (m, 1H), 2.20 (m, 1H)) and 2-(2-chlorophenyl)-1-methyl-1,4,6,7-tetrahydro-5H-benzo[d]imidazol-5-one (from Example 187/188) was coupled with 4-chloroisoindoline hydrochloride in a same manner as in Example 186 to obtain Example 188, 5-(4-chloroisoindolin-2-yl)-2-(2-chlorophenyl)-1-methyl-4,5,6,7-tetrahydro-1H-benzo[d]imidazole (ESI-MS [M+H]$^+$: 398.1; $^1$H NMR (400 MHz, CD$_3$OD): δ ppm 7.76 (m, 2H), 7.65 (m, 2H), 7.46-7.40 (m, 3H), 4.90 (m, 2H), 3.94 (m, 1H), 3.64 (s, 3H), 3.5 (m, 2H), 3.15-2.96 (m, 4H), 2.65 (m, 1H), 2.24 (m, 1H)).

In an alternative procedure, a solution of 6-(4-chloroisoindolin-2-yl)-2-(2-chlorophenyl)-4,5,6,7-tetrahydro-1H-benzo[d]imidazole (320 mg, 0.84 mmol) in dimethylformamide (6 ml) was added NaH (37 mg, 0.93 mmol) at 0° C. under nitrogen atmosphere. The solution was stirred at room temperature for 1 hour. CH$_3$I (120 mg, 0.84 mmol) was added dropwise. The reaction solution was stirred at room temperature for 12 hours. The solution was diluted with water (30 mL), extracted with ethyl acetate (30 mL×3). The organic phase was washed with water (30 mL), brine (30 mL), dried, concentrated and purified by prep-HPLC to afford the mixture of Example 189 and Example 190.

Examples 191-213

The following compounds are prepared substantially according to the procedures described above:

| Ex. No. | Chemical structure | Chemical name |
|---|---|---|
| 191 | 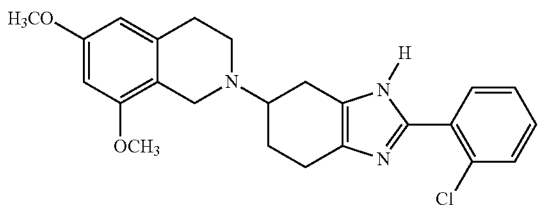 [SMILES: COc1cc2c(c(OC)c1)CN(C1CCc3nc(-c4ccccc4Cl)[nH]c3C1)CC2] | 2-(2-(2-chlorophenyl)-4,5,6,7-tetrahydro-1H-benzo[d]imidazol-6-yl)-6,8-dimethoxy-1,2,3,4-tetrahydroisoquinoline |
| 192 | 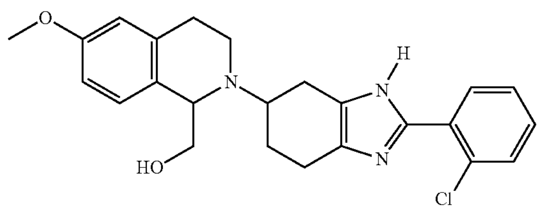 [SMILES: COc1ccc2c(c1)CCN(C1CCc3nc(-c4ccccc4Cl)[nH]c3C1)C2CO] | (2-(2-(2-chlorophenyl)-4,5,6,7-tetrahydro-1H-benzo[d]imidazol-6-yl)-6-methoxy-1,2,3,4-tetrahydroisoquinolin-1-yl)methanol |
| 193 | 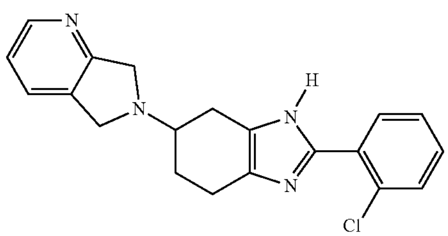 [SMILES: Clc1ccccc1-c1nc2c([nH]1)CC(N1Cc3cccnc3C1)CC2] | 2-(2-chlorophenyl)-6-(5,7-dihydro-6H-pyrrolo[3,4-b]pyridin-6-yl)-4,5,6,7-tetrahydro-1H-benzo[d]imidazole |
| 194 | 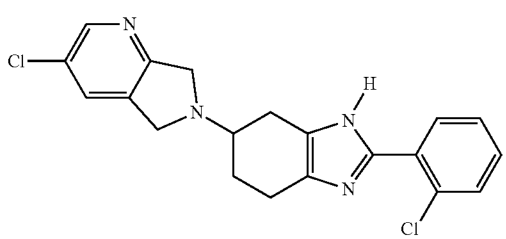 [SMILES: Clc1cnc2c(c1)CN(C1CCc3nc(-c4ccccc4Cl)[nH]c3C1)C2] | 6-(3-chloro-5,7-dihydro-6H-pyrrolo[3,4-b]pyridin-6-yl)-2-(2-chlorophenyl)-4,5,6,7-tetrahydro-1H-benzo[d]imidazole |
| 195 | 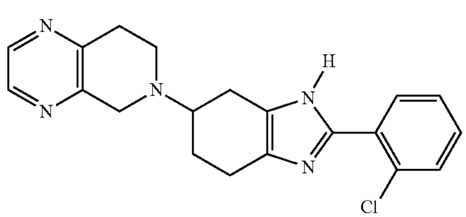 [SMILES: Clc1ccccc1-c1nc2c([nH]1)CC(N1CCc3nccnc3C1)CC2] | 6-(2-(2-chlorophenyl)-4,5,6,7-tetrahydro-1H-benzo[d]imidazol-6-yl)-5,6,7,8-tetrahydropyrido[3,4-b]pyrazine |
| 196 | 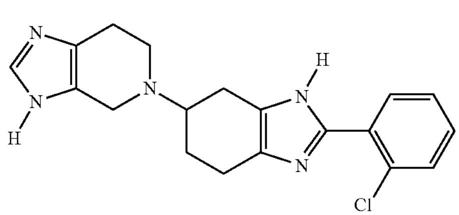 [SMILES: Clc1ccccc1-c1nc2c([nH]1)CC(N1CCc3nc[nH]c3C1)CC2] | 5-(2-(2-chlorophenyl)-4,5,6,7-tetrahydro-1H-benzo[d]imidazol-6-yl)-4,5,6,7-tetrahydro-3H-imidazo[4,5-c]pyridine |

| Ex. No. | Chemical structure | Chemical name |
|---|---|---|
| 197 | 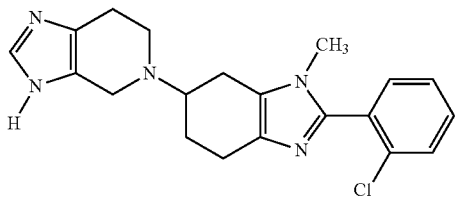 [SMILES: Cn1c(-c2ccccc2Cl)nc2c1CC(N1CCc3nc[nH]c3C1)CC2] | 5-(2-(2-chlorophenyl)-1-methyl-4,5,6,7-tetrahydro-1H-benzo[d]imidazol-6-yl)-4,5,6,7-tetrahydro-3H-imidazo[4,5-c]pyridine |
| 198 | 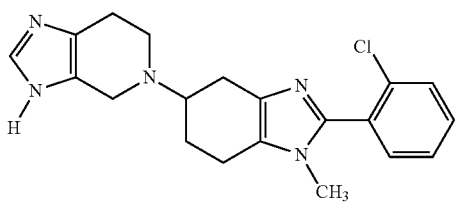 [SMILES: Cn1c(-c2ccccc2Cl)nc2c1CCC(N1CCc3nc[nH]c3C1)C2] | 5-(2-(2-chlorophenyl)-1-methyl-4,5,6,7-tetrahydro-1H-benzo[d]imidazol-5-yl)-4,5,6,7-tetrahydro-3H-imidazo[4,5-c]pyridine |
| 199 | 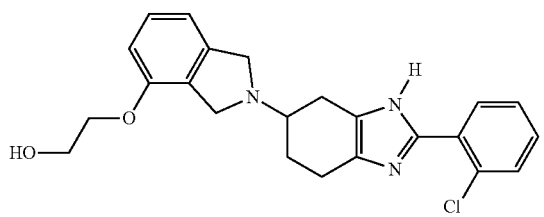 [SMILES: OCCOc1cccc2c1CN(C1CCc3nc(-c4ccccc4Cl)[nH]c3C1)C2] | 2-((2-(2-(2-chlorophenyl)-4,5,6,7-tetrahydro-1H-benzo[d]imidazol-6-yl)isoindolin-4-yl)oxy)ethan-1-ol |
| 200 | 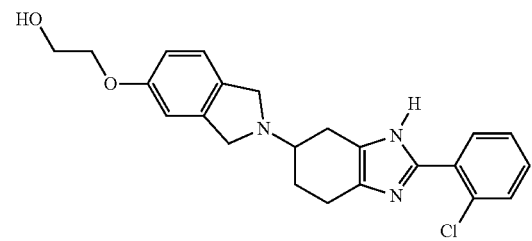 [SMILES: OCCOc1ccc2c(c1)CN(C1CCc3nc(-c4ccccc4Cl)[nH]c3C1)C2] | 2-((2-(2-(2-chlorophenyl)-4,5,6,7-tetrahydro-1H-benzo[d]imidazol-6-isoindolin-5-yl)oxy)ethan-1-ol |
| 201 | 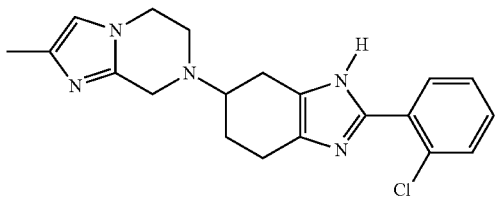 | 7-(2-(2-chlorophenyl)-4,5,6,7-tetrahydro-1H-benzo[d]imidazol-6-yl)-2-methyl-5,6,7,8-tetrahydroimidazo[1,2-a]pyrazine |
| 202 | 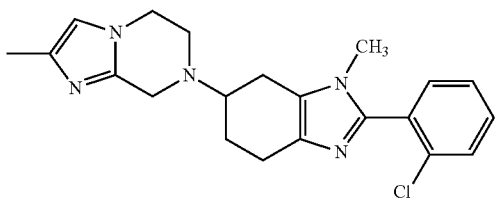 [SMILES: Cc1cn2c(n1)CN(C1CCc3nc(-c4ccccc4Cl)[nH]c3C1)CC2] | 7-(2-(2-chlorophenyl)-1-methyl-4,5,6,7-tetrahydro-1H-benzo[d]imidazol-6-yl)-2-methyl-5,6,7,8-tetrahydroimidazo[1,2-a]pyrazine |
| 203 | 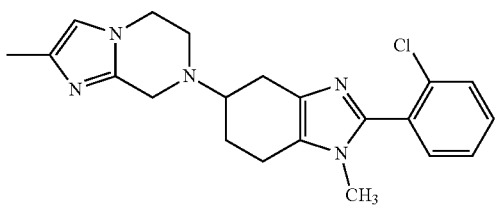 [SMILES: Cc1cn2c(n1)CN(C1CCc3c(nc(-c4ccccc4Cl)n3C)C1)CC2] | 7-(2-(2-chlorophenyl)-1-methyl-4,5,6,7-tetrahydro-1H-benzo[d]imidazol-5-yl)-2-methyl-5,6,7,8-tetrahydroimidazo[1,2-a]pyrazine |

-continued

| Ex. No. | Chemical structure | Chemical name |
|---|---|---|
| 204 | 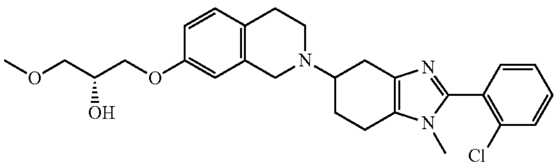 [SMILES: COC[C@@H](O)COc1ccc2c(c1)CN(C1CCc3c(nc(-c4ccccc4Cl)n3C)C1)CC2] | (2R)-1-((2-(2-(2-chlorophenyl)-1-methyl-4,5,6,7-tetrahydro-1H-benzo[d]imidazol-5-yl)-1,2,3,4-tetrahydroisoquinolin-7-yl)oxy)-3-methoxypropan-2-ol |
| 205 | 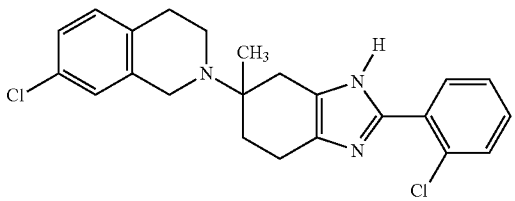 [SMILES: CC1(N2CCc3ccc(Cl)cc3C2)CCc2nc(-c3ccccc3Cl)[nH]c2C1] | 7-chloro-2-(2-(2-chlorophenyl)-6-methyl-4,5,6,7-tetrahydro-1H-benzo[d]imidazol-6-yl)-1,2,3,4-tetrahydroisoquinoline |
| 206 | 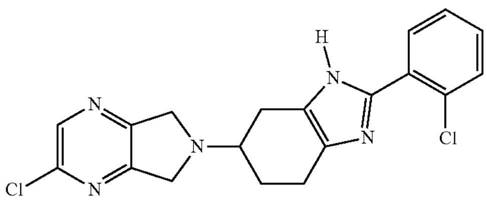 [SMILES: Clc1cnc2c(n1)CN(C1CCc3nc(-c4ccccc4Cl)[nH]c3C1)C2] | 2-chloro-6-(2-(2-chlorophenyl)-4,5,6,7-tetrahydro-1H-benzo[d]imidazol-6-yl)-6,7-dihydro-5H-pyrrolo[3,4-b]pyrazine |
| 207 | 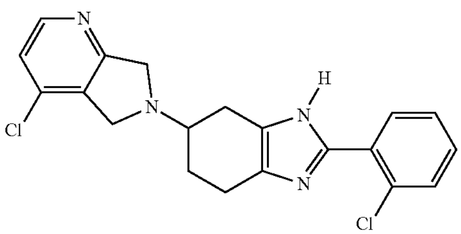 [SMILES: Clc1ccccc1-c1nc2c([nH]1)CC(N1Cc3nccc(Cl)c3C1)CC2] | 6-(4-chloro-5,7-dihydro-6H-pyrrolo[3,4-b]pyridin-6-yl)-2-(2-chlorophenyl)-4,5,6,7-tetrahydro-1H-benzo[d]imidazole |
| 208 | 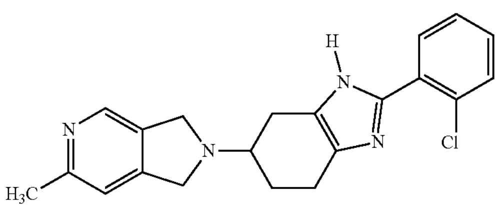 [SMILES: Cc1cc2c(cn1)CN(C1CCc3nc(-c4ccccc4Cl)[nH]c3C1)C2] | 2-(2-chlorophenyl)-6-(6-methyl-1,3-dihydro-2H-pyrrolo[3,4-c]pyridin-2-yl)-4,5,6,7-tetrahydro-1H-benzo[d]imidazole |
| 209 | 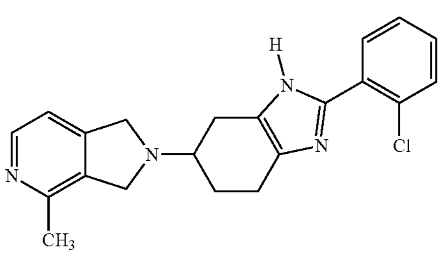 [SMILES: Cc1nccc2c1CN(C1CCc3nc(-c4ccccc4Cl)[nH]c3C1)C2] | 2-(2-chlorophenyl)-6-(4-methyl-1,3-dihydro-2H-pyrrolo[3,4-c]pyridin-2-yl)-4,5,6,7-tetrahydro-1H-benzo[d]imidazole |
| 210 | 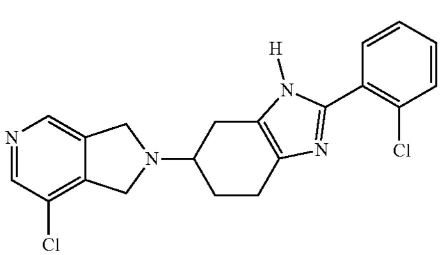 [SMILES: Clc1ccccc1-c1nc2c([nH]1)CC(N1Cc3cncc(Cl)c3C1)CC2] | 6-(7-chloro-1,3-dihydro-2H-pyrrolo[3,4-c]pyridin-2-yl)-2-(2-chlorophenyl)-4,5,6,7-tetrahydro-1H-benzo[d]imidazole |

-continued

| Ex. No. | Chemical structure | Chemical name |
|---|---|---|
| 211 | 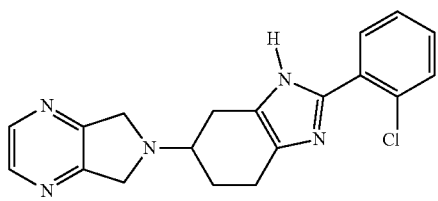 [SMILES: Clc1ccccc1-c1nc2c([nH]1)CC(N1Cc3nccnc3C1)CC2] | 6-(2-(2-chlorophenyl)-4,5,6,7-tetrahydro-1H-benzo[d]imidazol-6-yl)-6,7-dihydro-5H-pyrrolo[3,4-b]pyrazine |
| 212 | 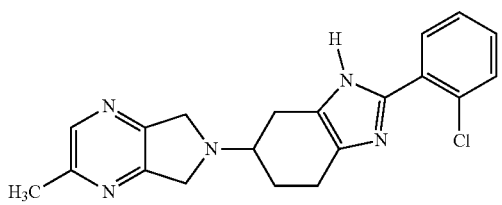 [SMILES: Cc1cnc2c(n1)CN(C1CCc3nc(-c4ccccc4Cl)[nH]c3C1)C2] | 6-(2-(2-chlorophenyl)-4,5,6,7-tetrahydro-1H-benzo[d]imidazol-6-yl)-2-methyl-6,7-dihydro-5H-pyrrolo[3,4-d]pyrimidine |
| 213 | 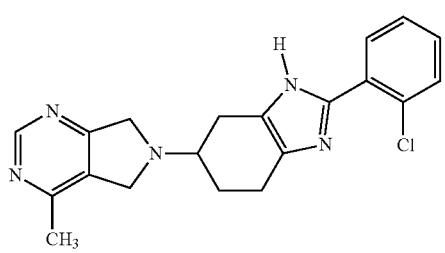 [SMILES: Cc1ncnc2c1CN(C1CCc3nc(-c4ccccc4Cl)[nH]c3C1)C2] | 6-(2-(2-chlorophenyl)-4,5,6,7-tetrahydro-1H-benzo[d]imidazol-6-yl)-4-methyl-6,7-dihydro-5H-pyrrolo[3,4-d]pyrimidine |

Biological Example 1: Gli1-Mediated Transcription Assay

Gli1-mediated transcriptional luciferase reporter assay was performed using Shh-LIGHT2 cells in order to evaluate the effects on activation and inhibition of Gli1-mediated transcription by the compounds of the disclosure. Brief assay procedure is provided below.

Preparation of cell assay plates: Shh-LIGHT2 cells were harvested from about 80% confluent 10-cm dish using 0.25% Trypsin-EDTA solution. Medium was removed, and cells were washed with 5 mL DPBS and aspirated. Then, 1 mL 0.25% Trypsin-EDTA solution was added to a 10-cm dish. The dish was placed in the incubator for 1-3 minutes, or until cells have detached. 3 mL of cell growth medium (DMEM, 10% FBS, 1% PenStrep, 1% sodium pyruvate, and 1% GlutaMax) was added to the 10-cm dish, and the contents were transferred to a conical tube.

Cell density was determined, and using the cell growth medium the volume of the suspension was adjusted to achieve a cell concentration of $3.2\times10^5$ cells/mL (8000 cells/25 µL). 25 µL of the Shh-LIGHT2 cell suspension was transferred to each well of a 384-well white-walled microplate (Corning #3570), and the cells were allowed to sit at room temperature for 30 minutes. The plates were incubated at 37° C./5% $CO_2$ overnight until they reached confluency on the second day.

The cell assay plate was removed from incubator after cells reached confluency. The culture medium was then manually removed from the cell plates, and the plates were centrifuged at 200 rpm for 30 seconds. In the case of antagonist evaluation, compounds (25 µL) were added at semilog concentration (1.5 nM-30 µM final concentration with 0.5% DMSO) in the assay medium (DMEM, 2% FBS, 1% PenStrep, 1% sodium pyruvate, and 1% GlutaMax), then incubated for 30 minutes at 37° C./5% $CO_2$. After 30 min incubation of antagonist, cells were stimulated with agonist (purmorphamine, 5 µL, 1.5 µM final), then incubate for 24 h at 37° C./5% $CO_2$. In the case of angonist evaluation, cells were treated with the compounds in the absence of agonist, then incubated for 24 hr at 37° C./5% $CO_2$.

Luciferase assay: After incubation, the cell assay plate was allowed to acclimate to room temperature. Then, 20 µL of Duo-Glo® Luciferase Reagent (Promega) was added to each well of cell assay plate. The plate was briefly spun down, mixed, and incubated for 30 minutes at room temperature. The cell plate was read using luminometer for firefly luminescence activity. Then, 20 µL of Duo-Glo® Step&Glo® Reagent (Promega) was added to each well of cell assay plate. The plate was briefly spun down, mixed, and incubated for 30 minutes at room temperature. The cell plate was read using luminometer for Renilla luminescence activity. Ratio of firefly: Renilla luminescence was calculated for each well. The compound well ratio was normalized to the ratio from a control well.

The results of Gli1-mediated transcription assay for the representative compounds of the disclosure are provided in Table 1. $IC_{50}$ activity of 1-50 µM is labeled "+", $IC_{50}$ activity of 0.5-0.99 µM is labeled "++", $IC_{50}$ activity of 0.1-0.49 µM is labeled "+++", $IC_{50}$ activity of <0.1 µM is labeled "++++", and $IC_{50}$ activity of >50 µM is labeled "±".

TABLE 1

| | Gli1 $IC_{50}$ | |
|---|---|---|
| Ex. No. | firefly:Renilla ratio | firefly |
| 1 | +++ | ++++ |
| 1-R | +++ | +++ |
| 1-S | +++ | +++ |
| 185 | ++++ | ++++ |
| 185-S | ++++ | +++ |
| 2 | + | + |

TABLE 1-continued

| | Gli1 IC$_{50}$ | |
|---|---|---|
| Ex. No. | firefly:Renilla ratio | firefly |
| 42 | + | + |
| 3 | ++ | ++ |
| 43 | + | ± |
| 4 | + | ++ |
| 51 | + | + |
| 55 | + | + |
| 5 | + | + |
| 6 | + | + |
| 70 | + | + |
| 7 | + | + |
| 8 | + | + |
| 9 | + | ++ |
| 10 | +++ | +++ |
| 22 | +++ | ++ |
| 23 | ++++ | ++++ |
| 24 | ++++ | +++ |
| 106 | + | + |
| 25 | + | + |
| 26 | +++ | ++++ |
| 27 | ++++ | +++ |
| 109 | + | + |
| 28 | +++ | +++ |
| 29 | +++ | ++ |
| 30 | ++ | + |
| 31 | ++ | + |
| 32 | + | + |
| 72 | + | + |
| 73 | ± | ± |
| 77 | + | + |
| 78 | + | + |
| 11 | + | + |
| 12 | +++ | +++ |
| 13 | +++ | +++ |
| 14 | + | + |
| 14-1 | + | + |
| 15 | +++ | +++ |
| 16 | +++ | ++++ |
| 17 | + | ++ |
| 18 | + | + |
| 18-R | ++++ | ++++ |
| 18-S | +++ | +++ |
| 19 | +++ | +++ |
| 99 | + | + |
| 20 | + | + |
| 21 | ++ | ++ |
| 186 | ++++ | ++++ |
| 130 | + | + |
| 34 | +++ | +++ |
| 35 | + | + |
| 36 | ++ | + |
| 161 | +++ | +++ |
| 37 | ++++ | ++++ |
| 163 | ++++ | ++++ |
| 164 | +++ | +++ |
| 187 | ++++ | ++++ |
| 189 | ++++ | ++++ |
| 188 | ++++ | ++++ |

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Various exemplary embodiments of the disclosure include, but are not limited to the enumerated embodiments listed below, which can be combined in any number and in any combination that is not technically or logically inconsistent.

Embodiment 1 provides a compound of the formula (I) as described above.

Embodiment 2 provides the compound of embodiment 1, wherein m is 2, and n is 1.

Embodiment 3 provides the compound of embodiment 1, wherein both m and n are 1.

Embodiment 4 provides the compound of embodiment 1, wherein both m and n are 2.

Embodiment 5 provides the compound of any of embodiments 1-4, wherein p is 0.

Embodiment 6 provides the compound of any of embodiments 1-4, wherein p is 1 or 2.

Embodiment 7 provides the compound of any of embodiments 1-4, wherein p is 1.

Embodiment 8 provides the compound of embodiment 6 or 7, wherein $R_2$ is $C_1$-$C_3$ alkyl.

Embodiment 9 provides the compound of embodiment 6 or 7, wherein $R_2$ is methyl.

Embodiment 10 provides the compound of any of embodiments 1-9, wherein $R_1$ is selected from hydrogen, $C_1$-$C_3$ alkyl, $C_1$-$C_3$ haloalkyl, $C_3$-$C_6$ cycloalkyl, heterocyclyl, hydroxy($C_1$-$C_3$ alkyl), alkoxy($C_1$-$C_3$ alkyl), —OH, and oxetanyl.

Embodiment 11 provides the compound of any of embodiments 1-9, wherein $R_1$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), —OH, and oxetanyl.

Embodiment 12 provides the compound of any of embodiments 1-9, wherein $R_1$ is hydrogen or $C_1$-$C_6$ alkyl.

Embodiment 13 provides the compound of any of embodiments 1-9, wherein $R_1$ is hydrogen or methyl.

Embodiment 14 provides the compound of any of embodiments 1-9, wherein $R_1$ is hydrogen.

Embodiment 15 provides the compound of any of embodiments 1-9, wherein $R_1$ is methyl.

Embodiment 16 provides the compound of any of embodiments 1-15, wherein ring A represents an aryl optionally substituted with one or more $R_3$ or heteroaryl optionally substituted with one or more $R_3$.

Embodiment 17 provides the compound of any of embodiments 1-15, wherein ring A represents phenyl optionally substituted with one or more $R_3$ or 6-membered heteroaryl optionally substituted with one or more $R_3$.

Embodiment 18 provides the compound of any of embodiments 1-15, wherein ring A represents phenyl optionally substituted with one or more $R_3$ or pyridinyl optionally substituted with one or more $R_3$.

Embodiment 19 provides the compound of any of embodiments 1-15, wherein ring A represents phenyl optionally substituted with one or more $R_3$; or wherein ring A represents phenyl substituted with one or more $R_3$; or wherein ring A represents phenyl optionally substituted with one $R_3$; or wherein ring A represents phenyl substituted with one $R_3$.

Embodiment 20 provides the compound of any of embodiments 1-15, wherein ring A represents phenyl.

Embodiment 21 provides the compound of any of embodiments 1-20, wherein each $R_3$ is independently selected from halogen, $C_1$-$C_6$ alkyl optionally substituted with one or more $R_5$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_7$, cyclopropylethynyl, aryl optionally substituted with one or more $R_6$, heteroaryl optionally substituted with one or more $R_6$, heterocyclyl optionally substituted with one or more $R_6$, and $C_3$-$C_8$ cycloalkyl optionally substituted with one or more $R_6$.

Embodiment 22 provides the compound of any of embodiments 1-20, wherein each $R_3$ is independently selected from halogen, $C_1$-$C_6$ alkyl optionally substituted with one or more $R_5$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_7$, cyclopropylethynyl, aryl, heteroaryl, heterocyclyl, and $C_3$-$C_8$ cycloalkyl.

Embodiment 23 provides the compound of any of embodiments 1-20, wherein each $R_3$ is independently selected from halogen, $C_1$-$C_6$ alkyl optionally substituted with one or more $R_5$, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_7$, cyclopropylethynyl, aryl, heteroaryl, heterocyclyl, and $C_3$-$C_8$ cycloalkyl.

Embodiment 24 provides the compound of any of embodiments 1-20, wherein each $R_3$ is independently selected from halogen, $C_1$-$C_6$ alkyl optionally substituted with one or more $R_5$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$SO_2R_7$, cyclopropylethynyl, aryl, heteroaryl, heterocyclyl, and $C_3$-$C_8$ cycloalkyl.

Embodiment 25 provides the compound of any of embodiments 1-20, wherein each $R_3$ is independently selected from halogen, $C_1$-$C_6$ alkyl optionally substituted with one or more $R_5$, $C_1$-$C_6$ haloalkyl, —OH, $C_1$-$C_6$ alkoxy, $C_1$-$C_6$ haloalkoxy, —$SO_2R_7$, cyclopropylethynyl, and heteroaryl.

Embodiment 26 provides the compound of any of embodiments 1-20, wherein each $R_3$ is independently selected from halogen, $C_1$-$C_6$ alkoxy, —$SO_2R_7$, cyclopropylethynyl, and heteroaryl.

Embodiment 27 provides the compound of any of embodiments 1-20, wherein each $R_3$ is independently selected from halogen, $C_1$-$C_6$ alkoxy, cyclopropylethynyl, and heteroaryl; or wherein each $R_3$ is independently selected from halogen, $C_1$-$C_6$ alkoxy, and cyclopropylethynyl.

Embodiment 28 provides the compound of any of embodiments 1-20, wherein each $R_3$ is independently halogen.

Embodiment 29 provides the compound of any of embodiments 1-15, wherein ring A represents phenyl substituted with halogen (e.g., chloro or fluoro).

Embodiment 30 provides the compound of any of embodiments 1-15, wherein ring A represents 2-chlorophenyl.

Embodiment 31 provides the compound of any of embodiments 1-30, wherein ring B and ring C form 1,2,3,4-tetrahydronaphthalenyl, chromanyl, 1,2,3,4-tetrahydroquinolinyl, 1,2,3,4-tetrahydroisoquinolinyl, 2,3-dihydro-1H-indenyl, 2,3-dihydrobenzofuranyl, indolinyl, 1,2,3,4-tetrahydroquinolinyl, or 1,2,3,4-tetrahydroisoquinolinyl, each optionally substituted with one or more $R_4$.

Embodiment 32 provides the compound of any of embodiments 1-30, wherein ring B and ring C form 1,2,3,4-tetrahydronaphthalenyl, chromanyl, 1,2,3,4-tetrahydroquinolinyl, or 1,2,3,4-tetrahydroisoquinolinyl, each optionally substituted with one or more $R_4$.

Embodiment 33 provides the compound of any of embodiments 1-30, wherein ring B and ring C form 1,2,3,4-tetrahydronaphthalenyl, 1,2,3,4-tetrahydroquinolinyl, or 1,2,3,4-tetrahydroisoquinolinyl, each optionally substituted with one or more $R_4$.

Embodiment 34 provides the compound of any of embodiments 1-30, wherein ring B and ring C form 1,2,3,4-tetrahydronaphthalenyl optionally substituted with one or more $R_4$.

Embodiment 35 provides the compound of any of embodiments 1-34, wherein each $R_4$ is independently selected from halogen, —CN, $C_1$-$C_6$ alkyl optionally substituted with one or more $R_5$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —$SO_2R_7$, —$SO_2OR_7$, cyclopropylethynyl, aryl optionally substituted with one or more $R_6$, heteroaryl optionally substituted with one or more $R_6$, heterocyclyl optionally substituted with one or more $R_6$, $C_3$-$C_8$ cycloalkyl optionally substituted with one or more $R_6$, aryloxy optionally substituted with one or more $R_6$, heteroaryloxy optionally substituted with one or more $R_6$, heterocyclyloxy optionally substituted with one or more $R_6$, cycloalkyloxy optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O.

Embodiment 36 provides the compound of any of embodiments 1-34, wherein each $R_4$ is independently selected from halogen, —CN, $C_1$-$C_6$ alkyl optionally substituted with one or more $R_5$, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —$SO_2R_7$, cyclopropylethynyl, heteroaryl optionally substituted with one or more $R_6$, heterocyclyl optionally substituted with one or more $R_6$, $C_3$-$C_8$ cycloalkyl optionally substituted with one or more $R_6$, heteroaryloxy optionally substituted with one or more $R_6$, heterocyclyloxy optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O.

Embodiment 37 provides the compound of any of embodiments 1-34, wherein each $R_4$ is independently selected from halogen, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —$SO_2R_7$, cyclopropylethynyl, heteroaryl optionally substituted with one or more $R_6$, heterocyclyl optionally substituted with one or more $R_6$, 2-hydroxy-3-methoxypropoxy, (2-methoxyethoxy)methyl, and 2-(3-(but-3-yn-1-yl)-3H-diazirin-3-yl)ethoxy; or two $R_4$ groups when attached to the same carbon atom form =O.

Embodiment 38 provides the compound of any of embodiments 1-34, wherein each $R_4$ is independently selected from halogen, $C_1$-$C_6$ alkyl, $C_1$-$C_6$ haloalkyl, —OH, $C_1$-$C_6$ alkoxy, $C_1$-$C_6$ haloalkoxy, —$SO_2R_7$, cyclopropylethynyl, oxetanyl, imidazolyl optionally substituted with $R_6$, and cyclopropyl.

Embodiment 39 provides the compound of any of embodiments 1-34, wherein each $R_4$ is independently selected from halogen, $C_1$-$C_6$ alkyl, —OH, $C_1$-$C_6$ alkoxy, —$SO_2R_7$, cyclopropylethynyl, oxetanyl, imidazolyl optionally substituted with $R_6$, and cyclopropyl.

Embodiment 40 provides the compound of any of embodiments 1-34, wherein each $R_4$ is independently selected from halogen, $C_1$-$C_6$ alkyl, —OH, $C_1$-$C_6$ alkoxy, cyclopropylethynyl, oxetanyl, imidazolyl optionally substituted with methyl, and cyclopropyl; or wherein each $R_4$ is independently selected from halogen, —OH, and $C_1$-$C_6$ alkoxy.

Embodiment 41 provides the compound of any of embodiments 1-34, wherein each $R_4$ is independently selected from halogen, methyl, —OH, methoxy, cyclopropylethynyl, oxetanyl, imidazolyl optionally substituted with methyl, and cyclopropyl; or wherein each $R_4$ is independently selected from halogen, methyl, —OH, and methoxy.

Embodiment 42 provides the compound of any of embodiments 1-34, wherein each $R_4$ is independently halogen.

Embodiment 43 provides the compound of embodiment 1, which is selected from any one of Examples 1-183, or a pharmaceutically acceptable salt thereof.

Embodiment 44 provides a compound of the formula (II) as described above.

Embodiment 45 provides the compound of embodiment 44, wherein t is 2.

Embodiment 46 provides the compound of embodiment 44, wherein t is 1.

Embodiment 47 provides the compound of any of embodiments 44-46, wherein q is 0.

Embodiment 48 provides the compound of any of embodiments 44-46, wherein q is 1 or 2.

Embodiment 49 provides the compound of any of embodiments 44-46, wherein q is 1.

Embodiment 50 provides the compound of embodiment 48 or 49, wherein $R_{12}$ is $C_1$-$C_3$ alkyl.

Embodiment 51 provides the compound of embodiment 48 or 49, wherein $R_{12}$ is methyl.

Embodiment 52 provides the compound of any of embodiments 44-51, wherein $R_{11}$ is selected from hydrogen, $C_1$-$C_3$ alkyl, $C_1$-$C_3$ haloalkyl, $C_3$-$C_6$ cycloalkyl, heterocyclyl, hydroxy($C_1$-$C_3$ alkyl), alkoxy($C_1$-$C_3$ alkyl), —OH, and oxetanyl.

Embodiment 53 provides the compound of any of embodiments 44-51, wherein $R_{11}$ is selected from 1 hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), —OH, and oxetanyl.

Embodiment 54 provides the compound of any of embodiments 44-51, wherein $R_{11}$ is hydrogen or $C_1$-$C_6$ alkyl.

Embodiment 55 provides the compound of any of embodiments 44-51, wherein $R_{11}$ is hydrogen or methyl.

Embodiment 56 provides the compound of any of embodiments 44-51, wherein $R_{11}$ is hydrogen.

Embodiment 57 provides the compound of any of embodiments 44-51, wherein $R_{11}$ is methyl.

Embodiment 58 provides the compound of any of embodiments 44-57, wherein ring X represents an aryl optionally substituted with one or more $R_{13}$ or heteroaryl optionally substituted with one or more $R_{13}$.

Embodiment 59 provides the compound of any of embodiments 44-57, wherein ring X represents phenyl optionally substituted with one or more $R_{13}$ or 6-membered heteroaryl optionally substituted with one or more $R_{13}$.

Embodiment 60 provides the compound of any of embodiments 44-57, wherein ring X represents phenyl optionally substituted with one or more $R_{13}$ or pyridinyl optionally substituted with one or more $R_{13}$.

Embodiment 61 provides the compound of any of embodiments 44-57, wherein ring X represents phenyl optionally substituted with one or more $R_{13}$; or wherein ring X represents phenyl substituted with one or more $R_{13}$; or wherein ring X represents phenyl optionally substituted with one $R_{13}$; or wherein ring X represents phenyl substituted with one $R_{13}$.

Embodiment 62 provides the compound of any of embodiments 44-57, wherein ring X represents phenyl.

Embodiment 63 provides the compound of any of embodiments 44-62, wherein each $R_{13}$ is independently selected from halogen, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, cyclopropylethynyl, aryl optionally substituted with one or more $R_{16}$, heteroaryl optionally substituted with one or more $R_{16}$, heterocyclyl optionally substituted with one or more $R_{16}$, and $C_3$-$C_8$ cycloalkyl optionally substituted with one or more $R_{16}$.

Embodiment 64 provides the compound of any of embodiments 44-62, wherein each $R_{13}$ is independently selected from halogen, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, cyclopropylethynyl, aryl, heteroaryl, heterocyclyl, and $C_3$-$C_8$ cycloalkyl.

Embodiment 65 provides the compound of any of embodiments 44-62, wherein each $R_{13}$ is independently selected from halogen, $C_1$-$C_6$ alkyl optionally substituted with one or more $R_{15}$, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, cyclopropylethynyl, aryl, heteroaryl, heterocyclyl, and $C_3$-$C_8$ cycloalkyl.

Embodiment 66 provides the compound of any of embodiments 44-62, wherein each $R_{13}$ is independently selected from halogen, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SO$_2$R$_{17}$, cyclopropylethynyl, aryl, heteroaryl, heterocyclyl, and $C_3$-$C_8$ cycloalkyl.

Embodiment 67 provides the compound of any of embodiments 44-62, wherein each $R_{13}$ is independently selected from halogen, $C_1$-$C_6$ alkyl optionally substituted with one or more $R_{15}$, $C_1$-$C_6$ haloalkyl, —OH, $C_1$-$C_6$ alkoxy, $C_1$-$C_6$ haloalkoxy, —SO$_2$R$_{17}$, cyclopropylethynyl, and heteroaryl.

Embodiment 68 provides the compound of any of embodiments 44-62, wherein each $R_{13}$ is independently selected from halogen, $C_1$-$C_6$ alkoxy, —SO$_2$R$_{17}$, cyclopropylethynyl, and heteroaryl.

Embodiment 69 provides the compound of any of embodiments 44-62, wherein each $R_{13}$ is independently selected from halogen, $C_1$-$C_6$ alkoxy, cyclopropylethynyl, and heteroaryl; or wherein each $R_{13}$ is independently selected from halogen, $C_1$-$C_6$ alkoxy, and cyclopropylethynyl.

Embodiment 70 provides the compound of any of embodiments 44-62, wherein each $R_{13}$ is independently halogen.

Embodiment 71 provides the compound of any of embodiments 44-57, wherein ring X represents phenyl substituted with halogen (e.g., chloro or fluoro).

Embodiment 72 provides the compound of any of embodiments 44-57, wherein ring X represents 2-chlorophenyl.

Embodiment 73 provides the compound of any of embodiments 44-72, wherein ring Y and ring Z form isoindolin-2-yl, 3,4-dihydroisoquinolin-2(1H)-yl, 3,4-dihydroquinolin-1(2H)-yl, benzo[2,3]morpholin-4-yl, 5,7-dihydro-6H-pyrrolo[3,4-b]pyridine-6-yl, 1,3-dihydro-2H-pyrrolo[3,4-c]pyridin-2-yl, 5,7-dihydro-6H-pyrrolo[3,4-b]pyrazine-6-yl, 5,7-dihydro-6H-pyrrolo[3,4-d]pyrimidin-6-yl, 5,6,7,8-tetrahydro-1,7-naphthyridin-7-yl, 5,6,7,8-tetrahydropyrido[3,4-b]pyrazine-6-yl, 5,6,7,8-tetrahydroimidazo[1,2-a]pyrazin-7-yl, or 3,4,6,7-tetrahydro-5H-imidazo[4,5-c]pyridin-5-yl, each optionally substituted with one or more $R_{14}$.

Embodiment 74 provides the compound of any of embodiments 44-72, wherein ring Y and ring Z form isoindolin-2-yl, 3,4-dihydroisoquinolin-2(1H)-yl, 3,4-dihydroquinolin-1(2H)-yl, 5,6,7,8-tetrahydro-1,7-naphthyridin-7-yl, 5,6,7,8-tetrahydropyrido[3,4-b]pyrazine-6-yl, 5,6,7,8-tetrahydroimidazo[1,2-a]pyrazin-7-yl, or 3,4,6,7-tetrahydro-5H-imidazo[4,5-c]pyridin-5-yl, each optionally substituted with one or more $R_{14}$.

Embodiment 75 provides the compound of any of embodiments 44-72, wherein ring Y and ring Z form isoindolin-2-yl, 3,4-dihydroisoquinolin-2(1H)-yl, or 3,4-dihydroquinolin-1(2H)-yl, each optionally substituted with one or more $R_{14}$.

Embodiment 76 provides the compound of any of embodiments 44-72, wherein ring Y and ring Z form isoindolin-2-yl optionally substituted with one or more $R_{14}$.

Embodiment 77 provides the compound of any of embodiments 44-72, wherein ring Y and ring Z are unsubstituted.

Embodiment 78 provides the compound of any of embodiments 44-76, wherein each $R_{14}$ is independently selected from halogen, —CN, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —SO$_2$R$_{17}$, —SO$_2$OR$_{17}$, cyclopropylethynyl, aryl optionally substituted with one or more $R_{16}$, heteroaryl optionally substituted with one or more $R_{16}$, heterocyclyl optionally substituted with one or more $R_{16}$, $C_3$-$C_8$ cycloalkyl optionally substituted with one or more $R_{16}$, aryloxy optionally substituted with one or more $R_{16}$, heteroaryloxy optionally substituted with one or more $R_{16}$, heterocyclyloxy optionally substituted with one or more $R_{16}$, cycloalkyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O.

Embodiment 79 provides the compound of any of embodiments 44-76, wherein each $R_{14}$ is independently selected from halogen, —CN, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —SO$_2$R$_{17}$, cyclopropylethynyl, heteroaryl optionally substituted with one or more $R_{16}$, heterocyclyl optionally substituted with one or more $R_{16}$, $C_3$-$C_8$ cycloalkyl optionally substituted with one or more $R_{16}$, heteroaryloxy optionally substituted with one or more $R_{16}$, heterocyclyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O.

Embodiment 80 provides the compound of any of embodiments 44-76, wherein each $R_{14}$ is independently selected from halogen, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), —SO$_2$R$_{17}$, cyclopropylethynyl, heteroaryl optionally substituted with one or more $R_{16}$, heterocyclyl optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O.

Embodiment 81 provides the compound of any of embodiments 44-76, wherein each $R_{14}$ is independently selected from halogen, $C_1$-$C_6$ alkyl, $C_1$-$C_6$ haloalkyl, —OH, $C_1$-$C_6$ alkoxy, $C_1$-$C_6$ haloalkoxy, —SO$_2$R$_{17}$, cyclopropylethynyl, oxetanyl, imidazolyl optionally substituted with $R_{16}$, and cyclopropyl.

Embodiment 82 provides the compound of any of embodiments 44-76, wherein each $R_{14}$ is independently selected from halogen, $C_1$-$C_6$ alkyl, —OH, $C_1$-$C_6$ alkoxy, —SO$_2$R$_{17}$, cyclopropylethynyl, oxetanyl, imidazolyl optionally substituted with $R_{16}$, and cyclopropyl.

Embodiment 83 provides the compound of any of embodiments 44-76, wherein each $R_{14}$ is independently selected from halogen, $C_1$-$C_6$ alkyl, —OH, $C_1$-$C_6$ alkoxy, cyclopropylethynyl, oxetanyl, imidazolyl optionally substituted with methyl, and cyclopropyl; or wherein each $R_{14}$ is independently selected from halogen, —OH, and $C_1$-$C_6$ alkoxy.

Embodiment 84 provides the compound of any of embodiments 44-76, wherein each $R_{14}$ is independently selected from halogen, methyl, —OH, methoxy, cyclopropylethynyl, oxetanyl, imidazolyl optionally substituted with methyl, and cyclopropyl; or wherein each $R_{14}$ is independently selected from halogen, methyl, —OH, and methoxy.

Embodiment 85 provides the compound of any of embodiments 44-76, wherein each $R_{14}$ is independently halogen.

Embodiment 86 provides the compound of embodiment 44, which is selected from any one of Examples 185-213, or a pharmaceutically acceptable salt thereof.

Embodiment 87 provides a pharmaceutical composition comprising a compound according to any one of embodiments 1-86 and a pharmaceutically acceptable carrier, solvent, adjuvant or diluent.

Embodiment 88 provides a method of treating neurological disorder, wherein the method comprising administering to a subject in need of such treatment one or more compounds according to any one of embodiments 1-86 or a pharmaceutical composition according to embodiment 87.

Embodiment 89 provides the method of embodiment 88, wherein the neurological disorder is selected from multiple sclerosis, central pontine myelinolysis, acute disseminated encephalomyelitis, progressive multifocal leukoencephalopathy, subacute sclerosing panencephalitis, post-infectious encephalomyelitis, chronic inflammatory demyelinating polyneuropathy, Devic's disease, Balo's concentric sclerosis, the leukodystrophies, optic neuritis, transverse myelitis, cerebral palsy, spinal cord injury, age-associated myelin deficiency, Alzheimer's Disease, and acquired and inherited neuropathies in the peripheral nervous system.

Embodiment 90 provides the method of embodiment 88, wherein the neurological disorder is Multiple Sclerosis.

Embodiment 91 provides the method of embodiment 88, wherein the neurological disorder is Alzheimer's Disease.

Embodiment 92 provides a method of treating a non-CNS disease, the method comprising administering to a subject in need of such treatment one or more compounds according to any one of embodiments 1-86 or a pharmaceutical composition according to embodiment 87.

Embodiment 93 provides the method of embodiment 92, wherein the non-CNS disease is cancer.

Embodiment 94 provides the method of embodiment 93, wherein the cancer is characterized by elevated Gli1.

Embodiment 95 provides the method of embodiment 93, wherein the cancer is breast cancer, pancreatic cancer, colon cancer, lung cancer, rhabdomyosarcoma, basal-cell carcinoma, glioblastoma, medulloblastoma, leukemia, prostate cancer, skin cancer, lymphoma, esophageal cancer, ovarian cancer, thyroid cancer, osteosarcoma, liver cancer, multiple endocrine neoplasia, gastrointestinal cancer, or mesothelioma.

Embodiment 96 provides the method of embodiment 92, wherein the non-CNS disease is cystic kidney disease, chronic liver disease, Hepatitis, C, obstructive pulmonary disease, organ fibrosis, or rheumatoid arthritis.

Embodiment 97 provides a method of inhibiting Gli1, the method comprising administering one or more compounds according to any one of embodiments 1-86 or a pharmaceutical composition according to embodiment 87.

Embodiment 98 provides a method for enhancing remeyelination, the method comprising administering to a subject in need of such treatment one or more compounds according to any one of embodiments 1-86 or a pharmaceutical composition according to embodiment 87.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A compound of the formula (II):

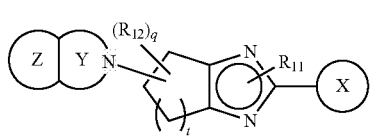

or a pharmaceutically acceptable salt thereof, wherein
t is an integer 1, 2, or 3;
q is an integer 0, 1, or 2;
$R_{11}$ is selected from hydrogen, $C_1$-$C_6$ alkyl, $C_1$-$C_6$ haloalkyl, $C_3$-$C_8$ cycloalkyl, heterocyclyl, hydroxy($C_1$-$C_6$ alkyl), alkoxy($C_1$-$C_6$ alkyl), —OH, and oxetanyl;
$R_{12}$ is $C_1$-$C_6$ alkyl;
ring X represents an aryl optionally substituted with one or more $R_{13}$, heteroaryl optionally substituted with one or more $R_{13}$, or $C_4$-$C_8$ cycloalkyl optionally substituted with one or more $R_{13}$; and
ring Y and ring Z form a bicyclic heteroaryl or bicyclic heterocyclyl moiety, each optionally substituted with one or more $R_{14}$;
wherein
each $R_{13}$ is independently selected from halogen, —NO$_2$, —CN, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —CONH$_2$, —CONH($C_1$-$C_e$ alkyl), —CON($C_1$-$C_6$ alkyl)$_2$, —CONH—OH, —CO$_2$H, —CO$_2$($C_1$-$C_6$ alkyl), —SO$_2$R$_{17}$, —SO$_2$OR$_{17}$, —SO$_2$N(R$_{17}$)$_2$, cyclopropylethynyl, aryl optionally substituted with one or more $R_{16}$, heteroaryl optionally substituted with one or more $R_{16}$, heterocyclyl optionally substituted with one or more $R_{16}$, and $C_3$-$C_8$ cycloalkyl optionally substituted with one or more $R_{16}$;
each $R_{14}$ is independently selected from halogen, —NO$_2$, —CN, $C_1$-$C_6$ alkyl optionally substituted with one or more $R_{15}$, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), —SO$_2$R$_{17}$, —SO$_2$OR$_{17}$, —SO$_2$N(R$_{17}$)$_2$, cyclopropylethynyl, aryl optionally substituted with one or more $R_{16}$, heteroaryl optionally substituted with one or more $R_{16}$, heterocyclyl optionally substituted with one or more $R_{16}$, $C_3$-$C_8$ cycloalkyl optionally substituted with one or more $R_{16}$, aryloxy optionally substituted with one or more $R_{16}$, heteroaryloxy optionally substituted with one or more $R_{16}$, heterocyclyloxy optionally substituted with one or more $R_{16}$, cycloalkyloxy optionally substituted with one or more $R_{16}$, 2-hydroxy-3-methoxypropoxy, (2-methoxyethoxy)methyl, and 2-(3-(but-3-yn-1-yl)-3H-diazirin-3-yl)ethoxy; or two $R_{14}$ groups when attached to the same carbon atom form =O;
each $R_{15}$ is independently selected from the group consisting of halogen, —NO$_2$, —CN, $C_1$-$C_6$ alkyl, $C_1$-$C_6$ haloalkyl, —OH, $C_1$-$C_6$ alkoxy, $C_1$-$C_6$ haloalkoxy, hydroxy($C_1$-$C_6$ alkoxy), alkoxy($C_1$-$C_6$ alkoxy), —SO$_2$R$_{17}$, —SO$_2$OR$_{17}$, and —SO$_2$N(R$_{17}$)$_2$;
each $R_{16}$ is independently selected from the group consisting of halogen, —NO$_2$, —CN, $C_1$-$C_6$ alkyl, $C_1$-$C_6$ haloalkyl, —OH, $C_1$-$C_6$ alkoxy, and $C_1$-$C_6$ haloalkoxy; and
each $R_{17}$ is independently selected from the group consisting of hydrogen, $C_1$-$C_6$ alkyl, phenyl, and tolyl.

2. The compound of claim 1, wherein t is 2; or wherein t is 1.

3. The compound of claim 1, wherein ring X represents an aryl optionally substituted with one or more $R_{13}$ or heteroaryl optionally substituted with one or more $R_{13}$; or wherein ring X represents phenyl optionally substituted with one or more $R_{13}$; or wherein ring X represents phenyl substituted with one or more $R_{13}$; or wherein ring X represents phenyl optionally substituted with one $R_{13}$; or wherein ring X represents phenyl substituted with one $R_{13}$.

4. The compound of claim 1, wherein ring Y and ring Z form isoindolin-2-yl, 3,4-dihydroisoquinolin-2(1H)-yl, 3,4-dihydroquinolin-1(2H)-yl, benzo[2,3]morpholin-4-yl, 5,7-dihydro-6H-pyrrolo[3,4-b]pyridine-6-yl, 1,3-dihydro-2H-pyrrolo[3,4-c]pyridin-2-yl, 5,7-dihydro-6H-pyrrolo[3,4-b]pyrazine-6-yl, 5,7-dihydro-6H-pyrrolo[3,4-d]pyrimidin-6-yl, 5,6,7,8-tetrahydro-1,7-naphthyridin-7-yl, 5,6,7,8-tetrahydropyrido[3,4-b]pyrazine-6-yl, 5,6,7,8-tetrahydroimidazo[1,2-a]pyrazin-7-yl, or 3,4,6,7-tetrahydro-5H-imidazo[4,5-c]pyridin-5-yl, each optionally substituted with one or more $R_{14}$.

5. The compound of claim 1, which is:
8-chloro-2-(2-(2-chlorophenyl)-4,5,6,7-tetrahydro-1H-benzo[d]imidazol-6-yl)-1,2,3,4-tetrahydroisoquinoline;
6-(4-chloroisoindolin-2-yl)-2-(2-chlorophenyl)-4,5,6,7-tetrahydro-1H-benzo[d]imidazole;
2-(2-(2-chlorophenyl)-4,5,6,7-tetrahydro-1H-benzo[d]imidazol-6-yl)-6,8-dimethoxy-1,2,3,4-tetrahydroisoquinoline;
(2-(2-(2-chlorophenyl)-4,5,6,7-tetrahydro-1H-benzo[d]imidazol-6-yl)-6-methoxy-1,2,3,4-tetrahydroisoquinolin-1-yl) methanol;
2-(2-(2-chlorophenyl)-6-(5,7-dihydro-6H-pyrrolo[3,4-b]pyridin-6-yl)-4,5,6,7-tetrahydro-1H-benzo[d]imidazole;

6-(3-chloro-5,7-dihydro-6H-pyrrolo[3,4-b]pyridin-6-yl)-2-(2-chlorophenyl)-4,5,6,7-tetrahydro-1H-benzo[d]imidazole;

6-(2-(2-chlorophenyl)-4,5,6,7-tetrahydro-1H-benzo[d]imidazol-6-yl)-5,6,7,8-tetrahydropyrido[3,4-b]pyrazine;

5-(2-(2-chlorophenyl)-4,5,6,7-tetrahydro-1H-benzo[d]imidazol-6-yl)-4,5,6,7-tetrahydro-3H-imidazo [4,5-c]pyridine;

5-(2-(2-chlorophenyl)-1-methyl-4,5,6,7-tetrahydro-1H-benzo[d]imidazol-6-yl)-4,5,6,7-tetrahydro-3H-imidazo[4,5-c]pyridine;

2-(2-(2-chlorophenyl)-1-methyl-4,5,6,7-tetrahydro-1H-benzo[d]imidazol-5-yl)-4,5,6,7-tetrahydro-3H-imidazo[4,5-c]pyridine;

2-((2-(2-(2-chlorophenyl)-4,5,6,7-tetrahydro-1H-benzo[d]imidazol-6-yl) isoindolin-4-yl)oxy)ethan-1-ol;

2-((2-(2-(2-chlorophenyl)-4,5,6,7-tetrahydro-1H-benzo[d]imidazol-6-yl) isoindolin-5-yl)oxy)ethan-1-ol;

7-(2-(2-chlorophenyl)-4,5,6,7-tetrahydro-1H-benzo[d]imidazol-6-yl)-2-methyl-5,6,7,8-tetrahydroimidazo[1,2-a]pyrazine;

7-(2-(2-chlorophenyl)-1-methyl-4,5,6,7-tetrahydro-1H-benzo[d]imidazol-6-yl)-2-methyl-5,6,7,8-tetrahydro-imidazo[1,2-a]pyrazine;

7-(2-(2-chlorophenyl)-1-methyl-4,5,6,7-tetrahydro-1H-benzo[d]imidazol-5-yl)-2-methyl-5,6,7,8-tetrahydro-imidazo[1,2-a]pyrazine;

8-chloro-2-(2-(2-chlorophenyl)-1-methyl-4,5,6,7-tetrahydro-1H-benzo[d]imidazol-5-yl)-1,2,3,4-tetrahydroisoquinoline;

1-((2-(2-(2-chlorophenyl)-1-methyl-4,5,6,7-tetrahydro-1H-benzo[d]imidazol-5-yl)-1,2,3,4-tetrahydroisoquinolin-7-yl)oxy)-3-methoxypropan-2-ol;

8-chloro-2-(2-(2-chlorophenyl)-1-methyl-4,5,6,7-tetrahydro-1H-benzo[d]imidazol-6-yl)-1,2,3,4-tetrahydroisoquinoline;

5-(4-chloroisoindolin-2-yl)-2-(2-chlorophenyl)-1-methyl-4,5,6,7-tetrahydro-1H-benzo[d]imidazole;

7-chloro-2-(2-(2-chlorophenyl)-6-methyl-4,5,6,7-tetrahydro-1H-benzo[d]imidazol-6-yl)-1,2,3,4-tetrahydroisoquinoline;

6-(4-chloroisoindolin-2-yl)-2-(2-chlorophenyl)-1-methyl-4,5,6,7-tetrahydro-1H-benzo[d]imidazole;

2-chloro-6-(2-(2-chlorophenyl)-4,5,6,7-tetrahydro-1H-benzo[d]imidazol-6-yl)-6,7-dihydro-5H-pyrrolo[3,4-b]pyrazine;

6-(4-chloro-5,7-dihydro-6H-pyrrolo[3,4-b]pyridin-6-yl)-2-(2-chlorophenyl)-4,5,6,7-tetrahydro-1H-benzo[d]imidazole;

2-(2-chlorophenyl)-6-(6-methyl-1,3-dihydro-2H-pyrrolo[3,4-c]pyridin-2-yl)-4,5,6,7-tetrahydro-1H-benzo[d]imidazole;

2-(2-chlorophenyl)-6-(4-methyl-1,3-dihydro-2H-pyrrolo[3,4-c]pyridin-2-yl)-4,5,6,7-tetrahydro-1H-benzo[d]imidazole;

6-(7-chloro-1,3-dihydro-2H-pyrrolo[3,4-c]pyridin-2-yl)-2-(2-chlorophenyl)-4,5,6,7-tetrahydro-1H-benzo[d]imidazole;

6-(2-(2-chlorophenyl)-4,5,6,7-tetrahydro-1H-benzo[d]imidazol-6-yl)-6,7-dihydro-5H-pyrrolo[3,4-b]pyrazine;

6-(2-(2-chlorophenyl)-4,5,6,7-tetrahydro-1H-benzo[d]imidazol-6-yl)-2-methyl-6,7-dihydro-5H-pyrrolo[3,4-d]pyrimidine;

6-(2-(2-chlorophenyl)-4,5,6,7-tetrahydro-1H-benzo[d]imidazol-6-yl)-4-methyl-6,7-dihydro-5H-pyrrolo[3,4-d]pyrimidine; or a pharmaceutically acceptable salt thereof.

6. A pharmaceutical composition comprising a compound according to claim 1 and a pharmaceutically acceptable carrier, solvent, adjuvant, or diluent.

* * * * *